(12) United States Patent
Norris et al.

(10) Patent No.: US 11,547,747 B2
(45) Date of Patent: Jan. 10, 2023

(54) TREATMENT AND DETECTION OF INFECTION AND DISEASE ASSOCIATED WITH DIFFERENT FUNGAL PATHOGENS

(71) Applicant: University of Georgia Research Foundation, Inc., Athens, GA (US)

(72) Inventors: Karen A. Norris, Athens, GA (US); Whitney Rabacal, Athens, GA (US); Emily Rayens, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 66 days.

(21) Appl. No.: 16/650,493

(22) PCT Filed: Sep. 26, 2018

(86) PCT No.: PCT/US2018/052923
§ 371 (c)(1),
(2) Date: Mar. 25, 2020

(87) PCT Pub. No.: WO2019/067592
PCT Pub. Date: Apr. 4, 2019

(65) Prior Publication Data
US 2020/0222517 A1 Jul. 16, 2020

Related U.S. Application Data
(60) Provisional application No. 62/653,755, filed on Sep. 27, 2017.

(51) Int. Cl.
| | | |
|---|---|---|
| *A61K 39/002* | (2006.01) | |
| *A61P 31/10* | (2006.01) | |
| *C07K 16/14* | (2006.01) | |
| *A61K 39/00* | (2006.01) | |

(52) U.S. Cl.
CPC .......... *A61K 39/0002* (2013.01); *A61P 31/10* (2018.01); *C07K 16/14* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,956,778 A | 9/1990 | Naito |
| 4,981,785 A | 1/1991 | Nayak |
| 5,091,513 A | 2/1992 | Huston et al. |
| 5,132,405 A | 7/1992 | Huston et al. |
| 5,225,539 A | 7/1993 | Winter |
| 5,358,691 A | 10/1994 | Clark et al. |
| 5,530,101 A | 6/1996 | Queen et al. |
| 5,585,089 A | 12/1996 | Queen et al. |
| 5,693,762 A | 12/1997 | Queen et al. |
| 5,859,205 A | 1/1999 | Mair et al. |
| 5,885,530 A | 3/1999 | Babson et al. |
| 6,159,750 A | 12/2000 | Edmonds |
| 9,181,538 B1* | 11/2015 | Norris ............... A61K 39/0002 |
| 9,580,704 B2* | 2/2017 | Koi ............... C12Y 304/21061 |
| 9,914,917 B1 | 3/2018 | Norris et al. |
| 2005/0196754 A1 | 9/2005 | Drmanac et al. |
| 2010/0008954 A1 | 1/2010 | Wong et al. |
| 2010/0093557 A1 | 4/2010 | Kumble |
| 2010/0190656 A1 | 7/2010 | Li et al. |
| 2013/0315857 A1 | 11/2013 | Kolls et al. |
| 2013/0344110 A1 | 12/2013 | Selitrennikoff et al. |
| 2018/0153990 A1 | 6/2018 | Gigliotti et al. |

FOREIGN PATENT DOCUMENTS

| | | |
|---|---|---|
| WO | 2004067709 A2 | 8/2004 |
| WO | 2011087934 A2 | 7/2011 |
| WO | 2017139679 A1 | 8/2017 |
| WO | 2019067592 A1 | 4/2019 |
| WO | 2021097021 A2 | 5/2021 |

OTHER PUBLICATIONS

Centers for Disease Control and Prevention, "Medications that Weaken Your Immune System and Fungal Infections," Hindawi, Jan. 25, 2017, Webpage, Retrieved on Jan. 8, 2019; https://www.cdc.gov/fungal/infections/immune-system.html (5 pages).
Eswarappa et al., "Unusual Fungal Infections in Renal Transplant Recipients," Case Reports in Transplantation, Feb. 26, 2015, vol. 2015, No. 292307, pp. 1-4 (4 pages).
Gigliotti et al., "Passive Intranasal Monoclonal Antibody Prophylaxis against Murine Pneumocystis carinii Pneumonia," Infection and Immunity, Mar. 2002, vol. 70, No. 3, pp. 1069-1074 (6 pages).
Loftus et al., "The Genome of the *Basidiomycetous* Yeast and Human Pathogen *Cryptococcus neoformans*," Science, Feb. 25, 2005, vol. 307, No. 5713, pp. 1321-1324 (7 pages).
Nierman et al., "Genomic sequence of the pathogenic and allergenic filamentous fungus *Aspergillus fumigatus*," Mature, Dec. 29, 2005, vol. 438, No. 22, pp. 1151-1156 (7 pages).
International Search Report and Written Opinion in corresponding PCT Patent Application No. PCT/US18/52923, dated Jan. 29, 2019 (24 pages).

(Continued)

*Primary Examiner* — Oluwatosin A Ogunbiyi
(74) *Attorney, Agent, or Firm* — Melissa Hunter-Ensor; Leslie Serunian; Greenberg Traurig, LLP

(57) ABSTRACT

The invention generally provides methods of treating or preventing infection and/or disease associated with different fungal pathogens in a subject in need, using an isolated antiserum generated against an immunogenic peptide of one fungal pathogen that contains antibodies that cross-protect the subject from infection and/or disease associated with one or more different fungal pathogens. The antiserum may be generated against a Kexin peptide derived from one of a *Pneumocystis, Aspergillus, Candida*, or *Cryptococcus* fungal pathogen. The resulting cross-protective, isolated antiserum may be used as a therapeutic for treating or protecting a subject who receives the antiserum against infection and/or disease associated with multiple fungal pathogens, in addition to the pathogen against which the antiserum is generated. Also provided are compositions and kits for detecting or quantifying the presence of antibodies directed against a Kex peptide of one, two, three, or more of *Pneumocystis, Aspergillus, Candida*, or *Cryptococcus* in a subject.

9 Claims, 14 Drawing Sheets

Specification includes a Sequence Listing.

(56) References Cited

OTHER PUBLICATIONS

Gruber et al., "Efficient Tumor Cell Lysis Mediated by a Bispecific Single Chain Antibody Expressed in *Escherichia coli*," The Journal of Immunology, 1994, vol. 152, pp. 5368-5374.
Holliger et al., "'Diabodies': Small bivalent and bispecific antibody fragments," Proceedings of the National Academy of Sciences of the United States of America, Jul. 1993, vol. 90, No. 14, pp. 6444-6448.
Huston et al., "Protein engineering of antibody binding sites: Recovery of specific activity in an anti-digoxin singlechain Fv analogue produced in *Escherichia coli*," Proceedings of the National Academy of Sciences of the United States of America, Aug. 1988, vol. 85, pp. 5879-5883.
Kling et al., Vaccine-Induced Immunogenicity and Protection Against Pneumocystis Pneumonia in a Nonhuman Primate Model of HIV and Pneumocystis Coinfection, The Journal of Infectious Diseases, May 15, 2016, vol. 213, pp. 1586-1595.
Kostelny et al., "Formation of a bispecific antibody by the use of leucine zippers," The Journal of Immunology, Mar. 1, 1992, vol. 148, No. 5, pp. 1547-1553.
Kutty et al., "A Single-Copy Gene Encodes Kex1, a Serine Endoprotease of Pneumocystis jiroveci," Infection and Immunity, Jan. 2003, vol. 71, No. 1, pp. 571-574.
Lee et al., "Molecular characterization of KEX1, a kexin-like protease in mouse Pneumocystis carinii," Gene, 2000, vol. 242, Nos. 1-2, pp. 141-150.
Lilly et al., "The β-Glucan Receptor Dectin-1 Promotes Lung Immunopathology during Fungal Allergy via IL-22," The Journal of Immunology, 2012, vol. 189, pp. 3653-3660.
Olafsen et al., "Covalent disulfide-linked anti-CEA diabody allows site-specific conjugation and radiolabeling for tumor targeting applications," Protein Engineering, Design and Selection, Jan. 2004, vol. 17, No. 1, pp. 21-27.
Power et al., "Generation of Recombinant Multimeric Antibody Fragments for Tumor Diagnosis and Therapy," Methods in Molecular Biology, 2003, vol. 207, pp. 335-350.
Russian et al., "Characterization of a Multicopy Family of Genes Encoding a Surface-Expressed Serine Endoprotease in Rat Pneumocystis carinii," Proceedings of the Association of American Physicians, Jul./Aug. 1999, vol. 111, No. 4, pp. 347-356. [Abstract].

Soltysik et al., "Structure/function studies of QS-21 adjuvant: assessment of triterpene aldehyde and glucuronic acid roles in adjuvant function," Vaccine, 1995, vol. 13, No. 15, pp. 1403-1410.
Tutt et al., "Activation and preferential expansion of rat cytotoxic (CD8) T cells in vitro and in vivo with a bispecific (anti-TCR alpha/beta x anti-CD2) F(ab')2 antibody," The Journal of Immunology, 1995, vol. 155, pp. 2960-2971.
Wahl et al., "Improved Radioimaging and Tumor Localization with Monoclonal F(ab')2," The Journal of Nuclear Medicine, 1983, vol. 24, No. 4, pp. 316-325.
Wu et al., "High-resolution microPET imaging of carcinoembryonic antigen-positive xenografts by using a copper-64-labeled engineered antibody fragment," Proceedings of the National Academy of Sciences of the United States of America, Jul. 18, 2000, vol. 97, No. 15, pp. 8495-8500.
Zapata et al., "Engineering linear F(ab')2 fragments for efficient production in *Escherichia coli* and enhanced antiproliferative activity," Protein Engineering, 1995, vol. 8, No. 10, pp. 1057-1062.
Partial Supplementary European Search Report dated May 31, 2021 in corresponding European Patent Application No. 18861133.9 (10 pages).
Croix et al., "Alterations in T Lymphocyte Profiles of Bronchoalveolar Lavage Fluid from SIV- and Pneumocystis carinii-Coinfected Rhesus Macaques," AIDS Research and Human Retroviruses, 2002, vol. 18, No. 5, pp. 391-401.
Kling et al., "Relationship of Pneumocystis jiroveci Humoral Immunity to Prevention of Colonization and Chronic Obstructive Pulmonary Disease in a Primate Model of HIV Infection," Infection and Immunity, Oct. 2010, vol. 78, No. 10, pp. 4320-4330.
Savoia et al., "Detection of Pneumocystis carinii by DNA Amplification in Human Immunodeficiency Virus-Positive Patients," Diagnostic Microbiology and Infectious Disease, 1997, vol. 29, No. 2, pp. 61-65.
Stolz et al., "Histological Quantification to Determine Lung Fungal Burden in Experimental Aspergillosis," Journal of Visualized Experiments, Mar. 2018, vol. 133, e57155, pp. 1-8.
Uniprot Accession A0A211C4F7. Pheromone processing endoprotease Kex2. (online) Jan. 16, 2019 [online]. [Retrieved Jul. 20, 2021], Retrieved from the Internet: URL: https://www.uniprot.org/uniprot/A0A211C4F7.txt?version=5 >.
Extended European Search Report dated Sep. 3, 2021 in corresponding European Patent Application No. 18861133.9 (9 pages).

* cited by examiner

FIG. 1A

```
P. jirovecii KEX1    DDDGKTVDGPSSIVLRALINGVINGRNGLGSIYVRASGWGGIYEDMCVEDGYAMSVFTTIGGIDKHGKRLKYSEACSSQLAVTYAGGSA
P. macaque KEX1      DDDGKTVDGSPIVLRAFINGVINGRNGLGSIYVRASGWGGIYDMCVEDGYAMSVFTTIGGIDKHGKRAYSEACSSQLAVTYAGGSA
Aspergillus KEX      PDDGATMEGPGILIKRAFVNGVQMRGGKGSIFVRAAGWGASFEDMCVEDGYTNSIYSTVGAIDREGMHPSYSESCSAQLWAYSSGSG
Cryptococcus KEX     PDDGRSMEAPDGLILKAMVNGVQKGRDGKGSVFVRAAGWGGSDDQCMFDGYTNSIFSVTVGAVDRKGLHPYYSEMCAAMWVAPSSSG
Candida KEX          TDMGKVLSEPDVIVKKAMIKGIQEGRDKKGAIVRASGNGGRFGDSCMFDGYTNSIYSTVGAIDYKGLHPQYSEACSAVMVTYSSGSG
                     *:.    :. :*: : :.    *:*****,: **  . , *.******,;.***,;.**.  * .*   *** ,,, ;  ,**.
```

Legend
*(asterisk)  indicates positions which have a single, fully conserved residue
:(colon)     indicates conservation between groups of strongly similar properties as below –
             roughly equivalent to scoring > 0.5 in the Gonnet PAM 250 matrix
.(period)    indicates conservation between groups of weakly similar properties as below –
             roughly equivalent to scoring =< 0.5 and > 0 in the Gonnet PAM 250 matrix Phylogenic tree data (*Pneumocystis* KEX1 and other fungal KEX peptides)

PjiroveciiKEX1 0.02963
PmacaqueKEX1 0.02593
AspergillusKEX 0.12361
CryptococcusKEX 0.17639
CandidaKEX 0.19583

FIG. 2

| %Identity | Pneumocystis Kex1 | Macaque Pneumocystis Kex1 | Aspergillus Kex | Candida Kex | Cryptococcus Kex |
|---|---|---|---|---|---|
| Pneumocystis Kex1 | | 94.444 | 58.889 | 52.222 | 47.778 |
| Macaque Pneumocystis Kex1 | 94.444 | | 58.889 | 52.222 | 48.889 |
| Aspergillus Kex | 58.889 | 58.889 | | 62.222 | 70 |
| Candida Kex | 52.222 | 52.222 | 62.222 | | 62.222 |
| Cryptococcus Kex | 47.778 | 48.889 | 70 | 62.222 | |

| %Similarity (Matrix Blosum62 with threshold 1) | Pneumocystis Kex1 | Macaque Pneumocystis Kex1 | Aspergillus Kex | Candida Kex | Cryptococcus Kex |
|---|---|---|---|---|---|
| Pneumocystis Kex1 | | 95.556 | 75.556 | 72.222 | 73.333 |
| Macaque Pneumocystis Kex1 | 95.556 | | 77.778 | 70 | 72.222 |
| Aspergillus Kex | 75.556 | 77.778 | | 78.889 | 81.111 |
| Candida Kex | 72.222 | 70 | 78.889 | | 81.111 |
| Cryptococcus Kex | 73.333 | 72.222 | 81.111 | 81.111 | |

FIG. 3

Kexin Construct Summary (Highlighted regions are sequences within experimental constructs)

1. *Pneumocystis jirovecii* KEX1
   No reference sequence (Supplemental Data Alignment J.Clin. Invest. 2005 Dec 1; 115(12): 3536-3544.)
   Conserved Sequence and Experimental Construct: (90aa total)
   [sequence]

2. *Pneumocystis macaque* KEX1
   *Pneumocystis carinii* f. sp. macacae kexin mRNA, partial cds.
   GenBank: EU918304.1
   Conserved Sequence and Experimental Construct: (90aa total)
   [sequence]

3. Aspergillus KEX
   *Aspergillus fumigatus* AC293 pheromone processing endoprotease KexB (AFUA_4G13970), partial mRNA
   NCBI Reference Sequence: XM_746441.1
   Conserved Sequence: (90aa total)
   [sequence]
   Experimental Construct: AF_Kex_DS88 (88aa total)
   [sequence]

4. Candida KEX
   *Candida albicans* proteinase (kex2) gene, complete cds
   GenBank: AF022372.1
   Conserved Sequence: (90aa total)
   [sequence]
   Experimental Construct: CA_Kex_DS88 (88aa total)
   [sequence]

5. Cryptococcus KEX
   *Cryptococcus neoformans* var. neoformans JEC21 Kex protein, partial mRNA
   NCBI Reference Sequence: XM_572303.1
   Conserved Sequence: (90aa total)
   [sequence]
   Experimental Construct: CN_Kex_DG117 (117aa total, contains additional 28 downstream aa. FRJHTTDVGRKCSHSRGGTSAAAPLAV) [sequence]...DRSHSRGGTSAAAPLAVGSSPKSLLEPKVDVGTVPAGTKKRYKTFPKPLRPEDFANQLIATVPKKEWFRQSTVTTRPAPSCSEDRLRTTDVGRKCSHSRGGTSAAAPLAVG A. Making vertical dilutions (10 test samples, plus 1 control per plate):

B=Blank (blocking buffer alone)
S=Test sample
N=Normal/negative control

B. Making horizontal dilutions (6 test samples plus 1 control per plate):

ions, such as those with lung diseases or viral infections, such as HIV/AIDS infection, are at a higher risk of developing serious health problems and adverse reactions following exposure to and infection by fungal pathogens.

TREATMENT AND DETECTION OF INFECTION AND DISEASE ASSOCIATED WITH DIFFERENT FUNGAL PATHOGENS

CROSS-REFERENCE TO RELATED APPLICATIONS

This application is the U.S. National Stage Application, pursuant to 35 U.S.C. § 371, of International PCT Application No. PCT/US2018/052923, filed on Sep. 26, 2018, which designated the United States and published in English, and which claims the benefit of and priority to U.S. Provisional Application No. 62/563,755, filed on Sep. 27, 2017, the contents of all of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 28, 2018, is named 173093_010201_PCT_SL.txt and is 32,845 bytes in size.

BACKGROUND OF THE INVENTION

Pathogenic fungal organisms are universal in the environment and can cause global health threats. Pathogenic fungi are typically not harmful to individuals with healthy and normally functional immune systems even after exposure, for example, by inhalation.

However, individuals with weakened or compromised immune systems, or those having pre-existing medical conditions, such as those with lung diseases or viral infections, such as HIV/AIDS infection, are at a higher risk of developing serious health problems and adverse reactions following exposure to and infection by fungal pathogens.

Because of the grave repercussions of infection by fungal organisms in individuals in poor medical health and in those with weakened immune systems, there is an ongoing and urgent need for methods and compositions for treating or preventing infection and associated diseases caused by these pathogens. Cost-effective and efficient methods of treatment of and protection from fungal pathogens are required, particularly in less affluent parts of the world. Effective methods and approaches for treating or preventing infection by fungal pathogens for which suitable therapies are currently nonexistent or inadequate are particularly desirable to alleviate fungal pathogens that pose ever-present threats to at-risk individuals worldwide.

SUMMARY OF THE INVENTION

The invention generally provides methods for treating or preventing infection (e.g., opportunistic infection) by fungal pathogens of different etiologies, as well as treating or preventing pulmonary disease and poor pulmonary function associated with infection by different fungal pathogens. By way of specific example, disease-causing fungal pathogens include *Pneumocystis*, which colonizes lung tissue and causes severe pneumonia after infection; *Aspergillus*, a common mold, which causes aspergillosis, allergic reactions, lung infections and other health problems; *Candida*, which typically reside in the intestinal tract and mucous membranes and can cause thrush, infections and invasive candidiasis upon systemic infection, especially in those in poor health or with weak immune systems; and *Cryptococcus*, which can infect the lungs where it can cause pneumonia-like illness and the brain, where it can cause meningitis.

The present invention stems from the findings described herein that mammalian subjects, immunized with a peptide derived from the Kexin (Kex or Kex1) protein, a subtilisin-like serine protease, from one type of fungal pathogen, *Pneumocystis* (*Pneumocystis* KEX1, Accession No. EU918304.1), elicited an immune response in the form of anti-Kex1 antibodies (monoclonal or polyclonal antibodies) that were cross-reactive with and bound to Kex peptides of other, distinct fungal pathogens, namely, the *Candida*, *Aspergillus* and *Cryptococcus* fungal pathogens. In an embodiment, the mammalian subjects were non-human primates such as rhesus macaques. In accordance with the invention, antiserum obtained or isolated from the immunized subjects contained antibodies that immunologically recognized and reacted with Kex peptides of at least two fungal pathogens different from the original Kex peptide immunogen. This antibody-containing antiserum can serve as a treatment for infection and/or disease caused by more than one fungal pathogen and can provide immunity against multiple fungal pathogens in another or unrelated subject (i.e., a recipient subject) who receives the antiserum via a suitable mode and route of administration. It will be appreciated by the skilled practitioner that, as used herein, a subject from whom an antiserum is obtained or isolated is a "donor subject," and a subject to whom the isolated antiserum is administered or provided is a "recipient subject." In embodiments, a subject is a mammal, particularly a human being or a non-human primate. A recipient subject may be a patient or an individual in need of treatment for or protection from infection or disease caused by one or more of the *Pneumocystis*, *Candida*, *Aspergillus* and/or *Cryptococcus* fungal pathogens.

The production of such immunologically cross reactive antisera (and antibodies therein) produced in subjects (e.g., donor subjects) immunized with, or exposed to, a given fungal Kex peptide, such as aPneumocystis Kex1 peptide, that reacted with the Kex peptides of non-related fungal pathogens, such as *Candida*, *Aspergillus* and *Cryptococcus* fungal pathogens as described herein, was surprising and unexpected, particularly in view of the low amount of amino acid sequence identity (about 48%-70% variability) among the Kex peptides of the *Pneumocystis*, *Candida*, *Aspergillus* and *Cryptococcus* fungal pathogens, and in view of the overall amount of variability in the amino acid sequences (ranging from about 70% to 96% variability) between the Kex1 peptide of *Pneumocystis* and the Kex peptides of the *Candida*, *Aspergillus* and *Cryptococcus* fungal organisms.

In one aspect, the invention provides a method of treating or protecting a subject against infection by a fungal pathogen and/or treating or protecting a subject against a disease or dysfunction (e.g., pulmonary disease, chronic obstructive pulmonary disease (COPD), and/or poor pulmonary function), in which the method comprises administering to a subject (a recipient subject) a peptide immunogen derived from the Kexin protein of a fungal pathogen or an antiserum comprising antibodies produced against the peptide immunogen that is obtained or isolated from a donor subject who has been previously immunized (e.g., inoculation by or exposure to) with a fungal immunogen, e.g., a peptide immunogen derived from the Kexin protein of a fungal pathogen such as *Pneumocystis*, more specifically, *Pneumocystis hominis* or *Pneumocystis jirovecii* (formerly called *Pneumocystis carinii*). In the donor subject, e.g., a non-human primate, the immunogen was provided or present in an amount effective for the donor subject to generate a humoral immune response in which antibodies produced against the original Kex peptide immunogen also cross-reacted with (had binding specificity for and/or activity against) a Kex peptide immunogen of other fungal pathogens (e.g., fungal organisms of different etiologies. In an embodiment, an antiserum is generated in the donor subject against a Kex protein or peptide thereof as shown, for example, in FIG. 4, such as a Kex peptide of about 88-90 amino acids, derived from the fungal pathogen and used as immunogen. In an embodiment, the Kex peptide is the Kex1 peptide from a *Pneumocystis* fungal organism. In a particular embodiment, the immunogen is the Kex1 peptide of *Pneumocystis hominis* or *Pneumocystis jirovecii*. In an embodiment, the *Pneumocystis* Kex1 peptide is a 90 amino acid peptide as isolated from a macaque organism infected with *Pneumocystis macacae* (also called a reference sequence herein). In an embodiment, the immunogen is a Kex1 peptide derived from the Kexin protein of a *Candida* fungal organism. In a particular embodiment, the immunogen is a Kex2 peptide of *Candida albicans*. In an embodiment, the *Candida* Kex1 peptide is a 90 amino acid Kex1 peptide. In an embodiment, the immunogen is a *Candida* Kex1 peptide of 88 amino acids. In an embodiment, the immunogen is a Kex peptide derived from the KexinB protein of an *Aspergillus* fungal organism. In a particular embodiment, the immunogen is a Kex peptide of *Aspergillus fumigatus*. In an embodiment, the *Aspergillus* Kex peptide is a 90-amino acid KexB peptide. In an embodiment, the immunogen is an *Aspergillus* KexB peptide of 88 amino acids. In an embodiment, the immunogen is a Kex peptide derived from the Kexin protein of a *Cryptococcus* fungal organism. In a particular embodiment, the immunogen is a Kex peptide of *Cryptococcus neoformans*. In an embodiment, the *Cryptococcus* Kex peptide is a 90-amino acid Kex peptide. In an embodiment, the immunogen is a *Cryptococcus* Kex peptide of 117 amino acids. In embodiments of any of the foregoing, the Kex1 peptide is recombinantly produced. The amino acid sequences of the above noted peptides are provided herein, for example, as set forth in FIG. 3.

In another aspect, the invention provides a method of treating or protecting a subject against infection by one or more fungal pathogens and/or treating or protecting a subject against disease or dysfunction caused by infection by one or more fungal pathogens (e.g., pulmonary disease, chronic obstructive pulmonary disease (COPD), pneumonia, or poor pulmonary function), in which the method comprises administering to a subject in need thereof a peptide immunogen derived from the Kexin protein of a fungal pathogen or an isolated antiserum containing one or more antibodies directed against an immunogen, e.g., a Kex peptide immunogen derived from the Kexin protein of a fungal pathogen such as *Pneumocystis*, more specifically, *Pneumocystis hominis* or *Pneumocystis carinii*, in an amount effective for the subject to be immunologically protected against infection and/or disease caused by a different (unrelated) fungal pathogen. In an embodiment, the different (unrelated) fungal pathogen comprises a non-identical Kex peptide). According to the method, antibodies in the isolated antiserum cross-react with (have binding specificity for and activity against) a Kex peptide of one or more, particularly, two or more different fungal pathogens. Thus, the method advantageously affords treatment or prevention of infection and/or disease caused by or associated with more than one fungal type, for example, one or more of *Pneumocystis, Aspergillus, Candida* and *Cryptococcus* fungal organisms. In an embodiment, the isolated antiserum is present in a composition, i.e., an immunogenic composition that affords protection against two or more distinct fungal pathogens in the subject receiving the composition following administration.

In another of its aspects, the invention provides a method of generating a cross-protective immune response against different fungal pathogens, e.g., *Pneumocystis, Aspergillus, Candida* and *Cryptococcus* fungal pathogens, in which the method involves administering to a subject (i.e., a recipient subject) an antiserum obtained or isolated from a donor subject who has previously been inoculated with, exposed to, or administered an immunogen comprising a Kexin polypeptide or an immunogenic peptide portion thereof from a fungal pathogen in an amount effective for the donor subject to produce antibodies directed against the Kex polypeptide or peptide immunogen, which antibodies also recognize and bind to a Kexin polypeptide or a peptide portion thereof from a different fungal pathogen. In an embodiment, the antibodies are constituents of the donor subject's blood serum or plasma, which is understood to be an antiserum (immune serum) or immune plasma that can be isolated and employed as treatment or therapy to treat or protect another (unrelated) subject against infection or disease caused by multiple fungal pathogens which comprise a Kex peptide that is specifically targeted by one or more anti-Kex peptide antibodies in the antiserum. In an embodiment, the antiserum is an isolated antiserum. In an embodiment, the immune plasma is isolated immune plasma. In embodiments, the isolated antiserum may be processed, e.g., concentrated, diluted in a suitable diluent or excipient, chromatographed, purified, e.g., via affinity chromatography, using procedures practiced by one of skill in the art, prior to its use as a therapeutic in the methods described herein. In other embodiments, the antibodies administered to a recipient subject may be naturally occurring anti-Kex protein or peptide antibodies that are isolated and purified from another subject who has been naturally exposed (e.g., nonimmunized) to one or more, two or more, or three or more of the fungal pathogens and has consequently raised an anti-Kex protein or peptide antibody immune response against Kex protein or peptide as immunogen. According to this embodiment, during the time of natural exposure of a subject to the fungal pathogens, the exposed subject has generated an immune response (and/or a memory B cell response) comprising monoclonal and/or polyclonal antibodies directed against one or more of the *Pneumocystis, Aspergillus, Candida* and *Cryptococcus* fungal pathogens. In an embodiment, the anti-Kex protein or peptide antibodies isolated (and purified) from the nonimmunized subject are monoclonal antibodies (e.g., directed against the Kex protein or peptide of one of *Pneumocystis, Aspergillus, Candida* and *Cryptococcus*). In an embodiment, the anti-Kex protein or peptide antibodies isolated (and purified) from the nonimmunized subject are polyclonal antibodies (e.g., directed against the Kex protein or peptide of one or more of *Pneumocystis, Aspergillus, Candida* and *Cryptococcus*).

In an embodiment, the antibodies generated by the practice of the described methods constitute a cross-reactive antiserum (e.g., an isolated antiserum), or naturally occurring anti-fungal Kex protein or peptide antibodies isolated and purified from a nonimmunized subject as described above, which may be used as a therapeutic or prophylactic treatment against infection and/or disease or the symptoms thereof caused by one or more fungal pathogens having Kexin polypeptides or a Kex peptide portions thereof that are non-identical (show sequence variability) to the Kexin protein or peptide used as immunogen. In an embodiment, the subject is immunized with a Kex peptide derived from *Pneumocystis* or *Pneumocystis jirovecii*. In an embodiment, the isolated antiserum contains one or more antibodies generated against a Kex peptide derived from *Pneumocystis* or *Pneumocystis jirovecii*, in which the one or more antibodies are cross-reactive (have multi-specificity for) and recognize (e.g., bind to and/or neutralize) a Kex peptide of one or more of *Candida* or *Candida albicans, Aspergillus* or *Aspergillus fumigatus*, or *Cryptococcus* or *Cryptococcus neoformans*. In other embodiments, the isolated antiserum contains one or more antibodies that are generated against a Kex peptide of one or more of *Candida* or *Candida albicans, Aspergillus* or *Aspergillus fumigatus*, or *Cryptococcus* or *Cryptococcus neoformans* and are also cross-reactive with (are multi-specific for) a Kex peptide of *Pneumocystis* or *Pneumocystis jirovecii*. In an embodiment, the naturally occurring anti-fungal Kex protein or peptide antibodies isolated and purified from a nonimmunized subject are monoclonal or polyclonal antibodies directed against the Kex protein or peptide of one, or more than one of *Pneumocystis* or *Pneumocystis jirovecii, Candida* or *Candida albicans, Aspergillus* or *Aspergillus fumigatus*, or *Cryptococcus* or *Cryptococcus neoformans*, as described herein.

In an aspect, the invention provides a method of treating or preventing a disease or symptoms thereof associated with infection by a *Candida* fungal pathogen, in which the method comprises administering to a subject in need thereof an immunologically effective amount of an isolated antiserum, or monoclonal or polyclonal antibodies isolated and purified from a nonimmunized subject, and generated against a Kex1 peptide of *Pneumocystis* or *Pneumocystis jirovecii*. In an embodiment, the fungal pathogen is *Candida albicans*. In an embodiment, the antiserum contains antibodies generated against the 90-amino acid *Pneumocystis* Kex1 peptide (FIG. 3), which antibodies and antiserum are generated in a subject immunized with the *Pneumocystis* Kex1 peptide. In an embodiment, the isolated antiserum is administered in a pharmaceutically acceptable composition.

In an aspect, the invention provides a method of treating or preventing a disease or symptoms thereof associated with infection by an *Aspergillus* fungal pathogen, in which the method comprises administering to a subject in need thereof an immunologically effective amount of an isolated antiserum, or monoclonal or polyclonal antibodies isolated and purified from a nonimmunized subject, generated against a Kex1 peptide of *Pneumocystis* or *Pneumocystis jirovecii*. In an embodiment, the fungal pathogen is *Aspergillus fumigatus*. In an embodiment, the antiserum contains antibodies generated against the 90-amino acid *Pneumocystis* Kex1 peptide, which antibodies and antiserum are generated in a subject immunized with the *Pneumocystis* Kex1 peptide. In an embodiment, the isolated antiserum is administered in a pharmaceutically acceptable composition.

In an aspect, the invention provides a method of treating or preventing a disease or symptoms thereof associated with infection by a *Cryptococcus* fungal pathogen, in which the method comprises administering to a subject in need thereof an immunologically effective amount of an isolated antiserum, or monoclonal or polyclonal antibodies isolated and purified from a nonimmunized subject, generated against a Kex1 peptide of *Pneumocystis* or *Pneumocystis jirovecii*. In an embodiment, the fungal pathogen is *Cryptococcus neoformans*. In an embodiment, the antiserum contains antibodies generated against the 90-amino acid *Pneumocystis* Kex1 peptide (FIG. 3), which antibodies and antiserum are generated in a subject immunized with the *Pneumocystis* Kex1 peptide. In an embodiment, the isolated antiserum is administered in a pharmaceutically acceptable composition.

In embodiment of any of the foregoing aspects, the antiserum (e.g., isolated antiserum), or monoclonal or polyclonal antibodies isolated and purified from a nonimmunized subject, comprising anti-Kex peptide antibodies can treat or protect a subject against infection and disease, such as pulmonary disease, pneumonia, or fungal colonization in lung or brain tissue, caused by one or more different fungal pathogens. In a particular embodiment, the antiserum (isolated antiserum) comprising anti-*Pneumocystis hominis* or *Pneumocystis jirovecii* Kex1 peptide antibodies is used in the treatment of disease or infection of a subject who is infected by, or who is at risk of infection by, a fungal organism selected from *Aspergillus fumigates, Candida albicans* and *Cryptococcus neoformans*.

In an aspect, the invention provides a method of immunizing a subject to treat or prevent disease resulting from infection by one or more fungal pathogens, comprising administering to the subject an antiserum (e.g., an isolated antiserum), or monoclonal or polyclonal antibodies isolated and purified from a nonimmunized subject, comprising antibodies that specifically target and bind to two or more of a *Pneumocystis* Kex protein or peptide, an *Aspergillus, Candida* or *Cryptococcus* Kex protein or peptide. In an embodiment, the method elicits a B-cell memory response for protection against subsequent exposure to one or more of the fungal pathogens.

In embodiments of any of the foregoing aspects, the methods are useful for treating and protecting against pulmonary (lung) disease, such as chronic obstructive pulmonary disease (COPD), including, without limitation, bronchitis, chronic bronchitis, emphysema, asthma including severe asthma (e.g., refractory (non-reversible asthma)), or bronchiectasis. In other embodiments, the methods are useful for treating or protecting against colonization of one or more of the fungal pathogens in tissues and organs of an infected subject, such as lung or brain tissue. In other embodiments, the methods are useful for treating or protecting against disease and/or infection of brain and spinal tissue, e.g., against meningitis, such as *Cryptococcal* meningitis (CM).

In one aspect, the invention provides a method of providing immunity (or immune protection) to a subject in need who has an infection or who is at risk of having an infection by one or more, or two or more, different fungal types, including *Pneumocystis, Aspergillus, Candida* and *Cryptococcus* fungal organisms, by administering to the subject an isolated antiserum, or monoclonal or polyclonal antibodies isolated and purified from a nonimmunized subject, generated against a Kexin protein or a Kex peptide portion thereof, of a fungal pathogen as described herein. In an embodiment, the Kex peptide is an antigenically stable active site peptide sequence of a Kexin protein as described herein. In an embodiment, the isolated antiserum is generated against a *Pneumocystis* Kex peptide. In an embodiment, the isolated antiserum is generated against an *Aspergillus* Kex peptide. In an embodiment, the isolated antiserum is generated against a *Candida* Kex peptide. In an embodiment, the isolated antiserum is generated against a *Cryptococcus* Kex peptide. In an embodiment, the antiserum is generated in (and isolated from) one organism or subject and administered to another organism or subject who has or who is at risk of having an infection by one or more of the fungal organisms described herein. In an embodiment, the immunity provided by the practice of the method is humoral immune protection (antibody protection) against one or more of the fungal organisms described herein, in particular, against the Kex protein or Kex peptide of one or more of the described fungal organisms. In a particular embodiment, the immunity provided by the practice of the method is an acquired or passive humoral immune protection (antibody protection) provided to a recipient subject against one or more of the fungal organisms described herein, in particular, against the Kex protein or Kex peptide of one or more of the described fungal organisms. In an embodiment, the isolated antiserum is administered in a pharmaceutically acceptable composition.

In another aspect, the invention provides a method of treating or preventing infection caused by one or more of *Pneumocystis, Aspergillus, Candida*, or *Cryptococcus* fungal organisms, in which the method involves administering to a subject who is infected or who is at risk of infection with an isolated antiserum containing antibodies that are generated against and target the Kex protein or a Kex1 peptide as described herein, or naturally occurring anti-Kex protein or peptide monoclonal or polyclonal antibodies isolated and purified from a nonimmunized subject, wherein the Kex protein or a Kex peptide thereof is from at least one of *Pneumocystis, Aspergillus, Candida*, or *Cryptococcus* fungal organisms. In an embodiment, the Kex peptide is an antigenically stable active site peptide sequence of the Kexin protein, which comprises conserved amino acids among several different fungal organisms, namely, *Pneumocystis hominis, Aspergillus fumigates, Candida albicans* and *Cryptococcus neoformans*. In an embodiment, the isolated antiserum is administered in a pharmaceutically acceptable composition.

In another aspect, the invention provides a method of treating or preventing a fungal induced pulmonary disease or symptoms thereof in a subject, the method involving administering to a subject in need thereof an isolated anti-Kexin protein or peptide antibody or an antigen-binding fragment thereof generated against a Kex peptide from one type of fungal organism, e.g., *Pneumocystis*, or an isolated antiserum comprising such an antibody or an antigen binding fragment thereof, which antibody, antigen binding fragment thereof, or isolated antiserum immunizes the subject against pulmonary disease caused by other fungal types, for example, *Aspergillus, Candida* and *Cryptococcus* fungal pathogens, and more specifically, *Aspergillus fumigatus, Candida albicans* and *Cryptococcus neoformans* fungal pathogens. In an embodiment, the method involves administering anti-fungal Kexin protein or peptide monoclonal or polyclonal antibodies isolated and purified from a nonimmunized subject as described herein. In an embodiment, the isolated antiserum or the isolated and purified naturally occurring antibodies are administered in a pharmaceutically acceptable composition.

In an aspect, an antiserum isolated from a subject immunized with an approximately 90 amino acid peptide segment of the subtilisin-like serine proteinase Kexin of *Pneumocystis* (*Pneumocystis* KEX1 (Accession no. EU918304.1), namely, a Kex peptide, comprises antibodies that also recognized Kex peptides derived from different fungal pathogens, such as *Pneumocystis, Aspergillus, Candida* and *Cryptococcus* fungal pathogens, and more specifically, in the *Pneumocystis hominis, Aspergillus fumigatus, Candida albicans* and *Cryptococcus neoformans* fungal species. (FIG. 1). Accordingly, such antiserum (isolated antiserum) and the antibodies contained therein can serve as a therapeutic or protective treatment not only against infection or disease associated with *Pneumocystis* infection, but also against infection or disease associated with infection by one or more of the *Aspergillus, Candida* and *Cryptococcus* fungal pathogens in a subject immunized with or administered the antiserum. In an embodiment, the antiserum treats or protects against pulmonary disease, such as poor pulmonary function, COPD, or pneumonia. In an embodiment, the methods and compositions described herein are advantageously useful for providing high levels of antibodies (and increased antibody titers) directed against an antigenic region of the Kexin protein in the *Pneumocystis, Aspergillus, Candida* and *Cryptococcus* fungal pathogens to a subject in need thereof. In a particular embodiment, the methods are useful for the treatment or protection of cigarette smokers who are at risk for COPD and in patients with COPD, so as to ameliorate airway obstruction and to treat or prevent more severe airway obstruction and progressive COPD in these individuals. In an embodiment, the compositions and methods described herein are advantageously useful for providing high levels of cross-reactive antibodies (and increased antibody titers) directed against Kex1 peptides of the *Pneumocystis, Aspergillus, Candida* and *Cryptococcus* fungal pathogens. In another particular embodiment, the methods are useful for the treatment or protection of a subject in need from colonization of tissue, e.g., lung tissue, with the *Pneumocystis, Aspergillus, Candida* and *Cryptococcus Pneumocystis* fungal pathogens. In a particular embodiment, the fungal pathogen is *Aspergillus fumigatus*, which is associated with COPD and poor pulmonary function. In an embodiment, the antiserum is an isolated antiserum or a purified antiserum. In an embodiment, antibodies from the antiserum may be purified by methods known and practiced in the art, and the purified antibodies (in a pharmaceutically acceptable composition) may be provided to a recipient subject.

In another aspect, the invention provides a kit containing the isolated antiserum containing antibodies or antigen-binding fragments thereof generated against a Kex peptide according to any aspect delineated herein. In an embodiment, the isolated antiserum is in a pharmaceutically acceptable composition. In another embodiment, the kit contains antibodies or antigen binding fragments thereof purified from an anti-fungal Kex peptide antiserum obtained or isolated as described herein and in a pharmaceutically acceptable composition.

In various embodiments of any aspect delineated herein, the subject is human. In various embodiments of any aspect delineated herein, the subject is infected with or is at risk of infection with a fungal organism selected from the *Pneumocystis, Aspergillus, Candida*, or *Cryptococcus* fungal pathogens. In various embodiments of any aspect delineated herein, the subject has or is at risk of having a pulmonary disease, e.g., COPD. In an embodiment of any aspect delineated herein, the fungal infection is neutralized in the subject. In an embodiment of any aspect delineated herein, tissue colonization by a fungal pathogen is reduced, diminished, or alleviated in a subject. In various embodiments of any aspect delineated herein, the antibody or antigen-binding fragment thereof is obtained from blood, plasma, or serum.

In an aspect, a method of cross-protecting a subject against infection and/or disease by different fungal pathogens is provided, in which the method involves administering to a subject in need thereof an isolated antiserum produced against a peptide immunogen derived from the Kexin protein of aPneumocystis fungal pathogen in an amount effective for the subject to acquire cross-protective immunity (e.g., humoral immunity) against infection and/or disease associated with one or more of an *Aspergillus*,

*Candida*, or *Cryptococcus* fungal pathogen. In an embodiment, the isolated antiserum is in a pharmaceutically acceptable composition.

In another aspect, a method of treating a subject having a disease or dysfunction associated with infection by different fungal pathogens is provided in which the method involves administering to a subject in need thereof a peptide immunogen derived from the Kexin protein of a *Pneumocystis* fungal pathogen or an isolated antiserum produced against a peptide immunogen derived from the Kexin protein of a *Pneumocystis* fungal pathogen in an amount effective to treat the subject for the disease or dysfunction associated with infection by one or more of an *Aspergillus, Candida*, or *Cryptococcus* fungal pathogen. In an embodiment, the isolated antiserum is in a pharmaceutically acceptable composition.

In embodiments of the above aspects, the antiserum is generated against a Kex peptide of *Pneumocystis hominis* or *Pneumocystis jirovecii*. In embodiments of the above aspects, the cross-protection or treatment is against infection and/or disease or dysfunction associated with one or more of *Aspergillus fumigatus, Candida albicans*, or *Cryptococcus neoformans*. In embodiments of the above aspects, the subject is cross-protected against or treated for a disease or dysfunction selected from pulmonary disease, chronic obstructive pulmonary disease (COPD), poor pulmonary function, or a symptom thereof. In embodiments of the above aspects, the antiserum is generated in the subject against the 90-amino acid Kex peptide derived from the *Pneumocystis hominis* or *Pneumocystis jirovecii* fungal pathogen. (FIG. 3). In an embodiment of any of the above aspects, the antiserum is an isolated antiserum which allows a recipient subject to acquire immunity to multiple fungal pathogens as described herein.

In another aspect, a method of cross-protecting a subject against infection and/or disease by different fungal pathogens is provided in which the method involves administering to a subject in need thereof an isolated antiserum produced against a peptide immunogen derived from the Kexin protein of a fungal pathogen selected from one or more of *Pneumocystis, Aspergillus, Candida*, or *Cryptococcus* in an amount effective for the subject to acquire cross-protective immunity against infection and/or disease associated with the *Aspergillus, Candida*, or *Cryptococcus* fungal pathogen. In an embodiment, the isolated antiserum is in a pharmaceutically acceptable composition.

In another aspect, a method of treating a subject having a disease, dysfunction, or symptoms thereof associated with infection by different fungal pathogens is provided in which the method involves administering to a subject in need thereof an isolated antiserum produced against a peptide immunogen derived from the Kexin protein of a fungal pathogen selected from one or more of *Pneumocystis, Aspergillus, Candida*, or *Cryptococcus* in an amount effective for the subject to acquire immunity against and to treat a disease, dysfunction, or symptoms thereof associated with infection by at least two of the *Pneumocystis, Aspergillus, Candida*, or *Cryptococcus* fungal pathogens. In an embodiment of the foregoing aspects, the peptide immunogen is a Kex1 peptide derived from *Pneumocystis hominis* or *Pneumocystis jirovecii*. In another embodiment of the foregoing aspects, the *Pneumocystis* Kex1 peptide is a 90-amino acid peptide (FIG. 3) and is encoded by a polynucleotide contained in an expression vector. In another embodiment of the foregoing aspects, the peptide immunogen is a Kex1 peptide derived from *Candida albicans*. In another embodiment of the foregoing aspects, the *Candida* Kex1 peptide is an 88-amino acid peptide (FIG. 3) and is encoded by a polynucleotide contained in an expression vector. In another embodiment of the foregoing aspects, the peptide immunogen is a Kex1 peptide derived from *Aspergillus fumigatus*. In another embodiment of the foregoing aspects, the *Aspergillus* Kex1 peptide is an 88-amino acid peptide (FIG. 3) and is encoded by a polynucleotide contained in an expression vector. In another embodiment of the foregoing aspects, the peptide immunogen is a Kex1 peptide derived from *Cryptococcus neoformans*. In another embodiment of the foregoing aspects, the *Cryptococcus* Kex1 peptide is a 117-amino acid peptide (FIG. 3) and is encoded by a polynucleotide contained in an expression vector. (FIG. 3). In an embodiment of the foregoing aspects, the isolated antiserum is in a pharmaceutically acceptable composition.

In another aspect, a method of treating or preventing an infection is provided in which the method involves administering to a subject who is infected or who is at risk of infection by two or more of *Pneumocystis, Aspergillus, Candida*, or *Cryptococcus* fungal pathogens an isolated antiserum generated in a different subject (a donor subject) who has mounted an antibody-mediated immune response against one of *Pneumocystis, Aspergillus, Candida*, or *Cryptococcus* fungal pathogens. In an embodiment of the method, the antiserum comprises one or more antibodies or antigen-binding fragments thereof that target and bind to a Kex peptide of a *Pneumocystis, Aspergillus, Candida*, or *Cryptococcus* fungal pathogen, in particular, two or more of the *Pneumocystis, Aspergillus, Candida*, or *Cryptococcus* fungal pathogens. In an embodiment, the isolated antiserum is in a pharmaceutically acceptable composition.

In another aspect, a method of treating or preventing an infection is provided in which the method involves administering to a subject infected or at risk of infection by *Pneumocystis, Aspergillus, Candida*, or *Cryptococcus* fungal pathogens an antiserum isolated from a donor subject who has generated an immune response to a Kex peptide of a *Pneumocystis* fungal pathogen.

In another aspect, a method of treating or preventing an infection is provided in which the method involves administering to a subject infected or at risk of infection by *Pneumocystis, Aspergillus, Candida*, or *Cryptococcus* fungal pathogens an antiserum isolated from a donor subject who has generated an immune response to a Kex peptide of an *Aspergillus* fungal pathogen.

In another aspect, a method of treating or preventing an infection is provided in which the method involves administering to a subject infected or at risk of infection by *Pneumocystis, Aspergillus, Candida*, or *Cryptococcus* fungal pathogens an antiserum isolated from a donor subject who has generated an immune response to a Kex peptide of a *Candida* fungal pathogen.

In another aspect, a method of treating or preventing an infection is provided in which the method involves administering to a subject infected or at risk of infection by *Pneumocystis, Aspergillus, Candida*, or *Cryptococcus* fungal pathogens an antiserum isolated from a donor subject who has generated an immune response to a Kex peptide of a *Cryptococcus* fungal pathogen.

In an embodiment of any of the above aspects, the antiserum is an isolated or purified antiserum. In an embodiment of any of the above aspects, the antiserum has neutralizing activity against a fungal pathogen or prevents colonization of a fungal pathogen in the subject. In an embodiment of any of the above aspects, the donor and recipient subjects are mammals, particularly, human beings. In another embodiment of the above aspects, the recipient subject has or is at risk of having an infection or disease caused by more than one, e.g., two or more, fungal pathogen(s) selected from *Pneumocystis, Aspergillus, Candida*, or *Cryptococcus*. In an embodiment of any of the above aspects, the subject receiving the isolated or purified antiserum is immunocompromised. In an embodiment of any of the above aspects, the subject receiving the isolated or purified antiserum is cross-protected against or treated for a disease or dysfunction or symptom thereof selected from pulmonary disease, chronic obstructive pulmonary disease (COPD), poor pulmonary function, or pneumonia, caused by or associated with infection by a fungal pathogen as described herein.

In another aspect, the invention encompasses a kit for detecting, qualifying, or quantifying the levels of, antibodies directed against the Kex protein derived from *Pneumocystis, Aspergillus, Candida*, or *Cryptococcus* fungal pathogens in a patient sample, the kit comprising a solid substrate having attached thereto a Kex peptide derived from one or more, two or more, three or more, or each of *Pneumocystis, Aspergillus, Candida*, or *Cryptococcus* fungal pathogens. In an embodiment, the kit further comprises a labeled detection molecule for detecting and measuring the level of antibodies that bind to the Kex peptides on the substrate. In an embodiment, the kit is used for performing an immunoassay, which may be an enzyme linked immunosorbent assay (ELISA). In an embodiment, the kit also contains a positive and/or a negative control for detecting, qualifying, or quantifying antibody levels.

In another aspect, the invention encompasses a composition comprising a solid substrate and a plurality of Kex peptides derived from one or more of *Pneumocystis, Aspergillus, Candida*, or *Cryptococcus* fungal pathogens immobilized on the substrate. In an embodiment, a Kex peptide from each of *Pneumocystis, Aspergillus, Candida*, or *Cryptococcus* fungal pathogens is immobilized at a different, indexable, location on the substrate. In an embodiment, a mixture of Kex peptides from two or more, three or more, or all four of the *Pneumocystis, Aspergillus, Candida*, or *Cryptococcus* fungal pathogens is immobilized at a different, indexible, location on the substrate. In an embodiment, the binding of anti-Kex peptide antibodies from a sample obtained from a subject can be measured or detected by measuring or detecting complexes of the anti-Kex peptide antibodies bound to the Kex peptides localized on the substrate. In an embodiment, the composition is contained in a kit for performing an immunoassay, which may be an enzyme linked immunosorbent assay (ELISA).

In another aspect, the invention provides a method of diagnosing a subject as being at risk of infection by one or more fungal pathogens and/or fungal-associated disease or symptoms thereof, in which the method comprises: contacting a Kexin (Kex) protein or peptide derived from at least two of *Pneumocystis, Aspergillus, Candida*, or *Cryptococcus* fungal pathogens with a biological sample of the subject to detect antibodies or antigen binding fragments thereof in the sample that specifically bind to the Kex protein or peptide; detecting the binding levels of the anti-Kex protein or peptide antibodies or antigen binding fragments thereof in the sample to the Kex protein or peptide relative to control binding levels; and diagnosing the subject as being at risk of infection or disease by the fungal pathogens when low or negligible levels of the Kex protein or peptide binding to antibodies or antigen binding fragments are detected in the subject's sample relative to control levels, and diagnosing the subject as not being at risk of infection or disease by the fungal pathogens when moderate or high levels of the Kex protein or peptide binding to antibodies or antigen binding fragments are detected in the subject's sample relative to control levels. In accordance with this aspect, normal human sera with undetectable absorbance at $OD_{450}$ (i.e., equal to or less than the $OD_{450}$ absorbance measured for dilution buffer alone) in KEX-ELISA at a dilution of 1:100 is used as a negative control. Based on the distribution of *Pneumocystis* KEX1 reciprocal endpoint antibody titers (RET) in human subjects, negative to low titer range is between about 1 to about 3200 RET, moderate titer levels are about 3200 to about 12,800 and high titer levels are greater than (>) 12,800 RET.

In another aspect, the invention provides a method of stratifying a subject into a patient population that is at risk or that is not at risk of being infected by one or more fungal pathogens and/or disease associated therewith, in which the method comprises: contacting a Kexin (Kex) protein or peptide derived from one or more fungal pathogens selected from *Pneumocystis, Aspergillus, Candida*, or *Cryptococcus* with a biological sample of the subject to detect antibodies or antigen binding fragments thereof in the sample that specifically bind to the Kex protein or peptide; detecting and measuring levels of antibodies or antigen binding fragments thereof in the subject's sample that specifically bind to one or more of the fungal-derived Kex protein or peptide; and stratifying the subject into (i) a patient population that is at risk of having infection and/or disease associated with exposure to one or more of the *Pneumocystis, Aspergillus, Candida*, or *Cryptococcus* fungal pathogens when low or negligible levels of anti-Kex protein or peptide antibodies or antigen binding fragments thereof are detected and measured relative to a control, or (ii) a patient population that is not at risk of having infection and/or disease associated with exposure to one or more of the *Pneumocystis, Aspergillus, Candida*, or *Cryptococcus* fungal pathogens when moderate or high levels of anti-Kex protein or peptide antibodies or antigen binding fragments thereof are detected and measured relative to a control. In embodiments of the above methods, the biological sample is blood, plasma, serum, bronchoalveolar lavage, or lymph.

In an embodiment of the above methods, moderate to high levels or titers of specific anti-*Pneumocystis* Kex protein or peptide antibodies or antigen binding fragments thereof in the subject's sample provide protection to the subject from infection and/or disease caused by one or more of the *Pneumocystis, Aspergillus, Candida*, or *Cryptococcus* fungal pathogens. In an embodiment, negative to low antibody titers range from about 1 to about 3200 RET, moderate levels range from about 3200 to about 12,800 reciprocal endpoint antibody titers (RET), and high levels are greater than about 12,800 RET, based on the distribution of anti-*Pneumocystis* KEX1 RET in human samples. In other embodiments of the above methods, the Kex protein or peptide is directly or indirectly coupled to a detectable substance. In another embodiment of the above methods, the anti-Kex protein or peptide antibody or an antigen-binding fragment thereof bound to the Kex protein or peptide is detected by a secondary antibody or an antigen binding fragment thereof that is directly or indirectly coupled to a detectable substance selected from one or more of an enzyme, prosthetic group, fluorescent material, luminescent material, bioluminescent material, radioactive material, positron emitting metal, or a nonradioactive paramagnetic metal ion. In an embodiment of the above methods, the fungal-derived Kex protein or peptide is attached to or immobilized on a solid support. In an embodiment of the above methods, the binding of the anti-Kex protein or peptide antibodies or antigen-binding fragments thereof in the subject's sample to the fungal-derived Kex protein or peptide is detected by an immunoassay. In an embodiment of the methods, a subject who has low, no, or negligible levels of anti-fungal-derived Kex protein or peptide antibodies or antigen binding fragments thereof in her/his sample is treated with an antibody or an antigen binding fragment thereof directed against one or more of *Pneumocystis, Aspergillus, Candida*, or *Cryptococcus* fungal pathogens so as to provide therapeutic protection to the subject against infection and/or disease caused by the one or more fungal pathogens.

In another aspect, the invention provides a method of treating or protecting an immunosuppressed patient against infection by one or more fungal pathogens and/or disease associated with infection by the fungal pathogens, in which the method comprises: administering to a subject who is to receive, is receiving, or has received an immune suppressive drug or medication, a peptide immunogen derived from the Kexin protein of a fungal pathogen, an isolated antiserum comprising antibodies produced against the peptide immunogen, or isolated and purified antibodies produced against the peptide immunogen, wherein the fungal pathogen is selected from one or more of *Pneumocystis, Aspergillus, Candida*, or *Cryptococcus* in an amount effective for the patient to acquire cross-protective immunity against infection and/or disease associated with two or more of the *Pneumocystis, Aspergillus, Candida*, or *Cryptococcus* fungal pathogens. In an embodiment of the method, the patient is a pre-transplant patient or a post-transplant patient. In an embodiment of the method, the patient is to receive or has received an organ transplant selected from a kidney, liver, heart, bone marrow, pancreas, lung, gall bladder, or bladder organ transplant. In an embodiment, of the method, the patient suffers from rheumatoid arthritis or psoriasis. In an embodiment of the method, the patient is receiving or has received one or more immunosuppressive drugs selected from corticosteroids, calcineurin inhibitors, mTOR inhibitors, inosine monophosphate dehydrogenase (IMDH) inhibitors, a biologic or a monoclonal antibody or an antigen binding fragments thereof.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By a "Kex1" or "Kexin" or "KEX" protein is meant a polypeptide or peptide fragment thereof having at least about 85% or greater amino acid identity to the amino acid sequence provided at GenBank Accession No. EU918304.1, at NCBI Accession No. XM_746441.1, at GenBank Accession No. AF022372.1, or at NCBI Accession No. XM_572303.1 and having biological activity as a serine protease. In an embodiment, the Kex peptide is an antigenically stable active site peptide sequence. (Kutty, G. and Kovacs, J. A., 2003, Infect. Immun., 71(1):571-574; Lee. L. H. et al., 2000, Gene, 242(1-2):141-150; and Russian, D. A. et al., 1999, Proc. Assoc. Am. Physicians, 111(4):347-356). An exemplary Kex1 polypeptide fragment of *Pneumocystis* isolated from *Pneumocystis* colonized non-human primates (cynomolgus macaques) and having GenBank Accession No. EU918304.1 is provided below:

```
  1 DDDGKTVDGP SPLVLRAFIN GVNNGRNGLG SIYVFASGNG GIYDDNCNFD GYANSVFTIT
 61 IGGIDKHGKR FAYSEACSSQ LAVTYAGGSA
```

An exemplary polynucleotide sequence encoding the Kex1 polypeptide fragment provided at GenBank Accession No. EU918304.1 is provided below:

```
  1 gatgacgatg gaaaaaccgt tgatgggcct tctcctcttg ttcttagagc atttattaat
 61 ggagtaaata atgggaggaa tgggttgggt tctatctatg tttttgcatc aggaaatggc
121 ggaatatacg atgacaactg taattttgat ggatatgcaa atagcgtgtt tactattact
181 attggtggta tagataaaca cggaaagcgc tttgcatatt ctgaagcgtg ttcttctcag
241 ttagctgtta catatgcagg cggaagtgca
```

An exemplary Kex (KexB endoprotease) polypeptide sequence of *Aspergillus fumigatus* (Af293) having NCBI Accession No. XM_746441.1 is provided below:

```
MRFLGSIALVLSSISVASANVRSRSYDTHEFFALHLDDSASPSHVAQLLGA
RHEGQIGELANHHTFSIPRERSSDLDALLERARAARKIRRRARDDATSQEQ
HNDALGGILWSQKLAPKKRLVKRVPPPERLARTFATGKEDPVAAQSQKRIA
STLGITDPIFNGQWHLFNTVQLGHDLNVTGVWMEGITGKGVTTAVVDDGLD
MYSNDLKPNYFPEGSYDFNDHTPEPRPRLSDDKHGTRCAGEIAAARNDVCG
VGVAYDSRVAGVRILSKAIDDADEATAINFAYQENDIFSCSWGPPDDGATM
EGPGILIKRAFVNGVQNGRGGKGSIFVFAAGNGASFEDNCNFDGYTNSIYS
ITVGAIDREGNHPSYSESCSAQLVVAYSSGSGDAIHTTDVGTDKCYSFHGG
TSAAGPLAAGTVALALSARPELTWRDAQYLMVETAVPIHEDDGSWQVTKAG
RKFSHDWGYGKVDAYALVQKAKTWELVKPQAWFHSPWLRVQHKVPQGDQGL
ASSYEVTEQMMKNANIARLEHVTVTMNVNHTRRGDLSVELRSPEGIVSHLS
```

TTRKSDNEKAGYVDWTFMTVAHWGESGVGRWTVIVKDTNVNEFTGEFIDWR

LNLWGEAIDGANQKPHPFPDEHDDDHSIEDAIVATTSVETGPTKTGVPGST

DDTINRPVNAKPVETQTPSPAETTATKLAPPAETRPAATATSSPTPPAASD

SFLPSFMPTFGASKRTQIWIYAAIGSIIVFCIGLGIYFQVQRRKRILNNPR

DDYDFEMIEDENALHGGNGRSGRTQRRGGELYNAFAGESDEEEPLFSDEDD

EPYRDRAPSEDRLRDTSSDDRSLRHGDH

An exemplary Kex (Kex2 proteinase) polypeptide sequence of *Candida albicans* having GenBank Accession No. AF022372.1 is provided below:

MLPIKLLIFILGYLLSPTLQQYQQIPPRDYENKNYFLVELNTTNSQKPLID

FISHYRGHYNFEHQLSSLDNHYVFSIDKSHPHNSFLGNHNSNEYNLMKRQL

GHEQDYDELISHVESIHLLPMKKLSKRIPVPIEMEDVVFDNRDDTGSDNHE

ATDEAHQKLIEIAKKLDIHDPEFTTQWHLINLKYPGHDVNVTGLWLEDILG

QGIVTALVDDGVDAESDDIKQNFNSEGSWDFNNKGKSPLPRLFDDYHGTRC

AGEIAAVKNDVCGIGVAWKSQVSGIRILSGPITSSDEAEAMVYGLDTNDIY

SCSWGPTDNGKVLSEPDVIVKKAMIKGIQEGRDKKGAIYVFASGNGGRFGD

SCNFDGYTNSIYSITVGAIDYKGLHPQYSEACSAVMVVTYSSGSGEHIHTT

DIKKKCSATHGGTSAAAPLASGIYSLILSANPNLTWRDVQYISVLSATPIN

EEDGNYQTTALNRKYSHKYGYGKTDAYKMVHFAKTWVNVKPQAWYYSDIIE

VNQTITTTPEQKAPSKRDSPQKIIHSSVNVSEKDLKIMNVERVEHITVKVN

IDSTYRGRVGMRIISPTGVISDLATFRVNDASTRGFQNWTFMSVAHWGETG

IGEWKVEVFVDDSKGDQVEINFKDWQFRIFGESIDGDKAEVYDITKDYAAI

RRELLEKEKQNSKSTTTTSSTTTATTTSGGEGDQKTTTSAENKESTTKVDN

SASITTSQTASLTSSNEQHQPTESNSDSDSDTDDENKQEGEEDNDNDNDNG

NKKANSDNTGFYLMSIAVVGFIAVLLVMKFHKTPGSGRRRRRRDGYEFDII

PGEDYSDSDDDEDDSDTRRADDDSFDLGHRNDQRVVSASQQQRQYDRQQDE

ARDRLFDDFNAESLPDYENDMFKIGDEEEEEEEEEGQQSAKAPSNSEGNS

GTSTKK

An exemplary Kex polypeptide sequence of *Cryptococcus neoformans* (JEC21) having NCBI Accession No. XM_572303.1 is provided below:

MRTLLSLWGILLALIVPPSLALQRPQPRSYDTHAYYALELDPSISPAAALQ

LSKSLGVELVERIGELDGHWLVRTEGWTPEHASITKRSVSHDPILKRWEAL

PSSLGKKSLTPLSLKQRAKRHKSYSPRSRHSRDDRTELLYAQNELHLADPM

LDQQWHLINTQMKDIELNVTGLWGRGITGEGVHVVIIDDGLDVESKDLKDN

FFAEGSYDFNDHTELPIPRLKDDQHGTRCAGEIAAVPNDVCGVGVAYDSKI

AGVRILSAPISDADEAAALNYAYQLNDIYSCSWGPPDDGRSMEAPDGLILK

AMVNGVQKGRDGKGSVFVFAAGNGGGSDDQCNFDGYTNSIFSVTVGAVDRK

GLHPYYSEMCAAMMVVAPSSGSGDHIHTTDVGKDKCSHSHGGTSAAAPLAV

GVFALALSVRPDLTWRDIQHLAVRHAVFFNPDDPAWELTAAGRHFSYKYGY

GKLDAGLFVEAAEKWQLVKPQTWYDSPSVYLPTTSPADVTRRQDEAADGPT

SSDEETSNPPPVVEPSGSFITEDGVISTYEVTQSMLFDANFERLEHVTVRV

WIDHQRRGDVEVELTSPNGVVSVLCRQRRFDNADSGFPGWKFMSLKHWDEN

PVGTWTIKVKDQVNPDKTGRFVAWSLQLWGESVDPALAKLWAPAEEGQPDE

EQTGSNPSTTVSQKPKPTALLPGDHGEASGEATQPGLGSATAHPQPTSTTG

DAGNVAEPTGPTDADADEGFFSGISNLASSSTWLAGAGAIIILSGAAIGAF

FFIRARRQKRNLFGLSNNGQGARGAYEPVDDVQMSLLERGRRKFGKSKSES

QGTKDLYDAFGDGPSDEEEEDLDERTALRYHDGFLEDDEPNEVGPKTEYKD

EPESEPETFKDGEETVGTKDKGKGKGPSEGESGSGSSSSWQDAADEEARV

By "agent" is meant a peptide, nucleic acid molecule, or small compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, *Journal of Immunological Methods,* 231:25-38), composed of either a $V_L$ or a $V_H$ domain which exhibit sufficient affinity for the target, and multispecific antibodies formed from antibody fragments. The antibody fragment also includes a human antibody or a humanized antibody or a portion of a human antibody or a humanized antibody.

Antibodies can be made by any of the methods known in the art utilizing a polypeptide (e.g., a Kexin polypeptide), or immunogenic peptide fragments thereof, as an immunogen. One method of obtaining antibodies is to immunize suitable host animals with an immunogen and to follow standard procedures for polyclonal or monoclonal antibody production. The immunogen facilitates the presentation of the immunogenic fragments on the cell surface. Immunization of a suitable host can be carried out in several ways. Nucleic acid sequences encoding a polypeptide of the invention, or immunogenic fragments thereof, can be provided to the host in a delivery vehicle that is taken up by immune cells of the host. The cells will in turn express the receptor on the cell surface generating an immunogenic response in the host.

specific embodiments, the anti-Kexin antibody or anti-Kex1 antibody specifically binds a binding site of a Kexin protein or peptide of a fungal pathogen, for example, one or more of a *Candida, Pneumocystis, Aspergillus* and/or *Cryptococcus* fungal pathogen. In various embodiments, the "anti-Kexin antibody" or "anti-Kex1 antibody" has at least about 85% or greater amino acid identity to a Kex1 peptide amino acid sequence provided below.

```
 1 DDDGKTVDGP SPLVLRAFIN GVNNGRNGLG SIYVFASGNG GIYDDNCNFD GYANSVFTIT
61 IGGIDKHGKR FAYSEACSSQ LAVTYAGGSA
```

Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

By "anti-Kexin antibody," "anti-Kex antibody," or "anti-Kex1 antibody" is meant an antibody or an antigen binding fragment thereof that selectively binds a Kexin polypeptide or a peptide fragment thereof, including, for example, a Kex1 peptide fragment of a fungal pathogen, such as *Candida albicans, Pneumocystis hominis, Pneumocystis jirovecii* (aka *carinii*), *Aspergillus fumigatus* and *Cryptococcus neoformans* as described herein. In various embodiments, anti-Kexin antibody or anti-Kex1 antibody specifically binds a binding site of a Kexin protein or peptide. In An "antiserum" refers to blood serum that contains one or more antibodies directed against a specific antigen. Antiserum containing antibodies may be obtained from the blood or serum of an animal (a mammal), including a human, that has been immunized or inoculated with an immunogen (or an antigen material) either by injection, typically into the bloodstream or tissues, or by infection. In an embodiment, the animal (a mammal), including a human, may be immunized or inoculated with the blood or serum of an organism or individual whose immune system has been stimulated to generate an immune response (e.g., antibody production) by infection or natural contact with an antigenic material or immunogen. In this case, an antiserum contains anti-Kex peptide antibodies, e.g., polyclonal antibodies or populations of monoclonal antibodies, generated or produced by an immunized, inoculated, or exposed donor subject against a Kex peptide immunogen derived from a fungal pathogen, e.g., *Pneumocystis* (e.g., *Pneumocystis jirovecii*). Such antiserum, isolated (and/or purified) from the donor subject is used to immunize (i.e., administer to) another (unrelated) subject so as to provide immunity (acquired immunity) against infection or disease caused by or associated not only with the *Pneumocystis* pathogen as original source of the immunogen, but also with other fungal pathogens that have a Kex peptide that is also targeted and recognized by the antibodies in the antiserum. In embodiments, the fungal pathogens include *Pneumocystis* species (spp.) and one or more of *Candida* spp. or *Candida albicans, Aspergillus* spp. or *Aspergillus fumigatus*, or *Cryptococcus* spp. or *Cryptococcus neoformans*. In this way, a subject who receives the antiserum, i.e., antibodies in the antiserum, is treated or protected against infection and/or disease caused by more than one fungal pathogen. Such antiserum-derived immunoprotection against multiple fungal pathogens constitutes an acquired or passive immunity obtained by the recipient subject and imparted from the donor subject's isolated antiserum. As will be appreciated by one skilled in the art, blood serum is the amber-colored, protein-rich liquid component of blood that separates from the clot when blood coagulates. The serum component containing one or more antibodies (cross-protective antibodies) is termed "antiserum." In an embodiment, the antiserum is an isolated antiserum, e.g., isolated from a donor subject. In an embodiment, an isolated antiserum may be processed by methods used by one skilled in the art, such as dilution, concentration (e.g., via filtration or centrifugation or both), chromatography, purification to remove ions or extraneous protein, and the like, prior to its use as a treatment or protective therapeutic as described herein. In an embodiment, an isolated antiserum may be further purified after isolation. In an embodiment, an isolated antiserum is not further processed or purified. In an embodiment, antibodies, or antigen-binding fragments thereof, contained in an isolated antiserum may be further isolated by methods practiced by those having skill in the art, such as, without limitation, by affinity chromatography, size exclusion chromatography, immunoprecipitation, dialysis, HPLC chromatography, etc.

By "biological sample" is meant any liquid, cell, or tissue obtained from a subject. In some embodiments, the biological sample is blood, serum, plasma, cerebrospinal fluid, bronchoalveolar lavage, sputum, tears, saliva, urine, semen, feces, etc.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte that is detected or that is to be detected.

By "disease" is meant any condition, dysfunction, or disorder that damages or interferes with the normal function of a cell, tissue, or organ. In various embodiments, the disease is a pulmonary (lung) disease or a brain disease, e.g., meningitis. Non-limiting examples of pulmonary diseases include Chronic Obstructive Pulmonary Disease (COPD), which is a progressive lung disease that includes emphysema, chronic bronchitis, severe refractory (non-reversible) asthma, and some forms of bronchiectasis.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. An immunologically effective amount of an isolated antiserum of the invention is an amount required to treat a fungal infection or disease associated with one or more of the fungal pathogens described herein. By way of example, an effective amount of an isolated antiserum may be determined by measuring the amount or titer of antibodies directed against the desired immunogen present in the serum by methods known and practiced in the art. The range of typical dosages for passive immunotherapy (i.e., the administration of antiserum containing antibodies) includes about 0.3 mg to about 100 mg/kg of total body weight. Following passive immunotherapy, treatment efficacy is typically conducted, as individual patients respond differently to therapies. Adjustment of the dosage may be modified as needed. Treatment regimens can be determined by methods known and practiced by those having skill in the art.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state or environment. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" or "isolated peptide" is meant a polypeptide or peptide that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, "obtaining" as in "obtaining an agent" includes synthesizing, purchasing, or otherwise acquiring the agent.

By "reduces" or "diminishes' is meant a negative alteration of at least 10%, 25%, 50%, 75%, or 100%.

By "reference" is meant a standard or control condition. A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody or antigen binding fragment thereof that recognizes and binds a polypeptide or peptide, but which does not substantially recognize and bind other molecules in a sample, for example, a biological sample, which naturally includes a polypeptide of the invention. Cross-reactive binding includes specific binding (e.g., by an antibody or an antigen binding fragment thereof) to an original polypeptide or peptide antigen/immunogen as well as binding to a polypeptide or peptide other than the original antigen/immunogen.

Nucleic acid molecules useful in generating a recombinant immunogen or a vaccine include any nucleic acid molecule that encodes a polypeptide or a peptide fragment thereof, such as a Kex polypeptide or Kex peptide described herein. Such nucleic acid molecules need not be 100% identical with an endogenous nucleic acid sequence, but will typically exhibit substantial identity to an endogenous sequence. Polynucleotides having "substantial identity" to an endogenous sequence are typically capable of hybridizing with at least one strand of a double-stranded nucleic acid molecule. Nucleic acid molecules may include any nucleic acid molecule that encodes a polypeptide or a peptide fragment thereof. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a non-human primate, or a murine, bovine, equine, canine, ovine, or feline mammal. In an embodiment, the subject is a human. In an embodiment, a subject is a human patient who is undergoing treatment for infection or disease caused by one or more pathogenic fungi, such as *Pneumocystis, Aspergillus, Candida*, or *Cryptococcus*. In an embodiment as subject is a human patient who is at risk of infection (e.g., opportunistic infection) or disease caused by one or more pathogenic fungi, such as *Pneumocystis, Aspergillus, Candida*, or *Cryptococcus*. In an embodiment, a subject is a mammalian (e.g., a human; a non-human primate) donor subject from whom antiserum containing anti-fungal Kex peptide antibodies is obtained or isolated. In an embodiment, a subject is a mammalian (e.g., a human; a non-human primate) recipient subject who receives an isolated antiserum and acquires protective immunity (and treatment) against multiple fungal pathogens.

By "opportunistic infection" is meant an infection caused by pathogens such as fungal pathogens, bacteria, viruses, protozoa, or parasites that take advantage of an opportunity to infect a subject (host) that is not normally available, for example, a host having a weakened immune system, an immunocompromised host, a host with altered microbiota or microflora, or a host having protective integumentary barriers that have been damaged or breached. In an embodiment, an opportunistic infection is caused by one or more fungal pathogens as described herein.

As used herein, "PS-15" refers to a dihydrofolate reductase inhibitor having the following structure:

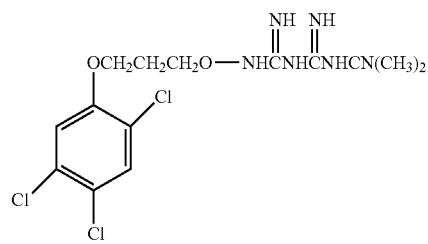

"QS-21" refers to an adjuvant having the following structure:

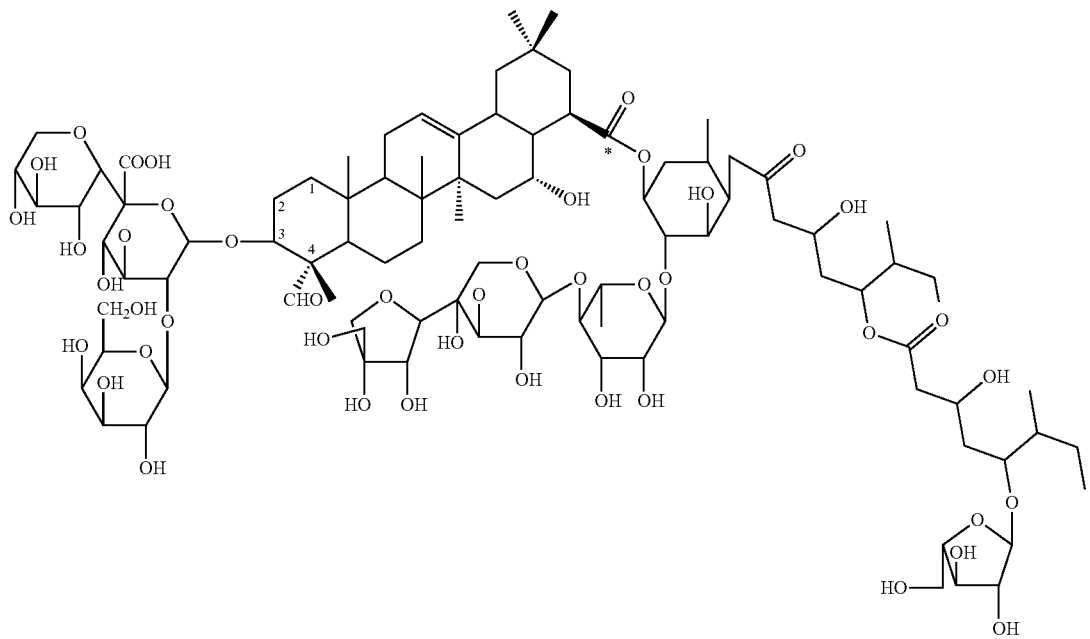

Soltysik et al., Structure/Function Studies of QS-21 Adjuvant: Assessment of Triterpene Aldehyde and Glucuronic Acid Roles in Adjuvant Function, Vaccine, 13(15): 1403-1410 (1995).

Ranges provided herein are understood to be shorthand for all the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing, abating, diminishing, or ameliorating a disease, disorder and/or symptoms associated therewith. It will be appreciated that, although not precluded, treating a disease, disorder and/or symptoms associated therewith does not require that the disease, disorder, condition or symptoms associated therewith be completely eliminated.

As used herein, a therapeutic that "prevents" a disorder or condition refers to a compound or material that, in a statistical sample, reduces the occurrence of the disorder or condition in the treated sample relative to an untreated control sample, or delays the onset or reduces the severity of one or more symptoms of the disorder or condition relative to an untreated control sample. In an embodiment, a preventive therapeutic is an antibody or an antigen binding fragment thereof. In a particular embodiment, a preventive therapeutic is an isolated antiserum containing anti-Kex peptide antibodies or antigen binding fragments thereof as described herein.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

BRIEF DESCRIPTION OF THE DRAWINGS

Exemplary embodiments of the present invention are provided below as drawings and figures related to the description of the invention in its various and nonlimiting aspects.

FIGS. 1A and 1B present a multiple amino acid sequence alignments and phylogenetic tree data related to several Kexin proteins from the fungal pathogens described herein. FIG. 1A provides a multiple sequence alignment comparing a 90-amino acid region of the subtilisin-like serine protease Kexin (KEX1 or KEX) derived from *Pneumocystis jirovecii* (*P. jirovecii* KEX1 (SEQ ID NO: 8)); *Pneumocystis macaque* (*P. macaque* KEX1 (SEQ ID NO: 9)); *Aspergillus fumigatus* (*Aspergillus* KEX (SEQ ID NO: 10)); *Cryptococcus neoformans* (*Cryptococcus* KEX (SEQ ID NO: 11)); and *Candida albicans* (*Candida* KEX (SEQ ID NO: 12)). The *P. macaque* KEX1 sequence is referenced in Accession No. EU918304.1. The Legend in FIG. 1A describes the differences or similarities of the amino acid residues in different positions in the alignments. In particular, the "*" (asterisk) indicates positions that have a single, fully conserved residue; the ":" (colon) indicates conservation between groups of strongly similar properties as shown in the phylogenetic tree of FIG. 1B, roughly equivalent to scoring >0.5 in the Gonnet PAM 250 matrix; and the "." (period) indicates conservation between groups of weakly similar properties as shown in the phylogenetic tree of FIG. 1B, roughly equivalent to scoring:=:<0.5 and >0 in the Gonnet PAM 250 matrix. FIG. 1B depicts phylogenic genetic tree data comparing the KEX peptides of *Pneumocystis* and other fungal pathogens reflected in FIG. 1A.

FIG. 2 presents a multiple sequence alignment analysis of Kexin (KEX1, KEX) peptide identity and similarity.

FIG. 3 illustrates the sequences of KEX1 peptides from *Pneumocystis, Aspergillus, Candida*, and *Cryptococcus* contained in expression constructs expressed in *E. coli* (i.e., recombinant fungal KEX1 homologs as expressed in *E. coli*). In the figure, the highlighted regions are the sequences expressed by the expression constructs. *Pneumocystis* KEX1 and homologous regions are shown. In FIG. 3 (1.), aPneumocystis Kex1 conserved 90 amino acid sequence used in an expression construct is shown (SEQ ID NO: 8); in FIG. 3 (2.), a 90 amino acid macaque *Pneumocystis* Kex1 conserved sequence used in an expression construct is shown (SEQ ID NO: 9); in FIG. 3 (3.), a conserved 90 amino acid *Aspergillus* Kex sequence is shown SEQ ID NO: 10); and an 88 amino acid *Aspergillus* Kex1 sequence used in an expression construct (designated AF_Kex.DS88) is shown (SEQ ID NO: 13); in FIG. 3 (4.), a conserved 90 amino acid *Candida* Kex sequence is shown (SEQ ID NO: 12); and an 88 amino acid *Candida* Kex sequence used in an expression construct (designated CA_Kex.DS88) is shown (SEQ ID NO: 14). In FIG. 3 (5.) a conserved 90 amino acid *Cryptococcus* Kex sequence is shown (SEQ ID NO: 11); and a *Cryptococcus* Kex expression construct (designated CN_Kex.DG117) containing 117 amino acid residues is shown (SEQ ID NO: 15). The CN_Kex.DG117 construct shown in FIG. 3 (5.) contained a polynucleotide encoding a 117-amino acid sequence, which included an additional 28 amino acids downstream as shown (DHIHTTDVGKDKCSHSHGGTSAAAPLAV, (SEQ ID NO: 6)).

In FIG. 4A, the presence of MBP tagged proteins was confirmed by blotting with mouse anti-MBP antibody (1:10,000) (New England BioLabs) and goat anti-mouse IgG (H+L)-HRP secondary antibody (1:10,000) (ThermoFisher). To determine if anti-sera from *Pneumocystis* KEX1 immunized monkeys cross reacted with *Candida* KEX, membranes were incubated with high titer sera from vaccinated monkey 17911 (dilution 1:500), shown in FIG. 4B, or with low titer sera from unvaccinated monkey 8015 (dilution 1:500), shown in FIG. 4C, for 2 hours at room temperature. Blots were then incubated with goat anti-monkey IgG (H+L)-HRP secondary antibody (1:10,000) in blocking buffer for 1 hour at room temperature and were visualized with SuperSignal West Pico Chemiluminescent Substrate (ThermoFisher). As a negative control, parallel blots were probed with secondary antibody only, shown in FIG. 4D.

FIG. 6A shows Western blots showing that *Aspergillus* KEX is recognized by the immune system during *Aspergillus* infection in animals in vivo and at low levels in uninfected animals. The animals produce anti-*Aspergillus* antibodies during *Aspergillus* infection. Recombinant *Aspergillus* KEX-MBP and TEV-cleaved *Aspergillus* KEX (*Aspergillus* KEX-MBP+TEV) proteins were resolved by 15% SDS-PAGE and immunoblotting was performed as described for FIGS. 4A-D above. To determine if *Aspergillus* KEX peptide behaved as an immunogen and was detected by an animal's immune system during a natural infection with *Aspergillus*, membranes were blotted with sera obtained from an *Aspergillus*-infected mouse (Top Panel), or with sera from an uninfected mouse (Bottom Panel) at the dilutions indicated above the lanes at the top of the blots, i.e., 1 to 50 (1:50); 1 to 100 (1:100); and 1 to 200 (1:200). The blots were then incubated with goat anti-mouse IgG (H+L)-HRP secondary antibody (1:10,000) (ThermoFisher) and were visualized with SuperSignal West Pico Chemiluminescent Substrate (ThermoFisher). FIG. 6B presents a Western blot showing that antisera generated during *Aspergillus* infection is immunologically cross-reactive with recombinant KEX proteins of *Cryptococcus, Candida* and *Pneumocystis*. Recombinant KEX-MBP proteins and TEV-cleaved KEX proteins were resolved by 15% SDS-PAGE and immunoblotting was performed as described for FIGS. 4A-D above. To determine if KEX antibodies generated during *Aspergillus* infection in an animal immunologically cross reacted with fungal KEX peptides, membranes were blotted with sera from an *Aspergillus*-infected mouse at the dilution of 1:500. The blots were then incubated with goat anti-mouse IgG (H+L)-HRP secondary antibody (1:10,000) (ThermoFisher) and were visualized with SuperSignal West Pico Chemiluminescent Substrate (ThermoFisher). Recombinant proteins on the blot were expressed as fusions with maltose binding protein (MBP) cleaved with TEV protease to release fungal peptides, namely, *Cryptococcus* KEX, *Aspergillus* KEX, *Candida* KEX, and *Pneumocystis* KEX1. The binding of antibodies in *Aspergillus*-infected mouse serum to specific fungal Kex peptides on the blots is indicated by an *.

FIG. 7A depicts an ELISA analysis template in which vertical dilutions are made using 10 test samples and 1 control on the microtiter plate. FIG. 7B depicts an ELISA analysis template in which horizontal dilutions are made using 6 test samples and 1 control on the plate.

DETAILED DESCRIPTION OF THE INVENTION

Figure 1B:
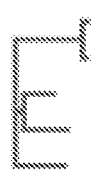
Figure 4A:
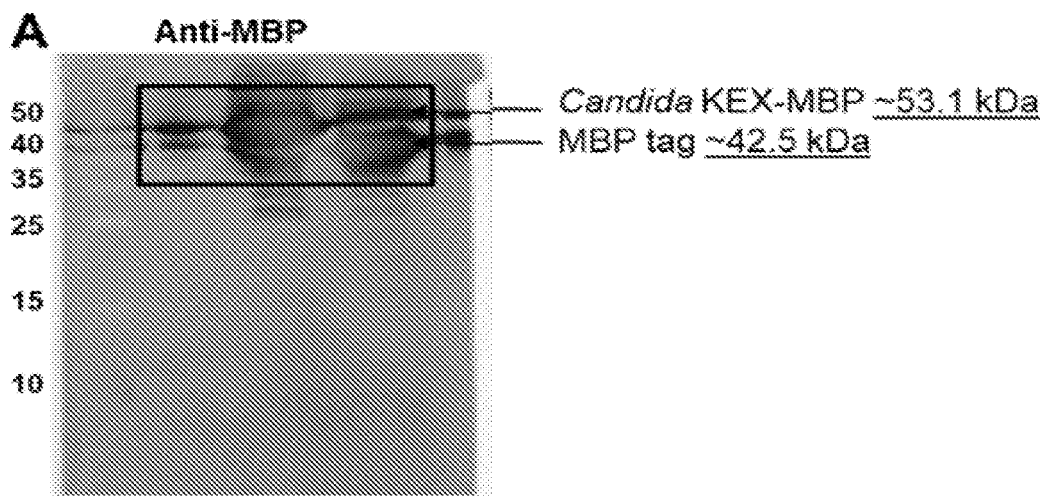
FIGS. 4A-4D present Western blots which show that the *Candida* Kex recombinant protein is recognized by (immunologically cross-reactive with) sera (antisera containing antibodies) from monkeys (macaques) immunized with *Pneumocystis* KEX1 (*P. macaque*, Accession No. EU918304.1). An 88-amino acid *Candida* KEX peptide (FIGS. 1A and 3) containing an N-terminal tobacco etch virus (TEV) cleavage site and a maltose binding protein (MBP) tag (*Candida* KEX-MBP) was recombinantly expressed and affinity purified. (See, Example 2). The purified recombinant protein was then incubated with TEV protease to cleave the N-terminal MBP affinity tag (*Candida* KEX-MBP+TEV). Recombinant proteins were resolved by 15% SDS-PAGE and transferred to 0.2 µm nitrocellulose membranes. Membranes were then blocked overnight at 4° C. in 5% BSA/5% non-fat dry milk in PBS-T (0.05% Tween-20). A 6×-His tagged *Pneumocystis* KEX1 ("6s-His" disclosed as SEQ ID NO: 7) was included as a positive control.
Figure 4B:
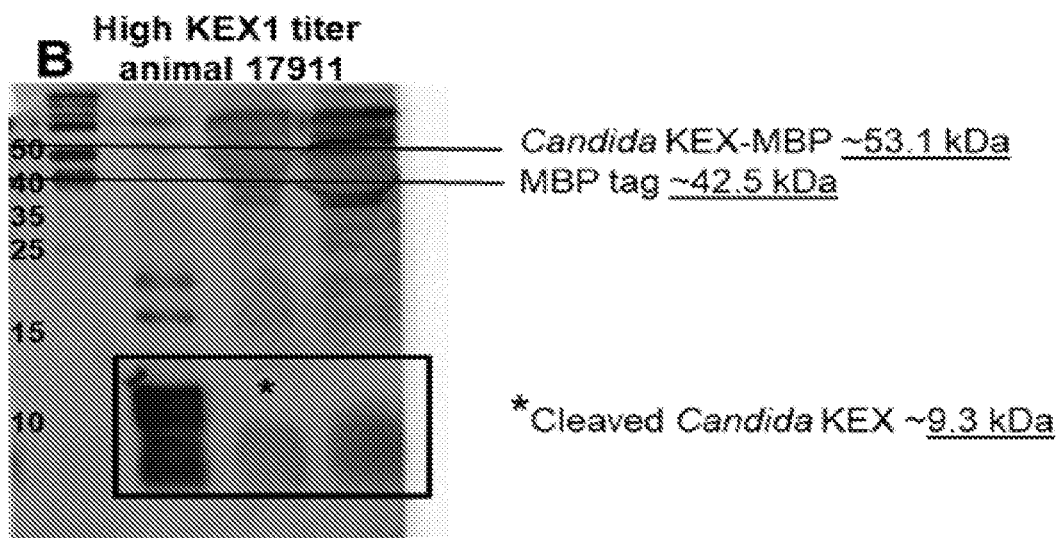
Figure 4C:
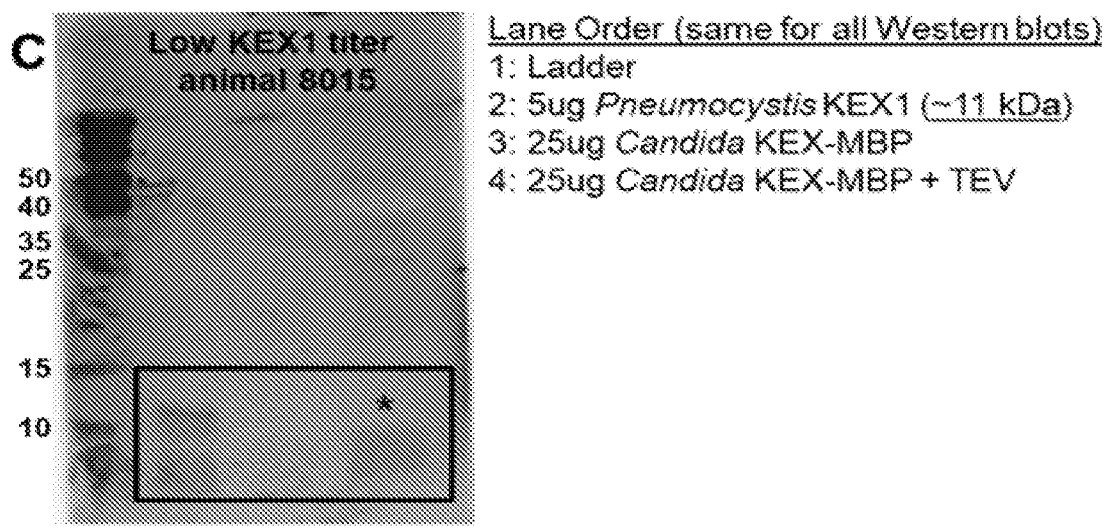
Figure 4D:
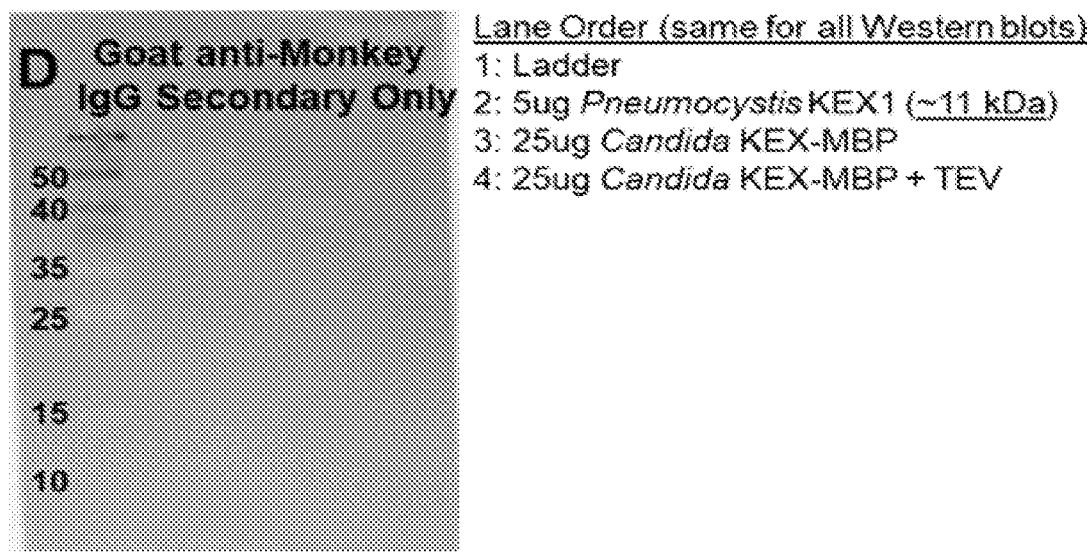
Figure 5A:
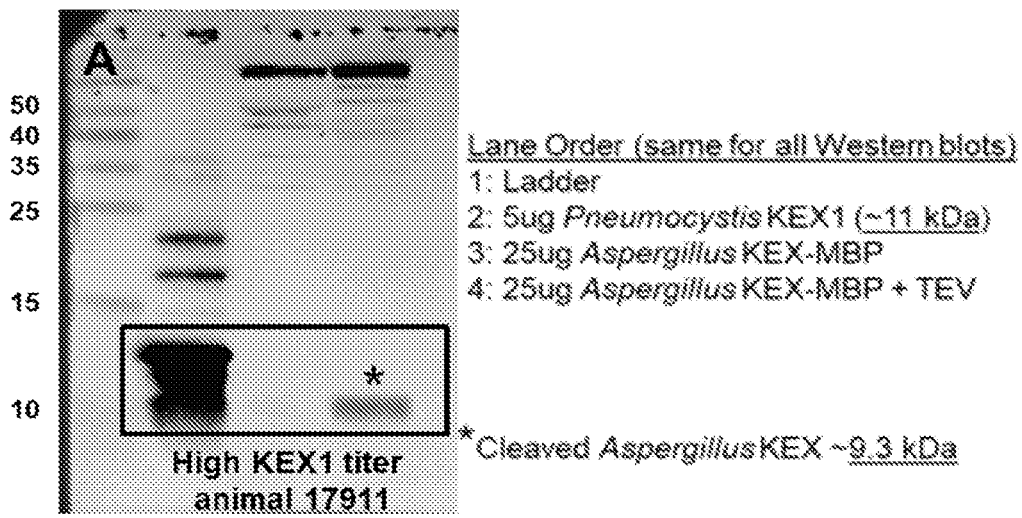
FIGS. 5A-5D present Western blots which demonstrate that the *Aspergillus* Kex recombinant protein is recognized by sera from monkeys (macaques) immunized with *Pneumocystis* KEX1 (*P. macaque*, Accession No EU918304.1). Accordingly, the *Aspergillus* Kex recombinant protein is immunologically cross-reactive with *Pneumocystis* Kex1 antibodies in the antiserum. An 88-amino acid long *Aspergillus* KEX peptide (FIGS. 1A and 3) containing an N-terminal TEV cleavage side and maltose binding protein (MBP) tag (*Aspergillus* KEX-MBP) was recombinantly expressed and affinity purified. (See, Example 2). The purified recombinant protein was then incubated with TEV protease to cleave the N-terminal MBP affinity tag (*Aspergillus* KEX-MBP+TEV). Recombinant proteins were resolved by 15% SDS-PAGE and immunoblotting was performed as described in FIGS. 4A-D. To determine if antisera from *Pneumocystis* KEX1 immunized monkeys cross reacted with *Aspergillus* KEX, membranes were blotted with high titer sera from vaccinated monkey 17911 (dilution 1:500), shown in FIG. 5A, or with low titer sera from unvaccinated monkey 8015 (dilution 1:500), shown in FIG. 5B, for 2 hours at room temperature. The presence of MBP tagged proteins was confirmed by immunoblotting with mouse anti-MBP antibody, shown in FIG. 5C. As a negative control, parallel blots were probed with secondary antibody only, as shown in FIG. 5D.
Figure 5B:
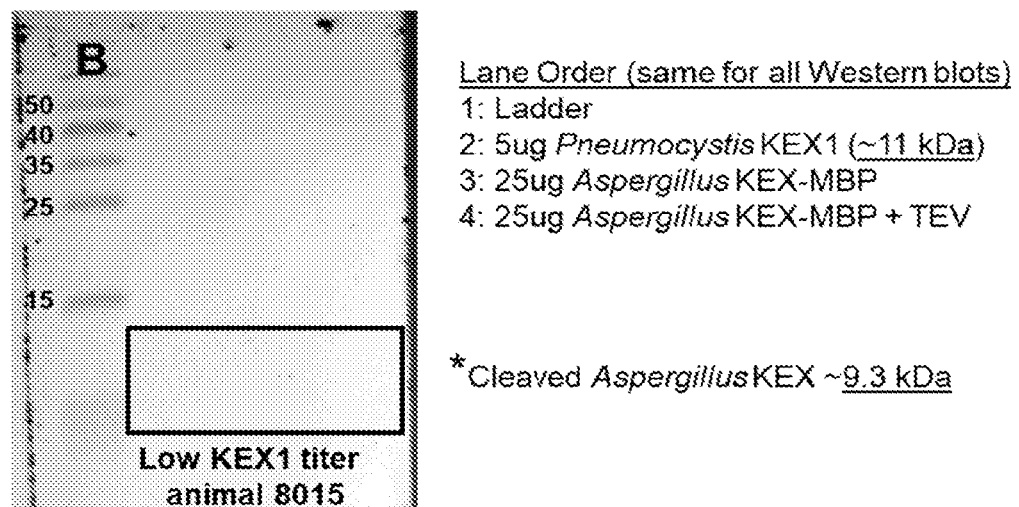
Figure 5C:
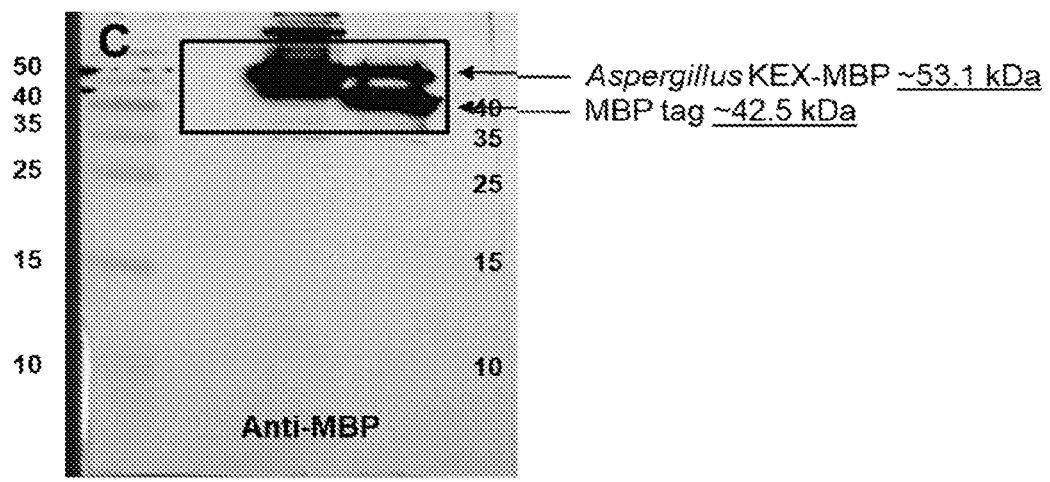
Figure 5D:
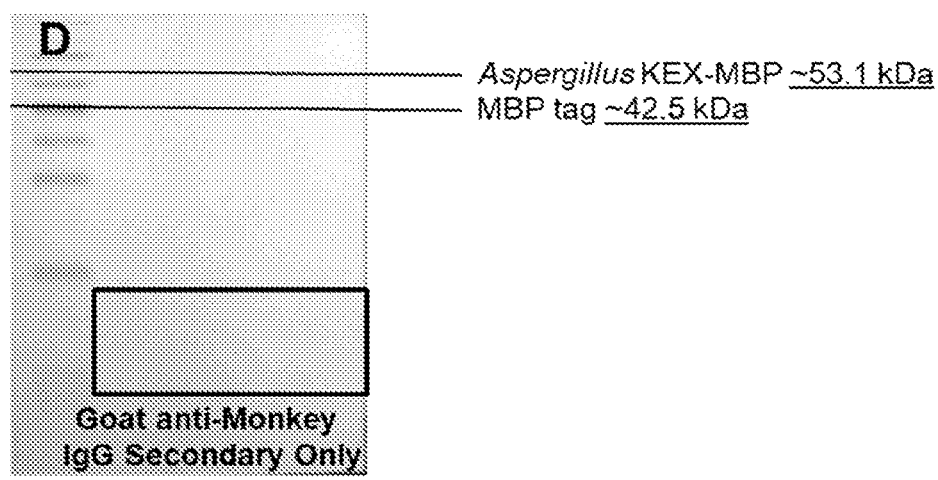

The invention generally provides methods for treating or preventing infection by one or more fungal pathogens, or disease associated with infection by more than one fungal pathogen, in which the fungal organisms are of different etiologies. The invention embraces an immunogenic composition that elicits a potent immune response in a subject following administration of the composition and the production of antiserum in the subject that contains one or more antibodies or antigen binding fragments thereof that reacts not only with the immunizing antigen, but also with a similar, but nonidentical, antigen found in other, distinct fungal pathogens.

One benefit of the described methods is the provision of treatment or prevention of infection by and disease associated with several different fungal pathogens using only one therapeutic agent, i.e., an antiserum (isolated antiserum), that cross-protects against multiple fungal organisms and treats or prevents diseases and symptoms thereof, for example, pulmonary disease and poor pulmonary performance, associated with infection (and colonization) by the different fungal pathogens, e.g., at least two or more fungal pathogens.

In an embodiment, the different fungal pathogens include *Pneumocystis, Aspergillus, Candida,* and *Cryptococcus,* particularly, at least two or more thereof. In a particular embodiment, an antiserum produced in a subject immunized with a Kex peptide derived from *Pneumocystis* (*Pneumocystis jirovecii*) contains antibodies that also specifically react with a Kex peptide derived from one or more of *Aspergillus* (*Aspergillus fumigatus*), *Candida* (*Candida albicans*), or *Cryptococcus* (*Cryptococcus neoformans*). Accordingly, the antiserum is cross-protective (e.g., cross-reactive with Kex peptides in multiple fungal types) and affords treatment and/or protection against infection and/or disease associated with multiple fungal organisms when provided to another (e.g., unrelated) subject in need thereof. In an embodiment, the antiserum is an isolated antiserum. In an embodiment, the isolated antiserum is administered in a pharmaceutically acceptable composition.

The methods and compositions described herein offer economic, medical and practical benefits in the treatment and prevention of fungal infection and disease, such as pulmonary disease, or types of brain infections, associated with infection and colonization by different types of fungal pathogens. The immunogen or immunogenic composition comprising a *Pneumocystis*-derived Kex peptide described herein generated specific antiserum against *Pneumocystis* Kex peptide; this antiserum was surprisingly found to react specifically against Kex peptides of one or more other fungal pathogens, e.g., one or more of *Aspergillus* (*Aspergillus fumigatus*), *Candida* (*Candida albicans*), or *Cryptococcus* (*Cryptococcus neoformans*), (FIGS. 5A-5D and FIGS. 6A-6D), despite non-identity and sequence diversity among the Kex peptides of these other fungal organisms at the amino acid level. (FIG. 3). Thus, the described methods involve the use of antiserum (e.g., an isolated antiserum) that can provide to a subject to whom the antiserum is administered immunity against infection and disease associated with more than one fungal organism. In an embodiment, the recipient subject is infected or is at risk of becoming infected with more than one disease-causing fungal pathogen, namely, *Pneumocystis, Aspergillus, Candida* and *Cryptococcus,* and, in particular, *Pneumocystis hominis* or *jirovecii, Aspergillus fumigatus, Candida albicans,* or *Cryptococcus neoformans.* In an embodiment, the antiserum is an isolated antiserum. In an embodiment, the isolated antiserum is in, or is Therapeutic Methods The methods and compositions provided herein can be used to treat or prevent infection and/or associated disease caused by the fungal pathogens *Pneumocystis, Aspergillus, Candida* and *Cryptococcus,* and, in particular, *Pneumocystis hominis* or *jirovecii, Aspergillus fumigatus, Candida albicans,* or *Cryptococcus neoformans.* The methods and compositions provided herein can provide immune protection in a subject against infection and disease caused by at least one, and particularly more than one, of these fungal organisms. The methods and compositions provided herein can immunize a recipient subject against infection by at least one and particularly by more than one of these fungal organisms. In general, isolated antiserum containing one or more antibodies generated against a Kex peptide of *Pneumocystis,* or of *Aspergillus, Candida,* or *Cryptococcus* fungal organisms can be administered therapeutically and/or prophylactically to provide immunity against other pathogenic fungal organisms that express a Kex protein or peptide antigen. The methods include administering an immunologically effective amount of an isolated antiserum, or immune serum or immune plasma, described herein to an individual, alone, or in a physiologically acceptable carrier, excipient, or diluent. In certain embodiments, antiserum from a subject infected with one of *Pneumocystis, Aspergillus, Candida,* or *Cryptococcus,* more specifically, *Pneumocystis, Aspergillus, Candida,* or *Cryptococcus* fungi, or antiserum obtained or isolated from an immune survivor of infection by one of these fungal pathogens, is used to treat or prevent the infection by another or different type or species of fungal pathogen as described herein. In an embodiment, the isolated antiserum is in a pharmaceutically acceptable composition.

The present invention provides methods of treating or preventing an infection by one or more fungal pathogens (e.g., one or more of *Pneumocystis, Aspergillus, Candida,* or *Cryptococcus,* more specifically, *Pneumocystis hominis* or *jirovecii, Aspergillus fumigatus, Candida albicans,* or *Cryptococcus neoformans* fungi), and/or diseases, disorders, or symptoms thereof, which comprise administering a therapeutically effective amount of an isolated antiserum as described herein to a recipient subject (e.g., a mammal such as a human patient) in need thereof. In an embodiment, the antiserum contains antibodies that specifically target the Kexin protein or a Kex peptide thereof to neutralize the activity of Kex proteinase. In an embodiment, the isolated antiserum allows the recipient subject to achieve and passively acquire protective immunity against multiple fungal pathogens.

In an embodiment, a method of the invention involves treating a subject suffering from or susceptible to an infection by *Pneumocystis, Aspergillus, Candida*, or *Cryptococcus*, or disease or symptom thereof caused by one or more of these fungal pathogens (e.g., pulmonary disease or COPD). The method includes the step of administering to the subject (e.g., a mammal or human patient) a therapeutically effective amount of an isolated antiserum generated against a Kex peptide of one type of fungal organism that is sufficient to treat an infection, disease, disorder, or symptom thereof, caused by one or more different types of fungal organism under conditions such that the infection, disease, disorder, or symptom thereof, is treated. In an embodiment, the isolated antiserum is in a pharmaceutically acceptable composition.

The present invention also provides methods of treating or preventing infection by more than one type of fungal pathogen, and/or diseases or disorders or symptoms thereof, which comprise administering a therapeutically effective amount of an isolated antiserum as described herein (e.g., comprising one or more antibodies or an antigen binding fragment thereof), to a subject (e.g., a mammal such as a human). In various embodiments, the method prevents infection by more than one fungal pathogen selected from *Pneumocystis, Aspergillus, Candida*, or *Cryptococcus* in a subject susceptible to infection, disease, or symptom thereof (e.g., COPD, lung/pulmonary disease, poor pulmonary function, asthma, including severe asthma, or symptoms thereof). In an embodiment, the method includes the step of administering to a recipient mammal a therapeutically effective amount of an isolated antiserum sufficient to treat the infection, disease, disorder, or symptom thereof, under conditions such that the infection, disease, disorder, or symptom thereof is treated. In an embodiment, the method includes the step of administering to a recipient mammal a prophylactic or preventive amount of an antiserum sufficient to prevent the infection, disease, disorder, or symptom thereof, under conditions such that the infection, disease, disorder, or symptom thereof is prevented. In an embodiment, the isolated antiserum is in a pharmaceutically acceptable composition. In an embodiment, the recipient mammal is a human patient in need of treatment.

Treatment will be suitably administered to subjects, particularly humans, suffering from, having, susceptible to, or at risk for infection by, more than one fungal organism, in particular, more than one of *Pneumocystis, Aspergillus, Candida*, or *Cryptococcus*, and in particular, *Pneumocystis hominis* or *jirovecii, Aspergillus fumigatus, Candida albicans*, or *Cryptococcus neoformans*, or a disease, pathogenic condition, or symptom thereof. Determination of those subjects who are "at risk" can be made by any objective or subjective determination by a diagnostic test or opinion of a subject or health care provider (e.g., genetic test, enzyme test or assay, or protein marker (such as levels of anti-Kex antibodies, e.g., in serum), family history, and the like). The methods herein also include administering to the recipient subject (including a subject identified as in need of such treatment or as being at risk of infection) an effective amount of an anti-fungal pathogen antiserum isolated from a donor subject as described herein. Identifying a subject in need of such treatment can involve the judgment of the recipient subject or a health care or medical professional and can be subjective (e.g., opinion) or objective (e.g., measurable by a test or diagnostic method). In an embodiment, the isolated antiserum is provided in a pharmaceutically acceptable composition.

In some aspects, the invention features methods of treating or preventing a fungal infection or fungal pathogen-associated disease or condition (e.g., pulmonary infection, pulmonary disease or disorder, pneumonia, COPD, asthma including severe asthma, and the like) in a subject, the methods comprising administering to a subject in need thereof an effective amount of an isolated antiserum obtained from an individual who has produced an antibody immune response against a fungal Kexin protein or immunogenic peptide thereof as described herein, such that the subject is therapeutically and/or prophylactically treated against infection or disease associated with a different fungal pathogen.

In an embodiment, the invention provides methods of treating or preventing fungal infection and/or disease in a patient who is receiving or who has received immune suppressive drugs or medication and who, as a result of drug-induced immune system suppression, is susceptible to or may become susceptible to (or at risk of) infection by a pathogenic fungus, such as one or more of the *Pneumocystis, Aspergillus, Candida*, or *Cryptococcus* fungal pathogens, either in or outside of a nosocomial environment. By way of example, such a patient may be preparing to undergo a transplant (a pre-transplant patient) or may have received a transplant (a post-transplant patient) and is administered one or more immunosuppressive drugs or medications (anti-rejection medications) and/or is otherwise treated with drugs to reduce the likelihood of rejection of the transplanted organ or tissue, thereby making the patient more vulnerable, susceptible to, or at risk of infection and/or disease caused by one or more of the *Pneumocystis, Aspergillus, Candida*, or *Cryptococcus* fungal pathogens. Patients having other types of diseases and conditions, such as rheumatoid arthritis or psoriasis, and the like, may also be administered medications having an immune suppressive effect to treat or manage their conditions and thus suffer from, or be at risk of, infection by one or more fungal pathogens. Non-limiting classes of immune suppressive drugs and medications include, for example, corticosteroids, such as prednisone (e.g., DELATSONE, ORASONE); budesonide (ENTOCORT EC), or prednisolone (MLLIPRED) calcineurin inhibitors, such as cyclosporine (NEORAL, SANDIMMUNE, SANGCYA); or tacrolimus (ASTAGRAF XL, ENVARSUS XR, PROGRAF); mTOR inhibitors, such as sirolimus (RAPAMUNE), everolimus (AFINITOR, ZORTRESS); Inosine Monophosphate Dehydrogenase (IMDH) inhibitors, such as azathioprine (AZASAN, IMURAN), leflunomide (ARAVA), mycophenolate (CELLCEPT, MYFORTIC); Biologics and monoclonal antibodies or monoclonal antibody-based antibodies or antigen binding fragments thereof, such as abatacept (ORENCIA); adalimumab (HUMIRA); anakinra (KINERET); certolizumab (CIMZIA); etanercept (ENBREL); golimumab (SIMPONI); infliximab (REMICADE); ixekizumab (TALTZ); natalizumab (TYSABRI); rituximab (RITIXAN); secukinumab (COSENTYX); tocilizumab (ACTEMRA); ustekinumab (STELARA); and vedolizumab (ENTYVIO). In an embodiment, the patient is to receive or has received a transplant of an organ selected from kidney, liver, heart, bone marrow, pancreas, lung, gall bladder, bladder, etc. Antibodies directed against the Kex peptides of at least one, or at least two of the *Pneumocystis, Aspergillus, Candida*, or *Cryptococcus* fungal pathogens (or antiserum containing such antibodies) can be administered to the patient who is receiving transplant anti-rejection medication, or other immune suppressive medication, in an effective amount to heighten the immune response against infection by one or more, two or more, three or more, or all four of these fungal pathogens in the immune suppressed patient. In an embodiment, the patient receiving immune suppressing drugs can be evaluated and monitored during treatment with immune suppressive drugs for the presence of antibodies (and antibody titers) against one or more of the fungal pathogens by employing the methods and kits as described herein.

Optionally, an isolated antiserum of the invention (e.g., antiserum comprising an anti-*Pneumococcus* Kexin polypeptide or peptide antibody or an antigen binding fragment thereof as described herein) may be administered in combination with one or more of any other treatment or therapy, e.g., anti-fungal therapies. For example, an isolated antiserum or immune plasma containing anti-*Pneumocystis* Kex peptide (or anti-*Aspergillus, Candida*, or *Cryptococcus* Kex peptide) antibody or an antigen binding fragment thereof as described herein may be administered in combination with other antibodies or antibody cocktails with anti-fungal activity (including, for example, immune plasma), or in combination with one or more drugs, for examples, one or more drugs having anti-fungal activity (e.g., trimethoprim-sulfamethoxazole, azithromycin-sulfamethoxazole, clarithromycin-sulfamethoxazole, atovaquone, sulfadoxine-pyrimethamine, erythromycin-sulfisoxazole, PS-15, and dapsone-trimethoprim, as well as intravenous pentamidine and clindamycin-primaquine), to provide protective immunity in the recipient not only against *Pneumocystis*, but also against *Aspergillus, Candida*, or *Cryptococcus* fungal organisms. In an embodiment, an isolated antiserum or immune plasma containing anti-*Aspergillus* Kexin polypeptide or peptide antibody as described herein may be administered in combination with other antibodies or antibody cocktails with anti-fungal activity (including, for example, immune plasma), or in combination with a drug with anti-fungal activity as described above to provide protective immunity not only against *Aspergillus*, but also against *Pneumocystis, Candida*, or *Cryptococcus* fungal organisms in the subject. In an embodiment, an isolated antiserum or immune plasma containing anti-*Candida* Kexin polypeptide or peptide antibody as described herein may be administered in combination with other antibodies or antibody cocktails with anti-fungal activity (including, for example, immune plasma), or in combination with a drug with anti-fungal activity as described above to provide protective immunity not only against *Candida*, but also against *Pneumocystis, Aspergillus*, or *Cryptococcus* fungal organisms in the subject. In an embodiment, an isolated antiserum or immune plasma containing anti-*Cryptococcus* Kexin polypeptide or peptide antibody as described herein may be administered in combination with other antibodies or antibody cocktails with anti-fungal activity (including, for example, immune plasma), or in combination with a drug with anti-fungal activity as described above to provide protective immunity not only against *Cryptococcus*, but also against *Pneumocystis, Candida*, or *Aspergillus* fungal organisms in the subject. In an embodiment of any of the foregoing, the isolated antiserum is provided in a pharmaceutically acceptable composition.

In an embodiment of any of the foregoing aspects, the antiserum isolated from a donor subject immunized, inoculated, or exposed to a *Pneumocystis, Aspergillus, Candida*, or *Cryptococcus* fungal pathogen, e.g., a Kex peptide expressed by such fungal pathogens) allows the recipient subject to acquire immune protection, including memory immune protection, against infection or disease caused by more than one of these fungal pathogens. Methods for administering both single and combination therapies (e.g., concurrently or otherwise) are known to those skilled in the art and are described, for example, in Remington's Pharmaceutical Sciences, 12$^{th}$ edition, Edited by E. W. Martin, Mack Publishing Co. In an embodiment, the antiserum provides a therapeutic, antibody-containing composition that treats infection or disease caused by one or more fungal pathogens as described herein. In another embodiment, the antiserum provides prophylactic, antibody-containing composition that prevents and protects against infection or disease caused by one or more fungal pathogens as described herein. In an embodiment, the isolated antiserum is in a pharmaceutically acceptable composition.

Additional Methods

At present, there is a dearth of methods as well as reagents to determine if a patient who is asymptomatic for infection by one or more, two or more, three or more, or each of *Pneumocystis, Aspergillus, Candida*, or *Cryptococcus* fungal pathogens is susceptible, vulnerable, or at risk for infection by one or more of these pathogens. It is currently difficult to plate out these fungal organisms as they may be present in very low amounts, or they do not grow under the culture conditions available for assessing their presence in a subject. Consequently, it is difficult for a medical practitioner and the patient to know whether the patient is infected with one or more of *Pneumocystis, Aspergillus, Candida*, or *Cryptococcus*, or if they are likely to become infected, for example, after a medical procedure, surgery, or transplant.

It is also difficult to identify, qualify, or stratify patients who are or may be susceptible to infection by one or more fungal pathogen and to monitor patients for changes in susceptibility over time, e.g., during recovery from surgery or during immunosuppressive therapies, for example, following organ transplantation, or during other chemotherapy treatments, or for reduction or elimination of infection in a patient undergoing treatment for a fungal infection or associated disease over time. The methods described herein provide a viable solution for such medical needs. In addition, methods are provided that allow a patient to be treated with the appropriate or a more directed fungal therapy by stratifying patients based on whether they possess or do not possess antibodies specific for a particular fungal pathogen, thereby deterring infection, or based on whether they have or do not have anti-fungal Kex peptide antibodies that are specific for a given type of pathogenic fungus.

In an embodiment, a method is provided for detecting antibodies against a fungal-derived Kex protein or peptide in a sample obtained from a subject, in which the method comprises: (a) contacting a biological sample obtained from the subject with a Kex peptide derived from one or more, two or more, three or more, or four different fungal organisms selected from *Pneumocystis, Aspergillus, Candida*, or *Cryptococcus*; and (b) detecting the binding of the fungal-derived Kex peptide to antibodies in the sample which specifically bind to the Kex peptide, said detection of binding being indicative of the presence of antibodies against the Kex peptide of the fungal organisms in the subject's sample. In an embodiment, the Kex peptide is attached to a solid support or substrate. In an embodiment, the binding is detected by performing an immunoassay, e.g., an enzyme linked immunosorbent assay. In an embodiment, the Kex peptide of one or more of the *Pneumocystis, Aspergillus, Candida*, or *Cryptococcus* fungal organisms is attached to the solid support or substrate. In an embodiment, the Kex peptides of two or more of the *Pneumocystis, Aspergillus, Candida*, or *Cryptococcus* fungal organisms are attached to the solid support or substrate. In an embodiment, the Kex peptides of three or more of the *Pneumocystis, Aspergillus, Candida*, or *Cryptococcus* fungal organisms are attached to the solid support or substrate. In an embodiment, the Kex peptides of all four of the *Pneumocystis, Aspergillus, Candida*, or *Cryptococcus* fungal organisms are attached to the solid support or substrate.

In another embodiment, a method of monitoring or detecting antibodies to fungal organisms associated with infection in a subject who has undergone a transplant or who is to undergo a transplant procedure to determine, for example, whether the subject is protected or will be protected from infection by one or more fungal pathogens selected from *Pneumocystis, Aspergillus, Candida*, or *Cryptococcus*, in which the method comprises: (a) measuring at a first time point the level of antibodies that bind to a Kex protein or peptide derived from at least one, at least two, at least three, or four different fungal organisms selected from *Pneumocystis, Aspergillus, Candida*, or *Cryptococcus*, in a sample obtained from the subject prior to undergoing transplant surgery; (b) measuring the levels of antibodies that bind to a Kex protein or peptide derived from at least one, at least two, at least three, or four different fungal organisms selected from *Pneumocystis, Aspergillus, Candida*, or *Cryptococcus* in a sample obtained from the subject at one or more time points after the subject has undergone transplant surgery; and (c) detecting that the subject sample contains a level of antibodies that specifically bind to the Kex peptide of one or more of the *Pneumocystis, Aspergillus, Candida*, or *Cryptococcus* fungal organisms relative to a predetermined or threshold level or to a control level, wherein a high level of antibodies that bind to the fungal-derived Kex peptide in the subject's sample indicates that the subject has produced an immune response against the fungal organism. In an embodiment, antibodies detected in the subject's sample that bind to the Kex peptide of *Pneumocystis* may serve to protect the subject from infection not only by *Pneumocystis*, but also from infection by one or more of the other fungal organisms, *Aspergillus, Candida*, or *Cryptococcus*, according to the present invention. Similarly, in another embodiment, the detection of a high level of antibodies that bind *Aspergillus*-derived Kex peptide in the subject's sample may serve to protect the subject from infection not only by *Aspergillus*, but also from infection by one or more of the other fungal organisms, *Pneumocystis, Candida*, or *Cryptococcus*, according to the present invention. In another embodiment, the detection of a high level of antibodies that bind *Candida*-derived Kex peptide in the subject's sample may serve to protect the subject from infection not only by *Candida*, but also from infection by one or more of the other fungal organisms, *Pneumocystis, Aspergillus*, or *Cryptococcus*, according to the present invention. In another embodiment, the detection of a high level of antibodies that bind *Cryptococcus*-derived Kex peptide in the subject's sample may serve to protect the subject from infection not only by *Cryptococcus*, but also from infection by one or more of the other fungal organisms, *Pneumocystis, Aspergillus*, or *Candida*, according to the present invention.

Repeating the practice of the above-described method over time (at different time intervals or different time periods) allows monitoring of the subject's antibody levels against the different fungal pathogens (i.e., the levels of antibodies that bind the Kex peptide derived from a fungal pathogen) and can inform the medical practitioner or clinician as to whether continued, new, or different treatment of the subject with an appropriate anti-fungal drug or therapy is needed or warranted, or whether no or less anti-fungal treatment is warranted, based on the measured titers of antibodies in the subject's sample.

Embodiments of the invention also provide methods for detecting in a subject's biological sample, e.g., blood, serum, plasma, lymph, bronchoalveolar lavage fluid, the presence of antibodies that bind Kex peptide derived from one or more of the *Pneumocystis, Aspergillus, Candida*, or *Cryptococcus* fungal organisms, wherein the levels of antibodies against one or more of the fungal organisms in the biological sample are determined simultaneously. For example, in one embodiment, the method comprises: (a) contacting a biological sample obtained from the subject with a plurality of Kex peptides that selectively bind to a plurality of antibodies in the subject's sample for a period of time sufficient to form bound Kex peptide-antibody complexes; (b) detecting binding of the Kex peptides to the plurality of antibodies in the subject's sample, thereby determining the levels of antibodies to the Kex peptides in the sample; and (c) comparing the levels of the plurality of antibodies in the sample with predetermined threshold values, wherein levels of antibodies that bind to at least one of the plurality of Kex peptides above or below the predetermined threshold values indicates, for example, that the subject has an antibody titer and has generated an immune response against the Kex peptide derived from one or more of the fungal organisms. Accordingly, the subject having a measured antibody response to the Kex peptide is protected from infection and disease associated with one or more of the *Pneumocystis, Aspergillus, Candida*, or *Cryptococcus* fungal organisms.

In another embodiment, methods for assessing antibodies that bind to the Kex peptide of one or more of the fungal organisms *Pneumocystis, Aspergillus, Candida*, or *Cryptococcus* in a subject are provided, in which the methods comprise: (a) contacting a biological sample obtained from the subject with a composition comprising one or more (a plurality of) Kex peptides derived from *Pneumocystis, Aspergillus, Candida*, or *Cryptococcus* for a period of time sufficient to form antibody-Kex peptide complexes; (b) detecting binding of the plurality of the Kex peptides to antibodies in the sample, thereby detecting the level or titer of anti-Kex peptide antibodies in the sample; and (c) comparing the level or titer of the anti-Kex peptide antibodies in the biological sample with predetermined threshold values or control values, wherein levels of at least one of the anti-Kex peptide antibodies above or below the predetermined threshold values indicates that the subject has or does not have, respectively, an adequate immune response (antibody response) to prevent infection by the one or more fungal organisms.

In another embodiment, a composition is provided, which comprises a solid substrate and a plurality of Kex peptides derived from one or more of *Pneumocystis, Aspergillus, Candida*, or *Cryptococcus* immobilized on the substrate. In an embodiment, a Kex peptide from each of *Pneumocystis, Aspergillus, Candida*, or *Cryptococcus* is immobilized at a different, indexable, location on the substrate. In other embodiments, a mixture of Kex peptides from two or more, three or more, or all four of *Pneumocystis, Aspergillus, Candida*, or *Cryptococcus* is immobilized at a different, indexible, location on the substrate. The binding of anti-Kex peptide antibodies from a sample obtained from a subject can be measured or detected by measuring or detecting complexes of the anti-Kex peptide antibodies bound to the Kex peptides localized on the substrate. In an embodiment, the composition is contained in a kit for performing an immunoassay to detect and/or measure the antibody-peptide complexes, as well as determine or measure the level or amount of antibody present in the subject's sample.

Antibodies

As described herein, antisera comprising antibodies that specifically bind a Kexin peptide of a fungal organism, such as *Pneumocystis*, and that cross-react with a Kexin peptide of one or more different fungal organisms, such as one or more of *Aspergillus, Candida*, or *Cryptococcus*, to provide immune protection against infection and disease caused by two or more of these fungal pathogens are useful in therapeutic methods. For example, isolated antiserum containing antibodies that target and/or inhibit or neutralize the activity of the Kexin protein in two or more of these fungal pathogens is particularly useful in the methods of the invention. In particular embodiments, the invention provides methods of using isolated antiserum (or immune plasma) comprising anti-*Pneumocystis, Aspergillus, Candida*, or *Cryptococcus* Kexin polypeptide antibodies or antigen binding fragments thereof, in particular, anti-Kex peptide antibodies or antigen binding fragments thereof, for the treatment or prevention of infection by these fungal pathogens and/or their associated diseases and conditions, such as pulmonary diseases and disorders of various types, pneumonia, COPD, asthma, including severe asthma, etc. In an embodiment, the antisera and/or the specific antibodies contained therein may be obtained or isolated from individuals who have recovered from fungal infection caused by one or more of the *Aspergillus, Pneumocystis, Candida*, or *Cryptococcus* fungal pathogens or from those who have survived infection caused by one or more of these organisms. In an embodiment, the antiserum is obtained or isolated from blood, serum, or plasma of such individuals.

Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. $F(ab')_2$, and Fab fragments that lack the Fc fragment of an intact antibody, clear more rapidly from the circulation, and may have less nonspecific tissue binding than an intact antibody (Wahl et al., *J. Nucl. Med.* 24:316-325 (1983)). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, (1995)), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody, because small molecules of ~60-100 kDa in size provide faster blood clearance and rapid tissue uptake. See, e.g., Power et al., (Generation of recombinant multimeric antibody fragments for tumor diagnosis and therapy, Methods Mol Biol, 207, 335-50, (2003); and Wu et al., Anti-carcinoembryonic antigen (CEA) diabody for rapid tumor targeting and imaging, Tumor Targeting, 4, 47-58, (1999)).

Various techniques for making and using unconventional antibodies have been described. Bispecific antibodies produced using leucine zippers are described by Kostelny et al. (J. Immunol. 148(5):1547-1553, (1992)). Diabody technology is described by Hollinger et al. (Proc. Natl. Acad. Sci. USA 90:6444-6448, (1993)). Another strategy for making bispecific antibody fragments using single-chain Fv (sFv) diners is described by Gruber et al. (J. Immunol. 152:5368, (1994)). Trispecific antibodies are described by Tutt et al. (J. Immunol. 147:60, (1991)). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, (1988)). See, also, U.S. Pat. Nos. 5,091,513, 5,132,405 and 4,956,778; and U.S. Patent Publication Nos. 20050196754 and 20050196754.

In various embodiments, an antiserum (isolated antiserum) contains anti-Kex peptide antibodies or antigen binding fragments thereof derived from the fungal organisms described herein that are monoclonal or polyclonal. In various embodiments, the antiserum or immune plasma containing antibodies that bind Kexin polypeptides and peptides is obtained from an immune survivor of infection by one or more of the fungal pathogens described herein. In an embodiment, the antiserum is an antiserum isolated from a survivor of infection by one or more of the *Pneumocystis, Aspergillus, Candida*, or *Cryptococcus* fungal pathogens. The invention also encompasses obtaining or isolating the antibodies from immune serum (antiserum) or immune plasma and producing hybrid or chimeric antibodies therefrom. In such hybrid or chimeric antibodies one pair of heavy and light chains is obtained from a first antibody, while the other pair of heavy and light chains is obtained from a different second antibody. Such hybrids or chimeric antibodies may also be formed using humanized heavy and light chains. Methods for isolating antibodies and producing hybrid or chimeric antibodies are known and practiced by those having skill in the art.

In general, intact antibodies are said to contain "Fc" and "Fab" regions. The Fc regions are involved in complement activation and are not involved in antigen binding. An antibody from which the Fc region has been enzymatically cleaved, or which has been produced without the Fc region, designated an "$F(ab')_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies (and immune serum or plasma containing antibodies) can be produced or generated by any of the methods known in the art utilizing soluble polypeptides, or immunogenic fragments thereof, (e.g., a Kex peptide) as an immunogen. One method of obtaining antibodies is to immunize suitable host animals or subjects with an immunogen and to follow standard procedures for polyclonal or monoclonal antibody production. In brief, the immunogen will facilitate presentation of the immunogen (or immunogenic fragments of the immunogen) on the cell surface. Immunization of a suitable host can be carried out in several ways. By way of example, nucleic acid sequences encoding immunogenic Kexin peptides can be provided to the host in a delivery vehicle (or a molecular expression construct) that is taken up by immune cells of the host. The cells will, in turn, process and appropriately express the Kex peptide in a manner that generates an immunogenic response in the host. In embodiments, Kex peptides of *Pneumocystis, Aspergillus, Candida*, or *Cryptococcus* may be expressed by the delivery vehicle or expression construct, e.g., as shown in FIG. 4. In other exemplary embodiments, nucleic acid sequences encoding Kex peptides of *Pneumocystis, Aspergillus, Candida*, or *Cryptococcus* (as shown in FIG. 4) may be expressed in cells in vitro, and the expressed, recombinant Kex peptide products may be isolated and used as immunogens to raise anti-Kex peptide antibodies and to generate an anti-Kex antiserum in a suitable immunized host.

Alternatively, antibodies against the Kex peptides of any, or all, of the *Pneumocystis, Aspergillus, Candida*, or *Cryptococcus* fungal pathogens may, if desired, be derived from an antibody phage display library. A bacteriophage is capable of infecting and reproducing within bacteria, which can be engineered, when combined with human immunoglobulin (antibody) genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from an immunized host. Antibody purification methods include, without limitation, salt precipitation (for example, with ammonium sulfate), ion exchange chromatography (for example, on a cationic or anionic exchange column, preferably run at neutral pH and eluted with step gradients of increasing ionic strength), gel filtration chromatography (including gel filtration HPLC) and chromatography on affinity resins such as protein A, protein G, hydroxyapatite, or anti-immunoglobulin.

In certain aspects, antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can, in turn, be obtained from the hybridoma that produces the antibody, and then the antibody may be produced synthetically or recombinantly from these nucleic acid sequences. For the production of large amounts of antibody, it is generally more convenient to obtain an ascites fluid. The method of raising ascites fluid generally comprises injecting hybridoma cells into an immunologically naive histocompatible or immunotolerant mammal, especially a mouse. The mammal may be primed for ascites production by prior administration of a suitable composition (e.g., Pristane). Ascites fluid containing antibodies, typically in high concentration, can be obtained from the peritoneal fluid of the animal that harbors the injected hybridoma cells.

Monoclonal antibodies (Mabs can also be "humanized" by methods known in the art. "Humanized" antibodies are antibodies in which at least part of the sequence has been altered from its initial form to render it more like immunoglobulins derived from a human source. Techniques to humanize antibodies are particularly useful when antibodies are generated in a non-human animal (e.g., mice, rats). Nonlimiting examples of methods for humanizing a murine antibody are provided in U.S. Pat. Nos. 4,816,567, 5,530,101, 5,225,539, 5,585,089, 5,693,762 and 5,859,205.

In an embodiment of the foregoing, one or more antibodies or antigen binding fragments thereof generated against the Kex peptide derived from the different fungal pathogens, namely, *Pneumocystis, Aspergillus, Candida*, or *Cryptococcus*, can be used in a pharmaceutical composition alone or in combination to provide immune protection against disease or infection caused by one or more of these fungal pathogens in a subject in need thereof. Such antibodies may be isolated or purified from an antiserum as described herein, or they may be generated, e.g., by recombinant molecular biology techniques, purified and formulated for pharmaceutical use in a subject in need. Such a formulation of antibodies may have immune protective properties similar to those afforded by an isolated antiserum comprising anti-fungal Kex peptide antibodies as described herein.

Vaccines

A vaccine is a biological preparation that provides active, acquired immunity in a subject to a particular disease. A vaccine typically contains an agent that resembles a disease-causing pathogenic agent, e.g., a microorganism, a fungus, etc., and is often made from a weakened or killed form of the agent, or a toxin or surface protein or peptide of the agent. After administration of the vaccine to a subject, the agent is expressed and recognized as foreign (or "non-self") to the subject and stimulates the subject's immune system to mount an immune response (a B cell (antibody) and/or a T cell (cellular) immune response) and to destroy the agent. In addition, cells (e.g., B cells) of the immune system that are exposed to the vaccinating agent retain a memory of the agent, such that the agent is recognized and destroyed by the memory cells upon a later or subsequent encounter. Vaccines can be prophylactic (e.g., to prevent or ameliorate the effects of a future infection by a pathogen), or therapeutic (e.g., to treat disease or infections caused by or associated with pathogens or disease-causing agents upon or after a subject has been infected with or encountered a pathogen).

While many vaccines are prepared from an attenuated version of a pathogen or from inactivated disease-causing organisms, or a suitable part of such pathogens or organisms, such as a toxin, protein/peptide, or deleterious enzyme, the antigen to which the immune system responds frequently constitutes a relatively small number of amino acids, such as a peptide (e.g., a Kex peptide). A protein or peptide part of a pathogen may constitute a vaccine. A peptide vaccine is any peptide which serves to immunize an organism (elicit an immune response or a protective immune response, such as an antibody (B cell) response and/or an immune cell (T cell) response in the immunized organism) against a pathogen. In embodiments, the peptide antigen may be a Kex peptide derived from one, two, three, or all of the *Pneumocystis,*

*Aspergillus, Candida,* or *Cryptococcus* fungal pathogens as described herein. In an embodiment, a vaccine comprising a Kex peptide antigen derived from a fungal organism, such as a *Pneumocystis, Aspergillus, Candida,* or *Cryptococcus* fungal organism described herein, may be used to provide immune protection against each of the other fungal organisms following administration to a recipient subject in need.

For non-attenuated vaccines, the peptide sequences that trigger a protective immune response are identified, and synthetic (or recombinantly-produced) versions of the peptides are employed as the vaccine substance. Because they are non-naturally occurring and synthetic, peptide vaccines pose little to no risk of mutation or reversion, and little or no risk of contamination by pathogenic or toxic substances. Moreover, chemical manipulation or modification of the peptide structure may result in increased stability and decreased unwanted side effects or adverse effects that may be associated with a native protein or peptide sequence.

Synthetically or recombinantly produced peptide antigens can be readily prepared in large amounts as components of vaccines. Such substances may also expose parts of a protein antigen that are not recognized by the immune system during a natural infection, possibly as a result of masking or post-translational modifications of proteins. Sequencing new strains and serotypes of microorganisms, fungal pathogens and other pathogenic organisms allows for rapid modification of peptide antigens to generate strain-specific immune responses, particularly against an antigenic epitope that is recognized and targeted by antibodies and cells of the host's or recipient's immune system. In some cases, modelling of three-dimensional epitopic or antigenic sites of a pathogen may be employed to generate synthetically the correct epitopic or antigenic site(s) on peptide antigens.

In an aspect, the invention embraces a vaccine (or an immunogenic composition) comprising a synthetically (recombinantly) produced peptide, i.e., a Kexin peptide, that is nonidentical, but immunologically targetable, among several different types of fungal pathogens (e.g., the *Pneumocystis, Aspergillus, Candida* and *Cryptococcus* fungal pathogens) and is useful for treating or preventing infection or disease caused by or associated with the multiple fungal pathogens after administration (immunization) to a subject. In an embodiment, Kexin peptide sequences for use in generating an immune response or antibody response are shown, for example, in FIGS. 1 and 4. In an embodiment, a peptide vaccine or immunogenic composition from one of *Pneumocystis, Aspergillus, Candida,* or *Cryptococcus*, and in particular, *Pneumocystis hominis, Aspergillus fumigatus, Candida albicans* or *Cryptococcus neoformans* fungal organisms, when used to immunize an individual, elicits an immune response in the form of the production of antiserum (or immune plasma) containing cross-reactive antibodies which protect against all of the etiologically distinct fungal pathogens *Pneumocystis, Aspergillus, Candida* and *Cryptococcus*, and in particular, *Pneumocystis hominis, Aspergillus fumigatus, Candida albicans* and *Cryptococcus neoformans*. Accordingly, an antiserum or immune plasma generated by a vaccine or immunogenic composition comprising a Kex peptide of a *Pneumocystis, Aspergillus, Candida,* or *Cryptococcus* (or from aPneumocystis *hominis, Aspergillus fumigatus, Candida albicans,* or *Cryptococcus neoformans* fungal organism as described herein) may be used as a sole therapeutic or protective agent needed to treat or prevent infection or disease caused by or associated with infection not only by the fungal organism whose Kex peptide was used as immunogen, but also by more than one different fungal pathogen, namely, the *Pneumocystis, Aspergillus, Candida* and/or *Cryptococcus* fungal pathogens, and in particular, infection or disease caused by or associated with *Pneumocystis hominis, Aspergillus fumigatus, Candida albicans* and/or *Cryptococcus neoformans*. In an embodiment, the antiserum generated by such as peptide vaccine is isolated. In an embodiment, the isolated antiserum is used in a pharmaceutical composition.

Pharmaceutical Compositions

The present invention features methods for treating or preventing infection and disease associated with infection of a subject by one or more fungal pathogens. The methods include administering to a subject in need thereof an immunologically effective amount of an isolated antiserum containing antibodies generated against a Kexin peptide derived from a *Pneumocystis, Aspergillus, Candida,* or *Cryptococcus* fungal pathogen, which antiserum cross-treats and/or protects the subject from infection by and/or disease associated with not only the fungal organism from which the Kex peptide immunogen was derived, but also from infection by and/or disease associated with one or more different fungal pathogens selected from *Pneumocystis, Aspergillus, Candida,* or *Cryptococcus*. In an embodiment, the isolated antiserum is used in a pharmaceutical composition.

Typically, the carrier or excipient for an immunogenic composition or vaccine as described herein is a pharmaceutically acceptable carrier or excipient, such as sterile water, aqueous saline solution, aqueous buffered saline solutions, aqueous dextrose solutions, aqueous glycerol solutions, ethanol, or combinations thereof. The preparation of such solutions ensuring sterility, pH, isotonicity, and stability is affected according to protocols established in the art. Generally, a carrier or excipient is selected to minimize allergic and other undesirable effects, and to suit the particular route of administration, e.g., subcutaneous, intramuscular, intranasal, and the like. Such methods also include administering an adjuvant, such as an oil-in-water emulsion, a saponin, a cholesterol, a phospholipid, a CpG, a polysaccharide, variants thereof, and a combination thereof, with the composition of the invention. Optionally, a formulation for prophylactic administration also contains one or more adjuvants for enhancing the immune response to an antigen or immunogen, such as a Kex peptide antigen or immunogen. Suitable adjuvants include, without limitation, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59 (Novartis). In an embodiment, the isolated antiserum is used in a pharmaceutical composition.

The administration of an antiserum, such as an isolated antiserum, or anti-*Pneumocystis, Aspergillus, Candida,* and/or *Cryptococcus* Kexin protein or peptide monoclonal or polyclonal antibodies isolated and purified from a non-immunized, but naturally immune protected, subject (donor subject), as a therapeutic for the treatment or prevention of an infection by a fungal pathogen as described herein or a fungal pathogen-associated disease or condition (e.g., pulmonary infection or disease, poor pulmonary function, COPD, pneumonia, etc.) may be by any suitable means that results in a concentration of the therapeutic that, combined with other components, if desired, is effective in ameliorating, reducing, eliminating, abating, or stabilizing disease or disease symptoms in a subject. The therapeutic may be administered systemically, for example, formulated in a pharmaceutically-acceptable composition or buffer such as physiological saline. Preferable routes of administration include, for example, subcutaneous, intravenous, intraperitoneally, intramuscular, intrathecal, or intradermal injections that provide continuous, sustained levels of the therapeutic in the subject. The amount of the therapeutic to be administered varies depending upon the manner of administration, the age and body weight of the subject, and with the clinical symptoms of the fungal infection or associated disease. Generally, amounts will be in the range of those used for other agents used in the treatment of pulmonary disease or dysfunction, although in certain instances lower amounts may be suitable because of the increased range of protection and treatment afforded by the therapeutic. A composition is administered at a dosage that ameliorates, decreases, diminishes, abates, alleviates, or eliminations the effects of the fungal pathogen infection or disease (e.g., pulmonary infection and disease and the symptoms thereof) as determined by a method known to one skilled in the art. In an embodiment, the isolated antiserum is administered or provided to a recipient subject at or near a site of the infection or colonization by the pathogenic fungal organism or organisms.

In embodiments, a therapeutic or prophylactic treatment agent may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intrathecal, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions may in some cases be formulated to release the active agent substantially immediately upon administration or at any predetermined time or time period after administration. The latter types of compositions are generally known as controlled release formulations, which include (i) formulations that create a substantially constant concentration of a therapeutic agent or drug within the body over an extended period of time; (ii) formulations that after a predetermined lag time create a substantially constant concentration of a therapeutic agent or drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target a disease using carriers or chemical derivatives to deliver the therapeutic agent or drug to a particular cell type. For some applications, controlled release formulations obviate the need for frequent dosing during the day to sustain a therapeutic level in plasma, serum, or blood. In an embodiment, an isolated antiserum may be formulated with one or more additional components for administration to a subject.

Any of a number of strategies can be pursued in order to obtain controlled release in which the rate of release outweighs the rate of metabolism of the therapeutic agent or drug in question. In one example, controlled release is obtained by appropriate selection of various formulation parameters and ingredients, including, e.g., various types of controlled release compositions and coatings. Thus, the therapeutic agent or drug may be formulated with appropriate excipients into a pharmaceutical composition that, upon administration, releases the therapeutic agent or drug in a controlled manner. Examples include single or multiple unit tablet or capsule compositions, oil solutions, suspensions, emulsions, microcapsules, microspheres, molecular complexes, nanoparticles, patches, and liposomes.

A pharmaceutical composition may be administered parenterally by injection, infusion or implantation (subcutaneous, intravenous, intramuscular, intraperitoneal, intrathecal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, noted supra.

Compositions for parenteral use may be provided in unit dosage forms (e.g., in single-dose ampules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a disease or dysfunction, such as pulmonary disease or dysfunction, the composition may include suitable parenterally acceptable carriers and/or excipients. In some cases, an active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, a pharmaceutical composition comprising an active therapeutic (e.g., an isolated antifungal antiserum described herein) is formulated for intravenous delivery, e.g., intravenous, injection, or intrathecal delivery. In an embodiment, the antiserum is an isolated antiserum. To prepare such a composition, the suitable therapeutic(s) are dissolved or suspended in a parenterally acceptable liquid vehicle, excipient, or solvent. Among acceptable vehicles and solvents that may be employed are, for example, water; water adjusted to a suitable pH by the addition of an appropriate amount of hydrochloric acid, sodium hydroxide or a suitable buffer; 1,3-butanediol; Ringer's solution; and isotonic sodium chloride solution and dextrose solution. The aqueous formulation may also contain one or more preservatives (e.g., methyl, ethyl or n-propyl p-hydroxybenzoate). In cases in which one of the agents is only sparingly or slightly soluble in water, a dissolution enhancing or solubilizing agent can be added, or the solvent may include 10-60% w/w of propylene glycol or the like.

Kits and Compositions for Detecting and/or Quantifying Antibodies that React with Fungal-Derived Kex Peptides In another embodiment, kits and compositions are provided that advantageously allow for the detection and/or quantification of the presence of antibodies directed against the Kex protein or peptide of one or more of *Pneumocystis, Aspergillus, Candida,* or *Cryptococcus* fungal pathogens, or the levels of such one or more antibodies that may be present, in a subject's sample (e.g., blood or serum). In an embodiment, the subject is a human patient. In an embodiment, the patient has undergone a transplant, e.g., an organ or tissue transplant, or is to undergo a transplant, and thus may be at higher risk for infection by one or more fungal pathogens. In an embodiment, the transplant patient, or the patient to undergo a transplant, is immunosuppressed and/or is otherwise treated with drugs to reduce the likelihood of rejection of the transplanted organ or tissue, thereby making the patient more vulnerable or susceptible to infection and/or disease caused by one or more of the *Pneumocystis, Aspergillus, Candida,* or *Cryptococcus* fungal pathogens. In an embodiment, the patient has received, or is to receive, a transplant of an organ selected from kidney, liver, heart, bone marrow, pancreas, lung, etc.

Such kits as described herein fulfill a long-felt need in the art for detecting or qualifying whether any patient, but particularly a transplant patient, has adequate levels (titer) of anti-fungal pathogen antibodies to ensure that the patient does not become infected with one or more fungal pathogens as described herein, for example, during a hospital stay, or during or following a medical procedure or treatment (e.g., surgery or transplant), performed either on in-patient or an out-patient basis. At present, because of a lack of appropriate reagents and assays, it is difficult to assess whether a patient who is to undergo a medical procedure or surgery, in particular, an immunosuppressed patient who is to undergo a transplant procedure, or a patient who is to initiate other immunosuppressive therapies, will contract a fungal infection, e.g., infection and/or disease caused by one or more of the *Pneumocystis, Aspergillus, Candida,* or *Cryptococcus* fungal pathogens following or during immunosuppressive therapies and treatments. The use of a kit with which a patient's sample can be tested to determine if the patient has an antibody titer against one or more of these fungal pathogens (e.g., a high or a low antibody titer against one or more of the fungal pathogens) would greatly enhance the success of the patient's post-surgical or post-transplant recovery and directed treatment. For example, if, following testing of a patient's sample (e.g., a blood or serum sample from a transplant patient) using a kit as described herein, the patient is determined to have a low, negligible, or no antibody (antiserum) titer against against one or more of the fungal pathogens, in particular, against the Kex peptide of one or more of the fungal pathogens, it could be surmised that the patient would not be naturally protected against a possible or real infection by one or more of the *Pneumocystis, Aspergillus, Candida,* or *Cryptococcus.*

A kit as described herein would allow the tester and the patient to determine and know if the patient's sample (serum sample) contains antibodies against one or more, two or more, three or more, or four of Kex protein/peptide of the *Pneumocystis, Aspergillus, Candida,* or *Cryptococcus* organisms. Should the results obtained from the use of the kit indicate that the patient has no specific anti-fungal Kex peptide antibodies, or a low titer of such antibodies (e.g., no specific anti-fungal Kex peptide antibodies in serum), directed to a specific anti-fungal Kex peptide, the patient would be identified as potentially vulnerable or susceptible to infection to (a) particular fungal pathogen(s) and could then be administered the appropriate anti-fungal treatment for the specific fungal pathogen(s) against which the patient has no, or negligible, specific antibodies, or a reduced antibody titer. In an embodiment, the patient is administered a prophylactic anti-fungal treatment or therapy. In an embodiment, the treatment comprises administering to the patient an appropriate drug or medication that is best designed to treat infection or disease associated with infection by a specific fungal pathogen or by two or more fungal pathogens, namely, *Pneumocystis, Aspergillus, Candida,* or *Cryptococcus.* In an embodiment, the treatment comprises administering to the patient a composition as described herein comprising one, two, three, or four of the described fungal-derived Kex peptides to generate a cross-reactive (cross-protective) antibody immune response in the patient, thereby reducing or eliminating one or more of the *Pneumocystis, Aspergillus, Candida,* or *Cryptococcus* organisms associated with the infection. Antibodies produced against a Kex peptide of one of the fungal organisms can recognize a Kex peptide of the other fungal organisms as described herein, thereby conferring protection (cross-protection) against more than one of the fungal organisms in the patient.

In an embodiment, the invention provides a kit for detecting, or qualifying the levels of, antibodies directed against the Kex protein or peptide of one, two, three, or four of *Pneumocystis, Aspergillus, Candida,* or *Cryptococcus* organisms in a patient sample, in which the kit comprises a substrate having attached thereto a Kex peptide derived from one or more, two or more, three or more, or each of *Pneumocystis, Aspergillus, Candida,* or *Cryptococcus* fungal organisms for measuring the level of antibodies in the sample which bind or immunologically react with the peptide, onto which a biological sample obtained from a patient is applied; and a labeled detection molecule for detecting and measuring the level of antibodies that bind to the Kex peptides on the substrate. In an embodiment, detecting anti-fungal Kex peptide antibodies in the sample or the measuring the level of such antibodies present in the patient's sample is compared to a positive and/or a negative control. In an embodiment, detecting anti-fungal Kex peptide antibodies in the sample or the measuring the level of such antibodies present in the patient's sample is compared to a cutoff value. In an embodiment, the substrate has attached thereto Kex peptide derived from each of *Pneumocystis, Aspergillus, Candida,* and *Cryptococcus.* In an embodiment, the substrate has attached thereto Kex peptide derived from one of *Pneumocystis, Aspergillus, Candida,* and *Cryptococcus.* In an embodiment, the substrate has attached thereto Kex peptide derived from *Pneumocystis* and *Aspergillus.* In an embodiment, the substrate has attached thereto Kex peptide derived from *Pneumocystis* and *Candida.* In an embodiment, the substrate has attached thereto Kex peptide derived from *Pneumocystis* and *Cryptococcus.* In an embodiment, the substrate has attached thereto Kex peptide derived from *Candida* and *Aspergillus.* In an embodiment, the substrate has attached thereto Kex peptide derived from *Cryptococcus* and *Aspergillus.* In an embodiment, the substrate has attached thereto Kex peptide derived from *Candida* and *Cryptococcus.* In an embodiment, the substrate has attached thereto Kex peptide derived from *Pneumocystis, Aspergillus* and *Candida.* In an embodiment, the substrate has attached thereto Kex peptide derived from *Pneumocystis, Aspergillus* and *Candida.* In an embodiment, the substrate has attached thereto Kex peptide derived from *Pneumocystis, Aspergillus* and *Cryptococcus.* In an embodiment, the substrate has attached thereto Kex peptide derived from *Pneumocystis, Cryptococcus* and *Candida.* In an embodiment, the substrate has attached thereto Kex peptide derived from *Aspergillus, Cryptococcus* and *Candida.* In an embodiment, the Kex peptides are recombinantly produced. In an embodiment, the detection of antibodies in the sample that bind to the fungal-derived Kex peptide is performed using an immunoassay, such as an ELISA. In an embodiment, the ELISA detects a complex between a Kex peptide bound to an anti-fungal Kex peptide antibody present in the sample. In an embodiment, the Kex peptides are recombinantly produced. In an embodiment, the detection of antibodies in the sample that bind to the fungal-derived Kex peptide is performed using an immunosorbent assay, by immunoprecipitation, by immunoblotting, or a combination thereof.

The invention provides kits comprising reagents that allow for assessing, measuring, evaluating or detecting antibodies directed against one or more of *Pneumocystis, Aspergillus, Candida*, or *Cryptococcus* fungal pathogens. Such antibodies may be contained in a biological sample obtained from a subject undergoing testing, assessment, or evaluation using the kit. In particular, the biological sample may be a blood, serum, plasma, urine, cerebrospinal fluid, sputum, bronchiolar lavage, tears, saliva, or semen sample, or tissue or cell sample obtained from a subject. In particular, the reagents of the kit comprise at least one of the Kex peptides of the *Pneumocystis, Aspergillus, Candida*, or *Cryptococcus* fungal pathogens as described herein. (e.g., FIG. 1A and FIG. 3).

In a specific embodiment, the kit is provided as an enzyme linked immunosorbent assay (ELISA) kit comprising the Kex peptides of *Pneumocystis, Aspergillus, Candida*, or *Cryptococcus* attached to a solid support or substrate. The peptides thus perform as "capture" reagents that bind to antibodies present in the sample obtained from a subject undergoing testing. By way of example, the ELISA kit may comprise a solid support, such as a chip, microtiter plate comprising many wells (e.g., a 96-well plate), bead, or resin having the peptide capture reagents attached thereon. In one embodiment, the kit comprises a Kex peptide derived from each of *Pneumocystis, Aspergillus, Candida*, or *Cryptococcus* as described herein attached independently to discrete areas or components of solid substrates or supports, for example, the Kex peptides of each fungal organism are attached to separate and discrete wells of a microtiter plate or are independently attached to beads to produce populations of beads having the Kex peptides from each of *Pneumocystis, Aspergillus, Candida*, or *Cryptococcus* attached. In another embodiment, the kit comprises a combination or mixture of the Kex peptides derived from *Pneumocystis, Aspergillus, Candida*, or *Cryptococcus* attached to an area or component of the solid substrate or support, for example, the Kex peptides of all of *Pneumocystis, Aspergillus, Candida*, or *Cryptococcus* are attached to a single well of a microtiter plate or to a single bead. In a further embodiment, the kit comprises a combination of one, two or more, three or more, or four of the Kex peptides derived from *Pneumocystis, Aspergillus, Candida*, or *Cryptococcus* attached to a given area of a solid substrate or support, such as a single well of a microtiter plate.

In embodiments, in the ELISA platform, a well of a microtiter plate may have attached thereto a *Pneumocystis* Kex peptide, an *Aspergillus* Kex peptide, a *Candida* Kex peptide, or a *Cryptococcus* Kex peptide. In the ELISA platform, a well of a microtiter plate may have attached thereto aPneumocystis Kex peptide and an *Aspergillus* Kex peptide. In the ELISA platform, a well of a microtiter plate may have attached thereto a *Pneumocystis* Kex peptide and a *Candida* Kex peptide. In the ELISA platform, a well of a microtiter plate may have attached thereto a *Pneumocystis* Kex peptide and a *Cryptococcus* Kex peptide. In the ELISA platform, a well of a microtiter plate may have attached thereto an *Aspergillus* Kex peptide and a *Candida* Kex peptide. In the ELISA platform, a well of a microtiter plate may have attached thereto an *Aspergillus* Kex peptide and a *Cryptococcus* Kex peptide. In the ELISA platform, a well of a microtiter plate may have attached thereto a *Candida* Kex peptide and a *Cryptococcus* Kex peptide. In the ELISA platform, an individual well of a microtiter plate may have attached thereto a *Pneumocystis* Kex peptide, an *Aspergillus* Kex peptide and a *Candida* Kex peptide. In the ELISA platform, an individual well of a microtiter plate may have attached thereto a *Pneumocystis* Kex peptide, an *Aspergillus* Kex peptide and a *Cryptococcus* Kex peptide. In the ELISA platform, an individual well of a microtiter plate may have attached thereto a *Pneumocystis* Kex peptide, a *Candida* Kex peptide and a *Cryptococcus* Kex peptide. In the ELISA platform, an individual well of a microtiter plate may have attached thereto an *Aspergillus* Kex peptide, a *Candida* Kex peptide and a *Crytococcus* Kex peptide.

The kit may further comprise a means for detecting the peptides or any antibodies bound thereto, e.g., detectable antibodies, a secondary antibody-signal complex, such as horseradish peroxidase (HRP)-conjugated goat anti-rabbit IgG antibody or tetramethyl benzidine (TMB) as a substrate for HRP.

In another embodiment, the kit may be provided as an immunochromatography strip comprising a membrane on which the one, two, three, or four Kex peptides are immobilized, either at discrete loci on the membrane or in combination at one locus of the membrane, and a means for detecting the binding of antibody in a test sample, e.g., detectably labeled peptides, or gold particle bound secondary antibodies, in which the membrane may be a nitrocellulose-based (NC) membrane, a PVDF membrane, or other suitable type of membrane used in the art. The kit may comprise a plastic plate or substrate onto which a sample is applied and immobilized detection agents, such as detectably labeled Kex peptides, e.g., gold particle-bound peptides temporally spaced and immobilized on the substrate, e.g., a glass fiber filter or a nitrocellulose membrane, or a labeled detection agent that can detect a complex of antibody bound to Kex peptide in one or more bands on the substrate. In such a platform, a continuous capillary flow of sample, e.g., blood or serum, is maintained over the detection reagents immobilized on the substrate such that sample antibody bound to labeled Kex peptide or sample antibody complexed to Kex peptide reagent may be detected. In general, ELISA assays and immunosorbent assays, including ELISA membrane-based immunosorbent assays, as well as variations of these assays, are known and practiced by those having skill in the art.

Solid or solid phase substrates, or carriers, that can be effectively used in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in U.S. Patent Application Publication No. US 2010/0093557 A1. Methods for the automation of immunoassays are well known in the art and include, for example, those described in U.S. Pat. Nos. 5,885,530, 4,981,785, 6,159,750 and 5,358,691.

In an embodiment, a multiplex assay, such as a multiplex ELISA, can be used to detect simultaneously different specific antibodies in a test sample. In embodiments, such methods employ an array, wherein multiple binding agents (for example capture antibodies) specific for multiple antibodies are immobilized on a substrate, such as a membrane, with each capture agent being positioned at a specific, pre-determined, location on the substrate. Methods for performing assays employing such arrays include those described, for example, in U.S. Patent Application Publication Nos. US 2010/0093557A1 and US 2010/0190656A1, the disclosures of which are specifically incorporated by reference herein. If flow cytometry, chemiluminescence, or electron-chemiluminescence technology is employed, multiplex arrays can be used in several different formats. Illustratively, flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry.

In another embodiment, a multiplex ELISA from Quansys Biosciences (Logan, Utah) involves coating multiple specific capture reagents at multiple spots (one reagent at one spot) in the same well on a 96-well microtiter plate. Chemiluminescence technology is then used to detect multiple antibodies that bind at the corresponding spots on the plate.

In certain embodiments, a patient can be diagnosed by adding a biological sample (e.g., blood or serum) from a patient to the kit, or components thereof, and detecting the relevant sample antibodies that specifically bind to the Kex peptide reagents. By way of example, the method comprises: (i) collecting blood or serum sample from the subject; (ii) adding subject's sample to the components in the kit, e.g., a holding tube or a substrate; and (iii) detecting the peptide reagents to which the sample antibodies have bound. In this method, the subject's sample, e.g., blood or serum, is brought into contact with the Kex peptide reagent(s). If the anti-Kex peptide antibody(ies) are present in the sample, the antibodies will bind to the Kex peptide reagents, or a subset thereof. In other kit and diagnostic embodiments, blood is not collected from the patient (i.e., it is already collected), and is assayed for the presence of antibodies against the Kex peptide of one or more, two or more, three or more, or four of the *Pneumocystis, Aspergillus, Candida,* or *Cryptococcus* organisms using the kit. Moreover, in other embodiments, the sample may comprise a tissue sample or a clinical sample, which can be processed, e.g., homogenized and/or suspended in medium or buffer, prior to assay. In embodiments, any antibody(ies) found to be present in a test sample from a subject may be isolated, or isolated and purified, and further characterized.

The kit can also comprise a washing solution or instructions for making a washing solution, in which the combination of the capture reagents and the washing solution allows capture of anti-Kex antibodies on the solid support for subsequent detection by, e.g., secondary antibodies, labeled reagent peptides, or mass spectrometry. In a further embodiment, a kit can comprise instructions for suitable operational parameters in the form of a label or separate insert (package insert). For example, the instructions may inform a consumer or user about how to collect the sample, how to wash the anti-Kex peptide antibody and Kex peptide reagent complex after binding has occurred, how to interpret the results, etc. In yet another embodiment, the kit can comprise one or more containers with appropriate positive and negative controls or control samples, to be used as standard(s) for detection, calibration, or normalization.

In another aspect, the invention provides kits for the treatment or prevention of an infection or disease caused by or associated with two or more of *Pneumocystis, Aspergillus, Candida,* or *Cryptococcus* fungal pathogens. In some embodiments, the kit includes an effective amount of a therapeutic or prophylactic antiserum, which contains anti-Kex peptide antibodies or antigen binding fragments thereof that bind/react with one or more of *Pneumocystis, Aspergillus, Candida,* or *Cryptococcus,* in unit dosage form. In an embodiment, the antiserum is an isolated antiserum. In other embodiments, the kit includes a therapeutic or prophylactic composition containing an effective amount of an antifungal immunoprotective agent such as antiserum in unit dosage form. In some embodiments, the kit comprises a device (e.g., nebulizer, metered-dose inhaler) for dispersal of the composition or a sterile container which contains a pharmaceutical composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, a pharmaceutical composition of the invention is provided together with instructions for administering the pharmaceutical composition containing isolated antiserum to a subject having or at risk of contracting or developing a fungal infection, particularly infection and disease and the symptoms thereof caused by *Pneumocystis, Aspergillus, Candida,* or *Cryptococcus* fungal organisms. The instructions will generally include information about the use of the composition for the treatment or prevention of an infection by one or more of *Pneumocystis, Aspergillus, Candida,* or *Cryptococcus* fungal organisms. In other embodiments, the instructions include at least one of the following: description of the therapeutic/prophylactic agent; dosage schedule and administration for treatment or prevention of infection or symptoms thereof caused by one or more of *Pneumocystis, Aspergillus, Candida,* or *Cryptococcus* fungal organisms; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Identification of Fungal Vaccine Candidates Based on Kex1 Peptide Sequence Identity To identify fungal vaccine candidates analogous to *Pneumocystis* KEX1 peptide, a multiple sequence alignment was performed in which the amino acid sequence of *Pneumocystis* KEX1 was compared with that of *Aspergillus fumigatus* Kexin (Accession no. XM746441), *Candida albicans* Kexin (Accession no. AF022372), and *Cryptococcus neoformans* Kexin (Accession no. XP572303.1) using Clustal Omega (http://www.ebi.ac.uk/Tools/msa/clustalo/) to analyze sequence identity and similarity (FIGS. 1A, 1B and 2). Based on the analysis of a conserved, 99 amino acid region of the Kexin protein (FIGS. 1A, 1B and 3), the corresponding DNA sequences were cloned in an *E. coli* expression vector and recombinant proteins of the 88-amino acid (*Aspergillus* Kex and *Candida* Kex constructs), and a 117-amino acid (*Cryptococcus* Kex construct) were produced and purified (FIG. 3). Immunologic recognition and cross-reactivity of the conserved peptides of *Aspergillus, Candida* and *Cryptococcus* was demonstrated by Western blotting using an anti-*Pneumocystis* KEX1 immune sera obtained from rhesus macaques immunized with recombinant *Pneumocystis* KEX1 (FIGS. 4A-4D and FIGS. 5A-5D).

Figure 6A:
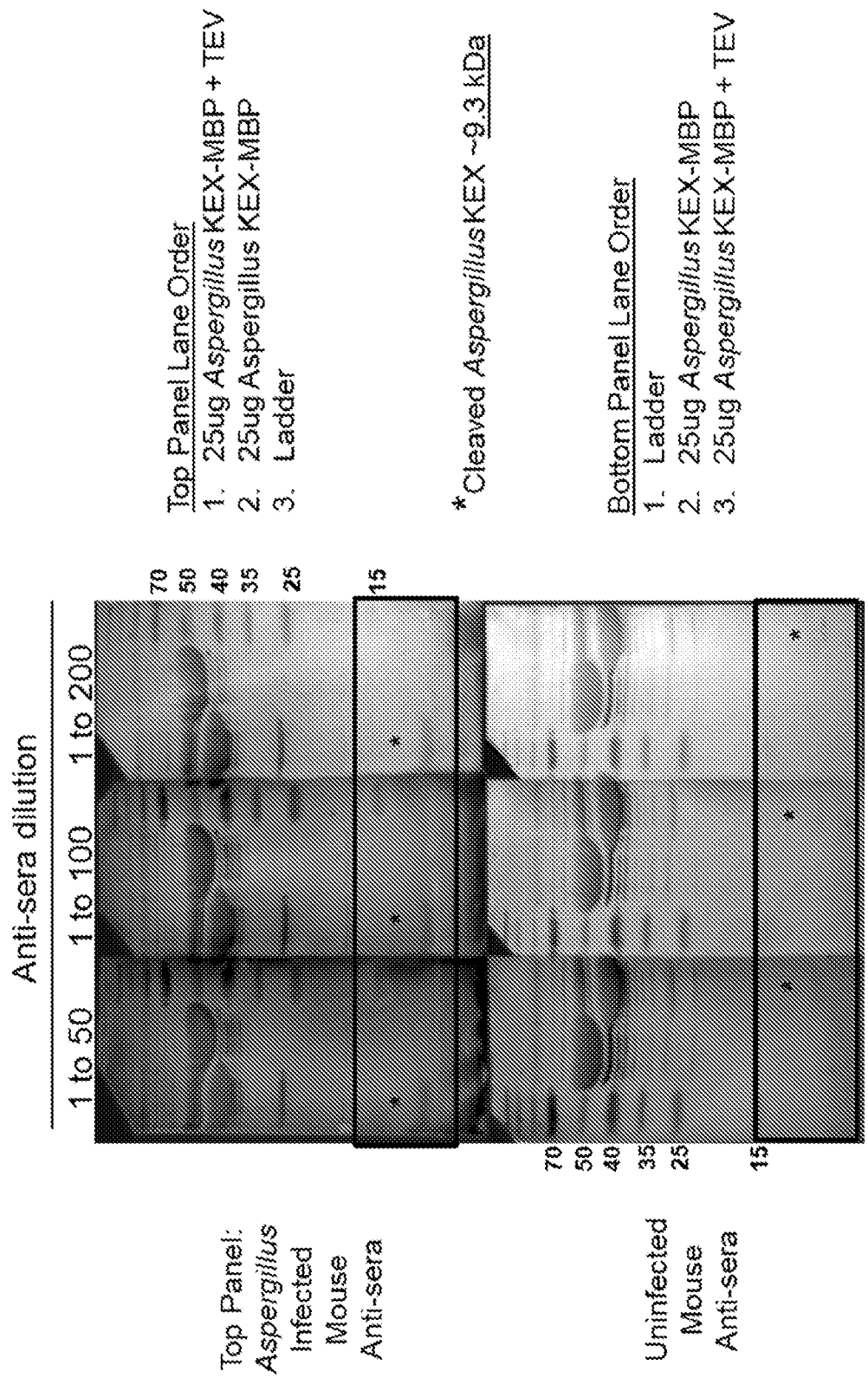
FIGS. 6A and 6B present Western blots probed with animal sera as described herein.
Figure 6B:
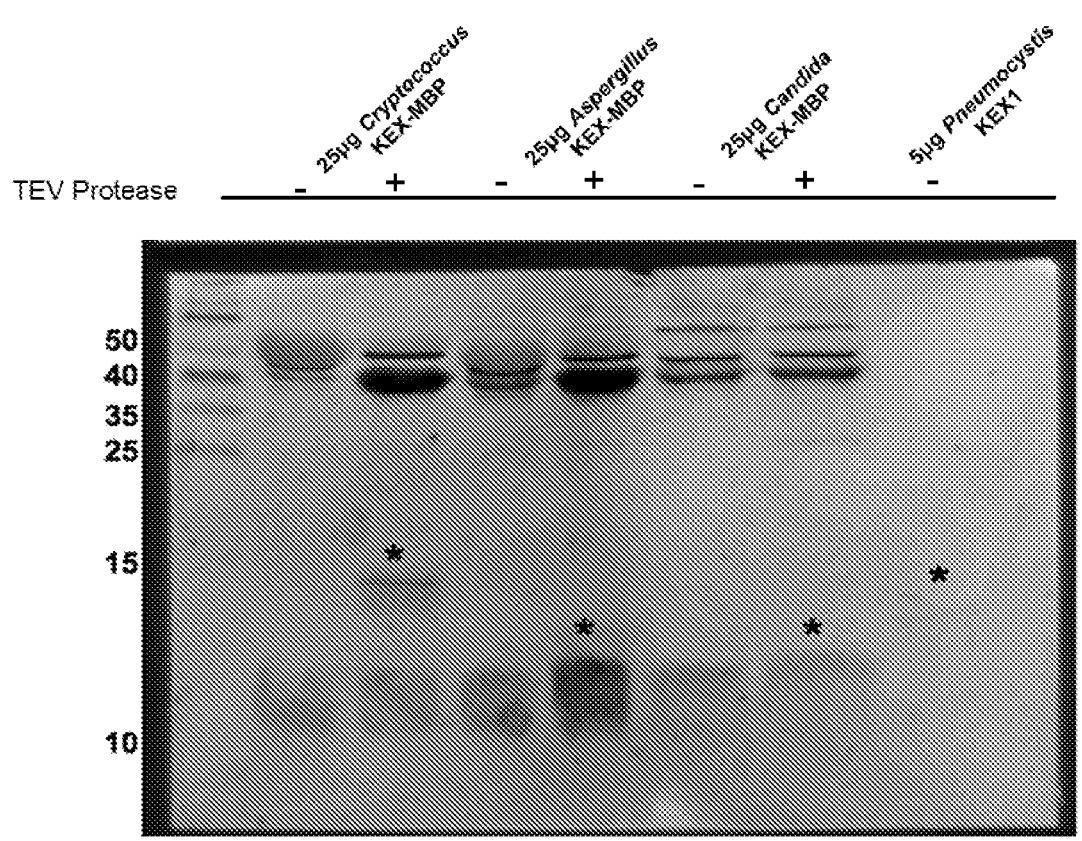

*Aspergillus* KEX (AF_KexDS88) is a target of humoral immune responses during *Aspergillus* infection, and the anti-*Aspergillus* KEX peptide antibodies are present in antiserum obtained from animals (*Aspergillus*-infected mice) having *Aspergillus* infection/asthma. (FIGS. 6A and 6B).

Example 2: Procedures for the Purification of Recombinant Kex1 Proteins

This example describes a protocol for purifying a recombinantly produced (pET28b vector), (Millipore-Sigma, US), macaque-derived Kex1 protein (peptide) that is histidine tagged.
Materials and Equipment
A. LB (Lysogeny Broth) growth medium with kanamycin (40 μg/mL), typically in a 1 L volume, pH to 7.5. 10 g NaCl, 5 g Yeast Extract and 10 g Tryptone Peptone are admixed; the volume is brought to 1 L with distilled/deionized $H_2O$.
B. 1M IPTG solution.
C. Extraction buffer: (sterile filtered), Do not pH, containing 6 M guanidinium, 50 mM Sodium phosphate ($Na_2HPO_4$, dibasic only) and 300 mM sodium chloride.
D. Wash buffer: (sterile filtered), Do not pH, containing 50 mM Sodium phosphate ($Na_2HPO_4$, Dibasic Only) and 300 mM sodium chloride.
E. 1M Imidazole solution (in $dH_2O$) (sterile filtered).
F. Talon metal affinity resin (Clontech P #635503).
G. Disposable 5 mL polypropylene column (Thermo P #29922).
H. His-tag protease inhibitor cocktail (PIC) (Sigma P #8849).
I. Bradford Dye (Bio Rad P #500-0006).
J. Bovine serum albumin (BSA) (100 μg/mL stock).
K. Coomassie Blue stain containing 0.2% Coomassie Blue, 7.5% acetic acid and 50% ethanol.
L. Coomasie Blue destain containing 50% methanol, 10% acetic acid and 40% $dH_2O$.
M. Acrylamide Bis 30% (Sigma P #1001356385) N. N,N,N',N'-Tetramethylethylenediamine (TEMED) (Sigma P #1001434505).
O. Sodium dodecyl sulfate (SDS) (10% stock solution).
P. Ammonium persulfate (APS) (10% stock solution).
Q. 1.5 Tris buffer pH 8.8 (187 g Tris Base into 1 L dH2O, bring pH to 8.8).
R. 0.5 Tris buffer pH 6.5 (60.5 g Tris Base into 1 L dH2O, bring pH to 6.5).
S. Spectra™ Multicolor Ladder-Broad range stained (Thermo P #22634).
T. SDS-PAGE sample buffer (4×).
U. Hoefer gel casting system (model SE250).
The procedure used is as follows:
A. Culture and induce protein expression in *E. coli*:
  a. Streak out monkey KEX1 pET28b onto LB KAN agar plate and incubate at 37° C. overnight (O/N) or at room temperature (RT) on the bench top until adequate bacterial growth/colonization is obtained. (Plates can be stored at 4° C. for ~1 month)
  b. Inoculate a single colony into 10 mL liquid LB KAN 40 (10 μL of 40 mg/mL KAN per 10 mL LB), (allowing ~1:5 liquid to air ratio), and grow at 37° C. O/N with shaking.
  c. Following overnight incubation, dilute culture 1:20 into liquid LB KAN 40 (10 mL of overnight culture into 190 mL of fresh medium) and leave at 37° C. on shaker.
  d. Grow cultures to an $OD_{600}$ 0.6-0.8 and then add 1 mM IPTG to induce expression; leave at 37° C. on shaker for 4-5 hours.
  e. Split total volume of culture among five 50 mL Oakridge tubes (~40 mL culture per tube). For scaling up: can use 250 mL Oakridge tubes for larger volumes.
  f. Harvest cells by centrifugation at 6,000×g and 4° C. for 25 minutes (Can use SS-34 or SLA-1500 rotor).
  g. Pour off supernatant and freeze cell pellets at −80° C. until time of use. Do not store *E. coli* pellets for longer than two weeks prior to protein extraction.
B. Protein purification using Talon metal affinity resin:
  a. Thaw pellet on ice and re-suspend cell pellet in 10 mL extraction buffer+200 μL PIC.
  b. Incubate at RT for 25 minutes on nutator.
  c. Centrifuge suspension at 10,000×g and 4° C. for 20 minutes (use SS-34 rotor).
  d. Collect supernatant and keep on ice until Talon resin is prepared.
  e. Prepare polypropylene elution column by suspending column in the upright position; adding a few drops of wash buffer to a porous disc, then using reverse end of a Pasteur pipette to depress disc evenly to the bottom of the column.
  f. Prepare Talon resin by resuspending Talon resin by gently shaking; adding 3.5 ml of resin to each column, and once it has settled, breaking off cap/stopper from column; allowing resin to drip through into waste container until layers are visible; slowly adding 10 ml extraction buffer and collect flow-through into waste container, while not disturbing the resin or allowing it to dry.
  g. Add cell extract/supernatant to prepared Talon resin. Collect extract and repeat.
  h. Following second collection of cell extract flow-through, wash resin w/30 mL of wash buffer containing 20 mM Imidazole. (Talon resin should change hue to a pale pink color once the wash buffer has been added).
C. Collection of elution fraction:
  a. Add 1.5 mL of 50 mM imidazole in wash buffer and collect fraction.
  b. Add 1.5 mL of 100 mM imidazole in wash buffer and collect fraction.
  c. Add 1.5 mL (3×) 300 mM imidazole in wash buffer and collect fraction.

d. Add 20 μL PIC to each fraction of interest (particularly the 300 mM imidazole/wash fractions) and store at 4° C. (Imidazole solutions should be stored on ice prior to use.)

D. Quantification of protein in elution fractions (Bradford Assay-low concentration standard curve):
  a. Remove BSA-100 μg/mL from freezer (4° C.) and thaw on ice.
  b. Set up cuvettes for standard curve and add the specified amounts of both the thawed BSA/dH$_2$O from the below table.

| Final Conc. (μg/mL) | dH$_2$O (μL) | BSA-100 μg/mL (μL) |
|---|---|---|
| 0 | 200 | 0 |
| 0.25 | 197.5 | 2.5 |
| 0.5 | 195 | 5 |
| 1 | 190 | 10 |
| 2 | 180 | 20 |
| 4 | 160 | 40 |
| 8 | 120 | 80 | c. Add an additional cuvette or each fraction and dilute samples 1:50 20 μL sample+180 μL dH$_2$O).
  d. Prepare Bradford dye 1:4 in dH$_2$O (10 mL dye+30 mL dH$_2$O) and add 800 μL to each cuvette (final volume 1 mL).
  e. Mix cuvettes individually via inversion and incubate at RT for 15 minutes.
  f. After incubation, add 200 μL of the 0 μg/mL BSA standard in replicate to wells A1 and A2 of 96 well flat bottom plate followed by the addition 0.25 μg/mL BSA standard to B1 and B2. Continue to add the BSA standard in increasing concentration to the plate in the same order.
  g. Once the entirety of the BSA standard is added to the plate, load samples in replicate into the wells immediately below until no rows remain and then proceed to the top row of the next two columns.
  h. After all samples are loaded onto the plate read at 595 nm—"Low-conc. Std. Curve".
  i. Record the linear regression ($R^2$) and BSA standard curve values (Data obtained from assays with $R^2<0.95$ should not be used). Raw values for samples represent a 1:50 dilution and should therefore be multiplied by 50 to convert back into μg/mL. Once the concentrations of protein have been determined, fractions intended for plate coating (e.g., ELISA/ELISPOT), injection, etc. must be run on a 15% 2 mm SDS-PAGE gel to evaluate purity.

E. Identification of protein via SDS-PAGE gel Coomassie Blue staining:
  a. For each gel, wash 1× glass cover plate, 1× white aluminum backing plate, 2× black plate spacers, and 1× white 10 lane stacking comb with dH$_2$O. Rinse with 70% ethanol solution. Confirm that all solidified gel residue from previous use is removed before casting.
  b. After all materials have air-dried, take the backing plate and lay it flat on the bench top and place a spacer on each side of the plate before sandwiching with the clear glass cover plate. Confirm that the notches of the spacer are properly aligned to the edges of both plates.
  c. Loosen all screws on the casting block and slide the sandwiched plates with spacers into the caster. Confirm that all plates and spacer are even and aligned. Leave ~3 mm of the sandwiched plates protruding from the bottom of the casting block before carefully tightening the screws so as not to crack the plates.
  d. Place the casting block into the holder and set the black plastic plugs into the holder. Turn plugs to depress casting block into the black rubber mat of the holder. Confirm that the bottom of the plates is well sealed by the rubber of the holder in order to avoid leaks.
  e. Prepare separating/running gel according to the recipe below for a 15%-SDS PAGE gel and add solution to the cavity between aluminum backing plate and glass cover plate. Allow ~1.5-2 cm of space at the top of the sandwiched plates for stacking gel. Add ~1 mL of dH$_2$O to casting block. The gel will begin to polymerize once the APS/TEMED are added to the solution.

| Separating Gel | 15% |
|---|---|
| Acrylamide Bis 30% | 5 mL |
| Water (dH$_2$O) | 2.34 mL |
| 1.5 Tris Buffer pH 8.8 | 2.5 mL |
| SDS (10%) | 100 μL |
| APS (10%) | 50 μL |
| TEMED | 10 μL | f. Once the gel has hardened (~35 minutes), remove the layer of water and prepare the stacking gel solution from the recipe below. Add solution quickly.

| Stacking Gel | 15% |
|---|---|
| Acrylamide Bis 30% | 700 μL |
| Water (dH$_2$O) | 3.2 mL |
| 0.5 Tris Buffer pH 6.5 | 1250 μL |
| SDS (10%) | 50 μL |
| APS (10%) | 60 μL |
| TEMED | 20 μL | g. Immediately place the white 10 lane stacking comb into the stacking gel and allow to fully polymerize (about 10 minutes).
  h. Prepare samples to run on gel: (5 μg protein per well)
    i. If the fraction concentration is <165 μg/mL, use 22.5 μL of sample+7.5 μL 4× Sample Buffer;
    ii. If the fraction concentration is >165 μg/mL=>sample vol.=5 μg/((conc. (μg/mL)/1000)) & 4× Sample Buffer vol.=(⅓)*sample vol.
  i. Heat-inactivate all samples for 10 minutes @ 56° C. in the water bath.
  j. Remove 15% SDS-PAGE gel from casting block and attach to the running apparatus with 2× red clips. Fill the cavity of the running apparatus and the bottom tray with 1×SDS-PAGE running buffer. The stacking comb can now be removed. Add 10 μL of the Broad Range stained (P #26634) SPECTRA™ Multicolor Ladder to first well of the gel followed by 30 μL of the prepared samples to the subsequent wells.
  k. Once all samples are loaded, attach the electrodes to their appropriate terminals and turn on the power supply (red to red, black to black). Allow the gel to run at ~80-120 volts for 1.5-2.5 hours until the dye band runs off the bottom of the gel. At that point turn off the machine and disconnect the electrodes (Note: Lower voltages and lower time intervals increase the quality of the resulting gel.).

l. Drain the running buffer from the running apparatus. Remove the red clips, spacers, and gently detach the glass cover plate from the gel casting frame. Use the hard-plastic straight edge of the gel scraper to cleave the stacking gel off and into the trash. Divide gel as necessary for further assays, i.e. Western Blot, etc. . . . (It is not necessary to notch a corner of the gel to establish orientation because of the stained ladder used.).

m. For the separating gel that will be stained, wash 3×w/dH$_2$O for 15 minutes. Add ~25 mL of Coomassie Blue stain to the gel for 2+ hrs or O/N if necessary. Destain w/Coomassie Blue de-stain until optimal band color/gel transparency is obtained. Take a picture and save as JPG/TIF file.

Example 3: Generation of Recombinant Kex1 Proteins

Conserved Kex nucleotide sequences derived from fungal Kex genes of *Aspergillus fumigatus, Candida albicans, Cryptococcus neoformans* and *Pneumocystis hominis* (FIGS. 1A and 3) were synthesized and inserted into the expression vector pMAL-c4× using BamHI and HindIII restriction sites (GenScript). Each insert contained an N-terminal tobacco etch virus (TEV) cleavage site and an additional transcriptional start site (ATG) 5' to the conserved Kex sequences followed by two stop codons (AAG, CTT, ochre and opal, respectively). Plasmids were transformed into *Escherichia coli* BL21 (DE3) cells and plated on LB agar supplemented with 100 ug/ml ampicillin to select for transformed clones. For recombinant Kex proteins preparation, expression hosts were grown overnight with shaking at 37° C. in Luria broth (LB) supplemented with 100 μg/mL ampicillin and then sub-cultured 1:20 for 2 hours at 37° C., and protein expression was induced by the addition of 1 mM IPTG, with further incubation for 4 hours at 37° C. Expression of recombinant maltose binding protein (MBP)-tagged fusion proteins was confirmed by Western blotting using commercially available anti-MBP sera (New England Bio-Labs).

Harvested cells were then resuspended in 20 mM Tris-HCl, 300 mM NaCl, 1 mM EDTA, pH 8.0 with protease inhibitor cocktail (Sigma) and lysed through cell disruption. Supernatants were collected following centrifugation at 20,000×g for 30 minutes at 4° C. MBP-tagged proteins were purified by affinity chromatography using amylose resin (New England BioLabs). To cleave the ~42.5 kDa N-terminal MBP tag from recombinant Kex proteins, purified proteins were incubated with enhanced TEV protease (AcTEV, Invitrogen) at a 1:100 protease to target ratio for ~4 hours at 30° C. in a buffer containing 20 mM Tris-HCl, 300 mM NaCl, 1 mM EDTA, pH 8.0. Following TEV cleavage, each recombinant protein contained an additional N-terminal glycine and methionine due to the TEV cleavage motif and added transcriptional start site, respectively. Recombinant *Pneumocystis* KEX1 was expressed and purified as described in Example 2 above.

Example 4: Generation of Immune Sera

Immunization of Rhesus Macaque with Recombinant *Pneumocystis* KEX1 Peptide

An adult Rhesus macaque (monkey subject number 17911) was intramuscularly immunized with 100 μg of *Pneumocystis* KEX1 (purified as described in Example 2 above) and aluminum hydroxide (Imject Alum, Thermo Scientific) mixed in a 1:1 ratio and then boosted with 12 weeks later with 50 μg of KEX1 and alum. Plasma was collected 2 weeks after the boost, and heat-inactivated at 56° C. prior to use in immunoblotting. Plasma from a non-immunized monkey (monkey number 8015) was collected and used as a negative control. Reciprocal endpoint titers (RET) from monkey subject number 17911 two weeks post boost were >2×10$^6$. As used herein, reciprocal endpoint titer (RET) is the reciprocal of the highest analyte (e.g., antibody or antiserum) dilution that gives a reading above the cutoff value. Control plasma RET was <100, as determined by KEX1-specific ELISA, as described in Kling, H. M. and Norris, K. A., 2016, *J. Infect. Dis.*, 213, 1586-1595.

In determining antibody titers, in particular, anti-fungal KEX peptide antibodies, in human sera, normal human sera with undetectable absorbance at OD$_{450}$ (i.e., equal to or less than the absorbance measured at OD$_{450}$ for dilution buffer alone) in a KEX-ELISA assay at a dilution of 1:100 were used as negative controls. Based on the distribution of *Pneumocystis* KEX1 reciprocal endpoint antibody titers (RET) in human subjects, negative to low antibody titers range from about 1 to about 3200 RET, moderate levels range from about 3200 to about 12,800 RET, and high levels are >12,800 RET.

Example 5: Immunoblotting

*Pneumocystis* KEX1 Antisera Cross-Reactivity with Other Fungal KEX Recombinant Proteins To determine the nature of immunologic cross-reactivity among fungal KEX recombinant proteins, antisera from *Pneumocystis* KEX1 immunized monkeys were tested for reactivity by Western blotting using recombinant KEX proteins following purification and TEV cleavage of the fusion partner. Proteins were resolved by 15% SDS/PAGE and transferred to 0.2 μm nitrocellulose membranes. Membranes were then blocked overnight at 4° C. in 5% BSA/5% non-fat dry milk in PBS-T (0.05% Tween-20) and then incubated with high titer antiserum from monkey number 17911 (dilution 1:500) or low titer antiserum from monkey number 8015 (dilution 1:500) for 2 hours at room temperature to test for construct cross-reactivity. Blots were then incubated with secondary antibody goat anti-monkey IgG (H+L)-HRP (1:10,000) in blocking buffer for 1 hour at room temperature and visualized with SuperSignal West Pico Chemiluminescent Substrate (ThermoFisher). As a negative control, parallel blots were probed with secondary antibody only. The presence of maltose binding protein (MBP)-tagged proteins was confirmed by blotting with mouse anti-MBP antibody (1:10,000) (New England BioLabs, Ipswich, Mass.) and secondary antibody goat anti-mouse IgG immunoglobulin (H+L)-HRP (1:10,000) (ThermoFisher), FIGS. 4A-4D and FIGS. 5-5D.

Example 6: Kex Peptide Enzyme Linked Immunosorbent Assay (ELISA)

This example describes a protocol for performing an ELISA immunoassay utilizing a recombinantly produced (pET28b vector), Kex1 protein (peptide) that is histidine tagged and purified as described above in Example 2. The ELISA is conducted to detect (and quantify) the presence of anti-fungal Kex peptide antibodies in a sample, e.g., blood, plasma, serum, bronchoalveolar lavage, or biological fluid sample. The anti-Kex peptide antibodies to be detected (and quantified) can be directed against, reactive with and/or bind to the Kex peptide of one or more of the *Pneumocystis, Aspergillus, Candida,* or *Cryptococcus* Kex peptides.

Materials and Equipment
- A. KEX1 protein, which may be purified as described in Example 2
- B. 1×PBS
- C. Immulon high-binding (4HBX) Flat bottom microtiter plates (Thermo #3855)
- D. Blocking buffer: 5% skim milk in 1×PBS
- E. Wash buffer: 1× Phosphate-buffered Saline (PBS)+ 0.05% Tween-20
- F. Secondary Antibody: Goat anti-human immunoglobulin-conjugated horseradish peroxidase (1:10,000 for IgG; Sigma-Aldrich).
- G. Normal human plasma (Atlanta Biologicals, Inc., Lawrenceville, Ga.). Negative/normal control plasma with undetectable absorbance at $OD_{450}$ (i.e., equal to or less than dilution buffer alone) in KEX-ELISA at a dilution of 1:100 is used as negative controls.
- H. Substrate: 3,3′,5,5′-Tetramethylbenzidine (TMB) peroxidase substrate (such as SureBlue TMB substrate, 1-component; KPL, Inc.)
- I. Stop solution: 1 M $H_2SO_4$
- J. Adhesive sealing film for microplates (Plate sealers) (such as SealPlate non-sterile films from Excel Scientific, cat #100-SEAL-PLT)
- K. 96-well plate reader (any system capable of reading OD at a wavelength of 450 nm). The procedure for performing the ELISA is as follows:
- A. Coating/blocking ELISA plates with Kex1 protein:
  - a. Prepare mkKex protein in 1×PBS at 5 ug/mL. Add 50 µL of diluted KEX1 per well of Immulon 4HBX flat-bottom ELISA plates. Cover plates tightly with Parafilm or plate sealers and incubate O/N at 4° C.
  - b. Following overnight incubation, remove buffer by flicking into sink or bucket and tap plate onto absorbant pad or paper towels to remove excess. Wash plates 2× with wash buffer (PBS 0.05% Tween-20) (~200 uL wash buffer per well for each wash, flicking and tapping plate between washes).
  - c. Add 100 µL of blocking buffer (5% milk/PBS) to each well and incubate for 1 hour at 37° C.
  - d. Empty plates, wash 2× with wash buffer. The plates can be sealed and frozen at −20° C. at this step, until ready for use.
- B. Handling of plasma or other infectious fluids (e.g., bronchoalveolar lavage (BAL) fluid supernatant, etc.)—First-time use.
  - a. Remove plasma aliquot from −80° C. freezer.
  - b. Option 1: Heat-inactivate entire aliquot at 56° C. for 30 minutes.
    - Option 2: If heat inactivation of the plasma sample would be detrimental to other potential uses, thaw sample at 4° C. or on ice. Remove an aliquot (~100 uL), transfer to a new tube, and heat inactivate (30 min, 56° C.). Return the remaining sample to the −80° C. freezer, noting that it has been thawed 1×.
  - c. Centrifuge sample at >10,000 g for 1-2 minutes to pellet aggregates prior to use.
  - d. To prevent contamination in storage, add ~0.01 to 0.02% $NaN_3$. Store sample aliquot for up to 6 months at 4° C. For subsequent assays, no further heat inactivation is needed; however, the sample should be centrifuged briefly prior to each use.
- C. ELISA for endpoint titer determination (plasma):
  - a. Dilute plasma 1:100 in blocking buffer. Add 50 µL of diluted plasma and make serial 2× (or 4×, if needed) dilutions directly in the plate (final volume in each well should be 50 µL) for generation of endpoint titers (see, FIGS. 7A and 7B). Perform assay in duplicate; set up enough plates for all isotypes of interest, e.g., if there are 10 samples and endpoint titers are to be generated for both IgG and IgM-KEX1 antibodies, this would require setting up 4 plates (duplicate plates for both IgG and IgM). Include a negative/normal control on each plate. Cover plates with plate sealers and incubate O/N at 4° C.
  - b. Empty plate (flicking and tapping), wash 4× w/wash buffer.
  - c. Add 50 µL of secondary antibody (diluted in block) to each well (see appropriate dilutions under Materials and Equipment above). Incubate 1 hour at 37° C.
  - d. Empty the plate and wash 6× with wash buffer.
  - e. Add 100 µL of TMB to each well, protect from light and incubate for 30 minutes at 37° C.
  - f. Add 25-50 µL of stop solution (1 M $H_2SO_4$) to each well.
  - g. Read OD of plates (on any standard plate reader) at 450 nm within 20 minutes of adding stop solution.

The majority of healthy adults (both humans and non-human primates) have circulating antibodies to *Pneumocysti*; therefore, when selecting a control sample to be used for calculating endpoint titers, plasma samples must be screened from healthy donors to determine and obtain an appropriate control. In plasma from an appropriate normal/negative control, the KEX1 $OD_{450}$ at a 1:100 dilution should be not more than 0.1; however, the lower the OD of the normal/negative control plasma, the better the control is. To control for plate-to-plate variability, the same normal/negative control should be used on all plates following the selection of an appropriate normal/negative control.

Figure 7A:
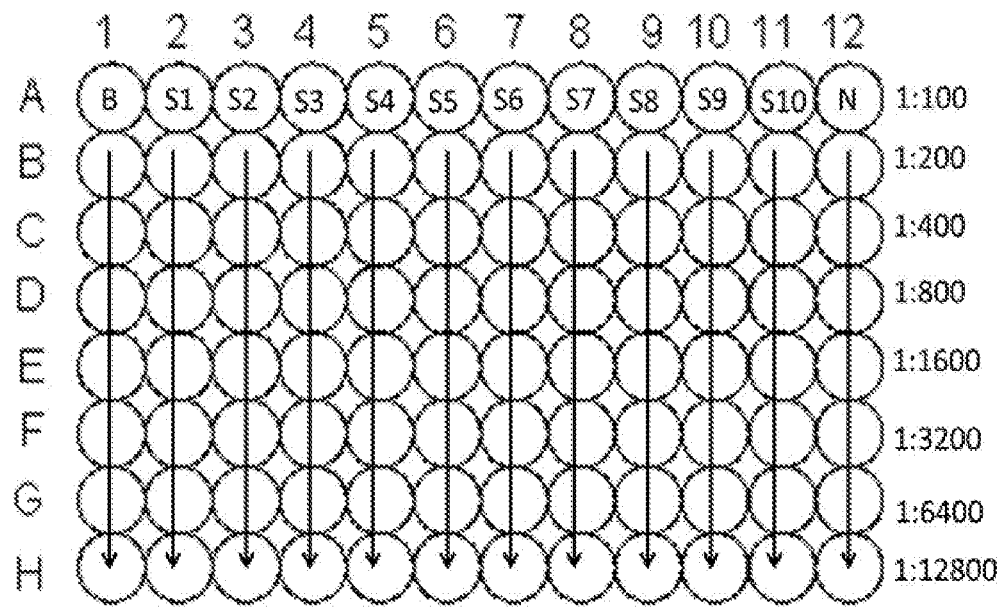
FIGS. 7A and 7B depict diagrams of template plates for performing an ELISA analysis as described in Example 6.
Figure 7B:
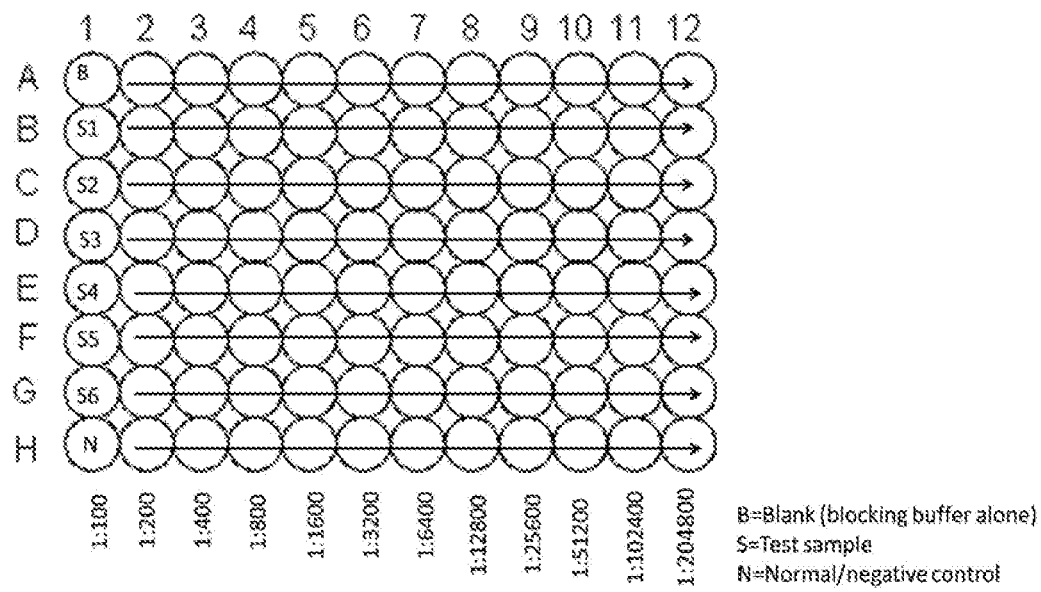

- D. ELISA for endpoint titer determination (BAL Supernatant).
  - a. Dilute BAL supernatant 1:100 in normal saline.
    - i. Determine the urea concentration of the BAL supernatant and corresponding plasma sample using QuantiChrom Urea assay (BioAssay Systems Cat #DIUR-500).
      1. Follow instructions on kit insert, diluting plasma 1:10 in distilled water and using BAL supernatant without dilution.
      2. Plate plasma samples in the wells of a 96 well plate adding 5 µL of standard (1:10 dilution), blank (distilled water) and sample (1:10 dilution) in duplicates.
      3. Plate BAL supernatant in the wells of a 96 well plate adding 50 µL of standard (diluted to 5 mg/dL), blank (distilled water) and sample (undiluted).
      4. Add 200 µL working reagent (included in kit) and tap lightly to mix.
      5. Incubate plasma plate for 20 minutes at room temperature (RT) and read at $OD_{520}$ on a spectrophotometer.
      6. Incubate BAL supernatant plate for 50 minutes at RT and read at $OD_{430}$.
      7. Calculate urea concentrations ([urea]) for plasma and BAL supernatant as follows: [urea]=(ODsample-ODblank)/(ODstandard-ODblank)*[standard]. The concentration of standard for plasma will be 50 mg/dL and will be 5 mg/dL for the BAL supernatant.
  8. Calculate 1:100 dilution of BAL supernatant as follows:
    a. Find the 1:100 dilution factor of bal to plasma
      i. Dilution factor=100/(plasma [urea]/bal [urea])
    b. Calculate volumes for dilution for 500 ul total sample
      i. Volume of sample=500 μL/dilution factor
      ii. Volume of saline=500 μL—volume of sample
  9. Add the volume of sample and volume of saline to make 1:100 diluted BAL supernatant sample.
  b. Add 50 μL of diluted BAL supernatant and make serial 2× (or 4×, if needed) dilutions directly in the plate with normal saline (final volume in each well should be 50 μL) for generation of endpoint titers (FIGS. 7A and 7B). Perform assay in duplicate; set up enough plates for all isotypes of interest, e.g., if there are 10 samples and endpoint titers are to be generated for both IgG and IgM-KEX1 antibodies, this would require setting up 4 plates (duplicate plates for both IgG and IgM). Include a negative/normal control in each plate, as described above. Cover plates with plate sealers and incubate O/N at 4° C.
  c. Empty plate (flicking and tapping), wash 4× with wash buffer.
  d. Add 50 μL of secondary antibody (diluted in block, see appropriate dilutions under Materials and Equipment) to each well. Incubate for 1 hour at 37° C.
  e. Empty the plate and wash 6× with wash buffer.
  f. Add 100 μL of TMB to each well, protect from light and incubate for 30 minutes at 37° C.
  g. Add 25-50 μL of stop solution (1 M $H_2SO_4$) to each well.
  h. Read OD of plates (on any standard plate reader) at 450 nm within 20 minutes of adding stop solution.
E. Determining Endpoint Titers.
  a. Plot OD readings from each sample (at all dilutions) in Excel, or similar program, as a line graph. For the normal/negative control sample, add 0.025 to each value prior to plotting as described below.
  b. The endpoint titer is defined by the dilution at which the test sample gives the same OD reading as that of the negative control (i.e., where the lines meet). Generally, the reciprocal endpoint titer is reported; thus, if the dilution is 1:1600, the endpoint titer is reported as 1600.
  c. Calculate endpoint titers from each of the duplicate plates, to confirm that the results are consistent between plates. Acceptable error is within one dilution. If reciprocal endpoint titers (RET) from duplicate plates fall within one dilution, average the titers (e.g., when doubling-dilutions are made, and a sample from plate 1 has a RET of 1600 and the RET from plate 2 is 3200, then the average titer is 2400). If endpoint titers on duplicate plates do not fall within one dilution of each other, repeat the ELISA on one additional plate and average the 2 values which are closest.

Figure 8:
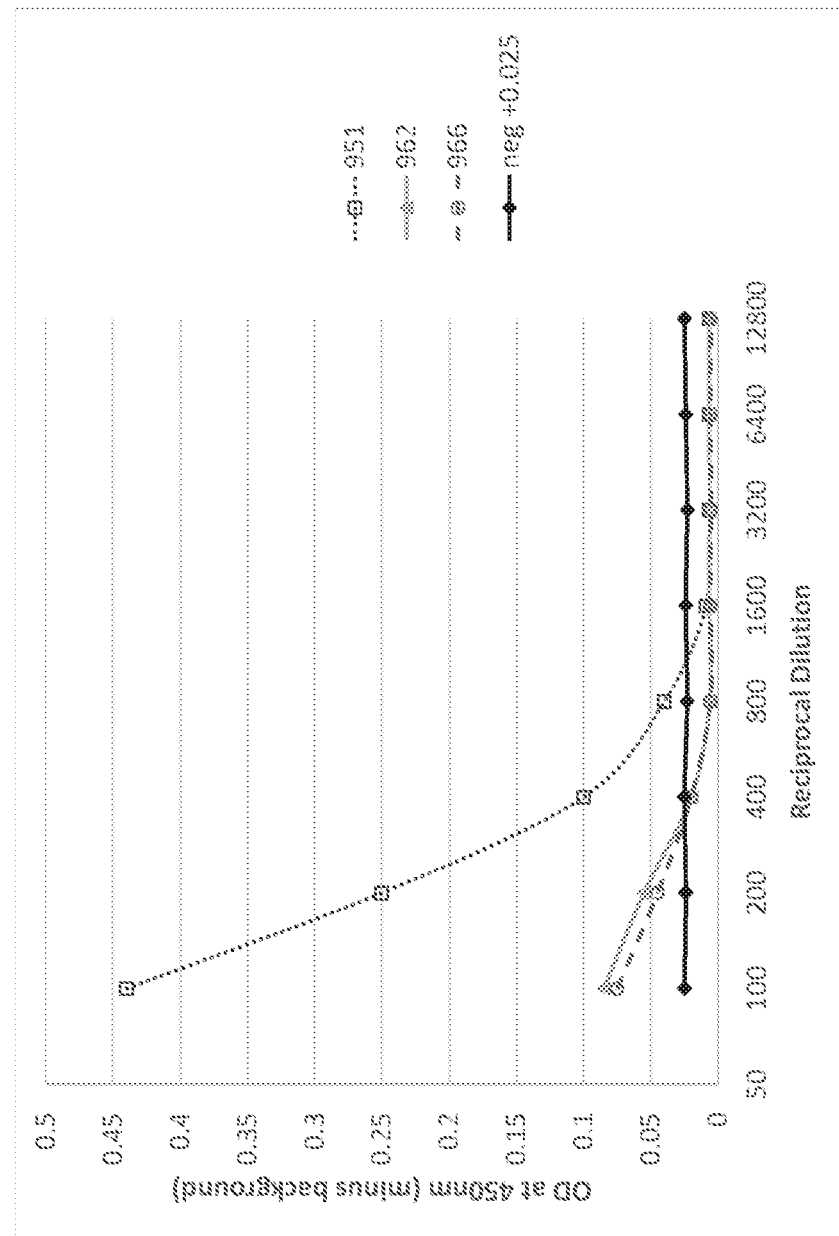
FIG. 8 shows a graph of a titer curve based on data obtained from the ELISA analysis performed as described in Example 6 and shown in the table therein. Reciprocal endpoint titers are estimated as follows: For sample #951, the endpoint titer value is 1200; for sample #962, the endpoint titer value is 350; and for sample #966, the endpoint titer value is 350.

By way of example, for determining an endpoint titer, the below table presents Optical Density 450 nm ($OD_{450}$) readings for each dilution (shown as its reciprocal) of a negative/normal control and three representative test samples (951, 962 and 966 in the table), e.g., serum samples. The original OD values for the control sample are plotted on the top row, followed by control values plus 0.025 for standardization of the plate (neg. ctrl.+0.025). These numbers are plotted in the graph shown in FIG. 8.

Absorbance Values (Optical Density 450 nm) of Serially Diluted Control and Experimental Samples

|  | Dilution (reciprocal) | | | | | | | |
|---|---|---|---|---|---|---|---|---|
|  | 100 | 200 | 400 | 800 | 1600 | 3200 | 6400 | 12800 |
| Negative control | 0.005714 | −0.00129 | −0.00329 | −0.00529 | −0.00529 | −0.00529 | −0.00629 | −0.00329 |
| Neg ctrl + 0.025 | 0.030714 | 0.023714 | 0.021714 | 0.019714 | 0.019714 | 0.019714 | 0.018714 | 0.021714 |
| Sample 951 | 0.442714 | 0.229714 | 0.096714 | 0.037714 | 0.011714 | 0.000714 | −0.00329 | −0.00329 |
| Sample 962 | 0.074714 | 0.037714 | 0.017714 | 0.006714 | 0.002714 | 0.000714 | −0.00029 | 0.000714 |
| Sample 966 | 0.086714 | 0.047714 | 0.013714 | 0.001714 | −0.00229 | −0.00429 | −0.00529 | −0.00429 |

Example 7: Anti-*Aspergillus* KEX Antibodies are Induced and Present in Antiserum in Animals Infected with *Aspergillus*

*Aspergillus* Asthma Model Antisera

Mouse sera from mice exposed to *Aspergillus fumigatus* were a gift from Dr. Chad Steele, University of Alabama. The sera were prepared as follows: C57BL/6 mice (Jackson Laboratories, Bar Harbor, Me.) were infected with *Aspergillus fumigatus* conidia as previously described by Lilly, L. M. et al., 2012, J Immunol., 189:3653-3660. Briefly, mice were lightly anesthetized with isoflurane and were administered intratracheally (i.t.) $1\times10^7$ live *Aspergillus fumigatus* conidia in a volume of 50 μL of PBS. Starting at day 7, mice were challenged it. with $1\times10^6$ live *A. fumigatus* conidia in 50 μL of PBS daily for 5 days, rested for 2 days, and challenged daily for another 3 days. At 24 hours after the final challenge, serum was collected from blood. Uninfected mice were purchased from Taconic Farms Incorporated (Germantown, N.Y.), and serum samples were collected as described above.

To determine whether the KEX antigen (AF_KexDS88) was an immunologic target during *Aspergillus* infection and to determine whether anti-sera from *Aspergillus fumigatus* infected mice recognized other fungal KEX species, *Aspergillus* KEX (AF_KexDS88, FIG. 3) was expressed in *E. coli* and purified. TEV cleaved proteins were resolved and transferred to nitrocellulose membranes as described above. Membranes were then blocked for 2 hours at room temperature with 2% BSA in PBS-T and then were incubated with sera from *Aspergillus*-infected and -uninfected mice in the indicated dilutions in blocking buffer overnight at room temperature with rocking. The blots were then incubated with secondary antibody, i.e., goat anti-mouse IgG antibody (H+L)-HRP (1:10,000 dilution), for 1 hour at room temperature and were visualized with SuperSignal West Femto Chemiluminescent Substrate (ThermoFisher). All blots were imaged with myECL imager (ThermoFisher), FIG. 6A.

To determine if *Aspergillus* KEX antibodies generated during infection immunologically cross reacted with fungal KEX peptides, recombinant kex peptides from *Pneumocystis*, *Candida albicans* and *Cryptococcus neoformans* were immunoblotted with sera from an *Aspergillus*-infected mouse at the dilution of 1:500. The blots were then incubated with goat anti-mouse IgG (H+L)-HRP secondary antibody (1:10,000) (ThermoFisher) and were visualized with SuperSignal West Pico Chemiluminescent Substrate (ThermoFisher). As shown by the Western blot in FIG. 6B, recombinant fungal KEX peptides (*) were recognized and bound by antibodies in sera (diluted 1:500) taken from *Aspergillus*-infected mice. The recombinant proteins were expressed as fusions with MBP (with (+) cleavage or without cleavage (−)) with TEV protease to release fungal peptides prior to resolution on 15% SDS-PAGE and immunoblotting. Shown in FIG. 6B is binding of the *Aspergillus*-infected mouse serum antibodies to the *Cryptococcus* KEX, *Aspergillus* KEX, *Candida* KEX, and *Pneumocystis* KEX1 peptides on the blot.

Figure 9:
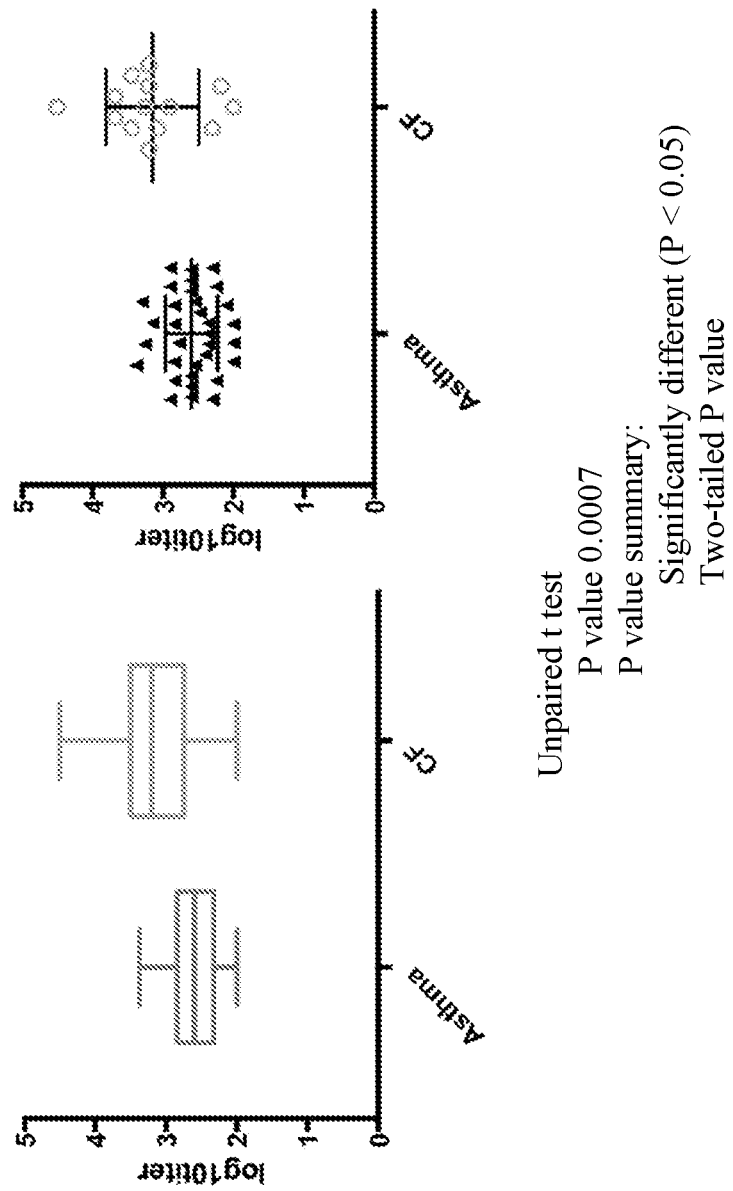
FIG. 9 presents graphs of the data observed in standard KEX1 ELISA analyses of sera obtained from a cohort or pediatric severe asthmatics and a cohort of pediatric cystic fibrosis patients.

Example 8: Severe Asthmatics have Lower KEX1 Titers Compared to Other Subjects with Severe Lung Disease Standard KEX1 ELISA were performed as described in Example 6 on sera collected from a cohort of pediatric patients with severe asthma and from a cohort of pediatric patients with cystic fibrosis (CF). Patients with severe asthma were more likely to have low or undetectable KEX1 titers than CF patients. Referring to FIG. 9, mean anti-KEX1 IgG serum titers observed in severe asthmatics were significantly lower than titers observed in CF patients. The present data suggest that low or undetectable titers to *Pneumocystis* KEX1 may be associated with severe asthma and that KEX1 antibodies play a role in protection against fungal colonization that can damage the lungs.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating or protecting a subject against disease or pathology caused by different fungal pathogens, the method comprising: administering to a subject in need thereof a Kexin peptide immunogen derived from the Kexin protein of a *Pneumocystis* fungal pathogen in an amount effective for the subject to generate an immune response against a kexin peptide of two or more of the *Pneumocystis, Aspergillus, Candida*, or *Cryptococcus* fungal pathogens, thereby treating or protecting the subject against disease or pathology caused by infection by the two or more different fungal pathogens; wherein the Kexin peptide immunogen administered to the subject has at least 95% amino acid sequence identity to SEQ ID NO: 1.

2. The method claim 1, wherein the treatment or protection is against disease or pathology associated with infection by two or more of *Aspergillus fumigatus, Candida albicans,* or *Cryptococcus neoformans*; and/or wherein the subject is treated or protected against a disease or pathology selected from pulmonary disease, poor pulmonary function, or a symptom thereof.

3. The method of claim 1, wherein the amount of the administered Kexin peptide immunogen is effective to induce antisera in the subject that is cross-reactive against the Kexin peptides of two or more of the *Pneumocystis, Aspergillus, Candida*, or *Cryptococcus* fungal pathogens.

4. The method of claim 3, wherein the Kexin peptide of *Pneumocystis* is a Kex1 peptide derived from *Pneumocystis hominis* or *Pneumocystis jirovecii*; wherein the Kexin peptide of *Candida* is a Kex1 peptide derived from *Candida albicans*; wherein the Kexin peptide of *Aspergillus* is a Kex1 peptide derived from *Aspergillus fumigatus*; and wherein the Kexin peptide of *Cryptococcus* is a Kex1 peptide derived from *Cryptococcus neoformans*.

5. The method of claim 1, wherein the Kexin peptide immunogen is encoded by a polynucleotide contained in an expression vector.

6. The method of claim 1, wherein the subject has or is at risk of having a disease or pathology caused by more than one fungal pathogen selected from *Pneumocystis, Aspergillus, Candida*, or *Cryptococcus*.

7. The method of claim 1, wherein the Kexin peptide immunogen comprises SEQ ID NO: 1.

8. The method of claim 6, wherein the subject is immunocompromised.

9. The method of claim 6, wherein the subject is treated for or protected from a disease or pathology selected from pulmonary disease, chronic obstructive pulmonary disease (COPD), poor pulmonary function, or a symptom thereof.

* * * * *

SEQUENCE LISTING

```
<160> NUMBER OF SEQ ID NOS: 15

<210> SEQ ID NO 1
<211> LENGTH: 90
<212> TYPE: PRT
<213> ORGANISM: Pneumocystis carinii

<400> SEQUENCE: 1

Asp Asp Asp Gly Lys Thr Val Asp Gly Pro Ser Pro Leu Val Leu Arg
1               5                   10                  15

Ala Phe Ile Asn Gly Val Asn Asn Gly Arg Asn Gly Leu Gly Ser Ile
            20                  25                  30

Tyr Val Phe Ala Ser Gly Asn Gly Gly Ile Tyr Asp Asp Asn Cys Asn
        35                  40                  45

Phe Asp Gly Tyr Ala Asn Ser Val Phe Thr Ile Thr Ile Gly Gly Ile
    50                  55                  60

Asp Lys His Gly Lys Arg Phe Ala Tyr Ser Glu Ala Cys Ser Ser Gln
65                  70                  75                  80

Leu Ala Val Thr Tyr Ala Gly Gly Ser Ala
                85                  90

<210> SEQ ID NO 2
<211> LENGTH: 270
<212> TYPE: DNA
<213> ORGANISM: Pneumocystis carinii

<400> SEQUENCE: 2
gatgacgatg gaaaaaccgt tgatgggcct tctcctcttg ttcttagagc atttattaat      60
ggagtaaata atgggaggaa tgggttgggt tctatctatg tttttgcatc aggaaatggc     120
ggaatatacg atgacaactg taattttgat ggatatgcaa atagcgtgtt tactattact     180
```

```
attggtggta tagataaaca cggaaagcgc tttgcatatt ctgaagcgtg ttcttctcag        240
ttagctgtta catatgcagg cggaagtgca                                        270
```

<210> SEQ ID NO 3
<211> LENGTH: 844
<212> TYPE: PRT
<213> ORGANISM: Aspergillus fumigatus

<400> SEQUENCE: 3

```
Met Arg Phe Leu Gly Ser Ile Ala Leu Val Leu Ser Ser Ile Ser Val
1               5                   10                  15

Ala Ser Ala Asn Val Arg Ser Arg Ser Tyr Asp Thr His Glu Phe Phe
            20                  25                  30

Ala Leu His Leu Asp Asp Ser Ala Ser Pro Ser His Val Ala Gln Leu
        35                  40                  45

Leu Gly Ala Arg His Glu Gly Gln Ile Gly Glu Leu Ala Asn His His
    50                  55                  60

Thr Phe Ser Ile Pro Arg Glu Arg Ser Ser Asp Leu Asp Ala Leu Leu
65                  70                  75                  80

Glu Arg Ala Arg Ala Ala Arg Lys Ile Arg Arg Ala Arg Asp Asp
                85                  90                  95

Ala Thr Ser Gln Glu Gln His Asn Asp Ala Leu Gly Gly Ile Leu Trp
            100                 105                 110

Ser Gln Lys Leu Ala Pro Lys Lys Arg Leu Val Lys Arg Val Pro Pro
        115                 120                 125

Pro Glu Arg Leu Ala Arg Thr Phe Ala Thr Gly Lys Glu Asp Pro Val
    130                 135                 140

Ala Ala Gln Ser Gln Lys Arg Ile Ala Ser Thr Leu Gly Ile Thr Asp
145                 150                 155                 160

Pro Ile Phe Asn Gly Gln Trp His Leu Phe Asn Thr Val Gln Leu Gly
                165                 170                 175

His Asp Leu Asn Val Thr Gly Val Trp Met Glu Gly Ile Thr Gly Lys
            180                 185                 190

Gly Val Thr Thr Ala Val Val Asp Asp Gly Leu Asp Met Tyr Ser Asn
        195                 200                 205

Asp Leu Lys Pro Asn Tyr Phe Pro Glu Gly Ser Tyr Asp Phe Asn Asp
    210                 215                 220

His Thr Pro Glu Pro Arg Pro Arg Leu Ser Asp Lys His Gly Thr
225                 230                 235                 240

Arg Cys Ala Gly Glu Ile Ala Ala Arg Asn Asp Val Cys Gly Val
                245                 250                 255

Gly Val Ala Tyr Asp Ser Arg Val Ala Gly Val Arg Ile Leu Ser Lys
            260                 265                 270

Ala Ile Asp Asp Ala Asp Glu Ala Thr Ala Ile Asn Phe Ala Tyr Gln
        275                 280                 285

Glu Asn Asp Ile Phe Ser Cys Ser Trp Gly Pro Pro Asp Gly Ala
    290                 295                 300

Thr Met Glu Gly Pro Gly Ile Leu Ile Lys Arg Ala Phe Val Asn Gly
305                 310                 315                 320

Val Gln Asn Gly Arg Gly Lys Gly Ser Ile Phe Val Phe Ala Ala
                325                 330                 335

Gly Asn Gly Ala Ser Phe Glu Asp Asn Cys Asn Phe Asp Gly Tyr Thr
            340                 345                 350
```

```
Asn Ser Ile Tyr Ser Ile Thr Val Gly Ala Ile Asp Arg Glu Gly Asn
            355                 360                 365

His Pro Ser Tyr Ser Glu Ser Cys Ser Ala Gln Leu Val Val Ala Tyr
        370                 375                 380

Ser Ser Gly Ser Gly Asp Ala Ile His Thr Thr Asp Val Gly Thr Asp
385                 390                 395                 400

Lys Cys Tyr Ser Phe His Gly Thr Ser Ala Ala Gly Pro Leu Ala
                405                 410                 415

Ala Gly Thr Val Ala Leu Ala Leu Ser Ala Arg Pro Glu Leu Thr Trp
            420                 425                 430

Arg Asp Ala Gln Tyr Leu Met Val Glu Thr Ala Val Pro Ile His Glu
        435                 440                 445

Asp Asp Gly Ser Trp Gln Val Thr Lys Ala Gly Arg Lys Phe Ser His
    450                 455                 460

Asp Trp Gly Tyr Gly Lys Val Asp Ala Tyr Ala Leu Val Gln Lys Ala
465                 470                 475                 480

Lys Thr Trp Glu Leu Val Lys Pro Gln Ala Trp Phe His Ser Pro Trp
                485                 490                 495

Leu Arg Val Gln His Lys Val Pro Gln Gly Asp Gln Gly Leu Ala Ser
            500                 505                 510

Ser Tyr Glu Val Thr Glu Gln Met Met Lys Asn Ala Asn Ile Ala Arg
        515                 520                 525

Leu Glu His Val Thr Val Thr Met Asn Val Asn His Thr Arg Arg Gly
    530                 535                 540

Asp Leu Ser Val Glu Leu Arg Ser Pro Glu Gly Ile Val Ser His Leu
545                 550                 555                 560

Ser Thr Thr Arg Lys Ser Asp Asn Glu Lys Ala Gly Tyr Val Asp Trp
                565                 570                 575

Thr Phe Met Thr Val Ala His Trp Gly Glu Ser Gly Val Gly Arg Trp
            580                 585                 590

Thr Val Ile Val Lys Asp Thr Asn Val Asn Glu Phe Thr Gly Glu Phe
        595                 600                 605

Ile Asp Trp Arg Leu Asn Leu Trp Gly Glu Ala Ile Asp Gly Ala Asn
    610                 615                 620

Gln Lys Pro His Pro Phe Pro Asp Glu His Asp Asp His Ser Ile
625                 630                 635                 640

Glu Asp Ala Ile Val Ala Thr Thr Ser Val Glu Thr Gly Pro Thr Lys
                645                 650                 655

Thr Gly Val Pro Gly Ser Thr Asp Asp Thr Ile Asn Arg Pro Val Asn
            660                 665                 670

Ala Lys Pro Val Glu Thr Gln Thr Pro Ser Pro Ala Glu Thr Thr Ala
        675                 680                 685

Thr Lys Leu Ala Pro Pro Ala Glu Thr Arg Pro Ala Ala Thr Ala Thr
    690                 695                 700

Ser Ser Pro Thr Pro Pro Ala Ser Asp Ser Phe Leu Pro Ser Phe
705                 710                 715                 720

Met Pro Thr Phe Gly Ala Ser Lys Arg Thr Gln Ile Trp Ile Tyr Ala
                725                 730                 735

Ala Ile Gly Ser Ile Ile Val Phe Cys Ile Gly Leu Gly Ile Tyr Phe
            740                 745                 750

Gln Val Gln Arg Arg Lys Arg Ile Leu Asn Asn Pro Arg Asp Asp Tyr
        755                 760                 765

Asp Phe Glu Met Ile Glu Asp Glu Asn Ala Leu His Gly Gly Asn Gly
```

```
                    770                 775                 780
Arg Ser Gly Arg Thr Gln Arg Arg Gly Gly Glu Leu Tyr Asn Ala Phe
785                 790                 795                 800

Ala Gly Glu Ser Asp Glu Glu Pro Leu Phe Ser Asp Glu Asp Asp
                805                 810                 815

Glu Pro Tyr Arg Asp Arg Ala Pro Ser Glu Asp Arg Leu Arg Asp Thr
                820                 825                 830

Ser Ser Asp Asp Arg Ser Leu Arg His Gly Asp His
            835                 840

<210> SEQ ID NO 4
<211> LENGTH: 924
<212> TYPE: PRT
<213> ORGANISM: Candida albicans

<400> SEQUENCE: 4

Met Leu Pro Ile Lys Leu Leu Ile Phe Ile Leu Gly Tyr Leu Leu Ser
1               5                   10                  15

Pro Thr Leu Gln Gln Tyr Gln Gln Ile Pro Pro Arg Asp Tyr Glu Asn
                20                  25                  30

Lys Asn Tyr Phe Leu Val Glu Leu Asn Thr Thr Asn Ser Gln Lys Pro
            35                  40                  45

Leu Ile Asp Phe Ile Ser His Tyr Arg Gly His Tyr Asn Phe Glu His
50                  55                  60

Gln Leu Ser Ser Leu Asp Asn His Tyr Val Phe Ser Ile Asp Lys Ser
65                  70                  75                  80

His Pro His Asn Ser Phe Leu Gly Asn His Asn Ser Asn Glu Tyr Asn
                85                  90                  95

Leu Met Lys Arg Gln Leu Gly His Glu Gln Asp Tyr Asp Glu Leu Ile
            100                 105                 110

Ser His Val Glu Ser Ile His Leu Leu Pro Met Lys Lys Leu Ser Lys
        115                 120                 125

Arg Ile Pro Val Pro Ile Glu Met Glu Asp Val Val Phe Asp Asn Arg
130                 135                 140

Asp Asp Thr Gly Ser Asp Asn His Glu Ala Thr Asp Glu Ala His Gln
145                 150                 155                 160

Lys Leu Ile Glu Ile Ala Lys Lys Leu Asp Ile His Asp Pro Glu Phe
                165                 170                 175

Thr Thr Gln Trp His Leu Ile Asn Leu Lys Tyr Pro Gly His Asp Val
            180                 185                 190

Asn Val Thr Gly Leu Trp Leu Glu Asp Ile Leu Gly Gln Gly Ile Val
        195                 200                 205

Thr Ala Leu Val Asp Asp Gly Val Asp Ala Glu Ser Asp Asp Ile Lys
210                 215                 220

Gln Asn Phe Asn Ser Glu Gly Ser Trp Asp Phe Asn Asn Lys Gly Lys
225                 230                 235                 240

Ser Pro Leu Pro Arg Leu Phe Asp Asp Tyr His Gly Thr Arg Cys Ala
                245                 250                 255

Gly Glu Ile Ala Ala Val Lys Asn Asp Val Cys Gly Ile Gly Val Ala
            260                 265                 270

Trp Lys Ser Gln Val Ser Gly Ile Arg Ile Leu Ser Gly Pro Ile Thr
        275                 280                 285

Ser Ser Asp Glu Ala Glu Ala Met Val Tyr Gly Leu Asp Thr Asn Asp
290                 295                 300
```

```
Ile Tyr Ser Cys Ser Trp Gly Pro Thr Asp Asn Gly Lys Val Leu Ser
305                 310                 315                 320

Glu Pro Asp Val Ile Val Lys Lys Ala Met Ile Lys Gly Ile Gln Glu
            325                 330                 335

Gly Arg Asp Lys Lys Gly Ala Ile Tyr Val Phe Ala Ser Gly Asn Gly
            340                 345                 350

Gly Arg Phe Gly Asp Ser Cys Asn Phe Asp Gly Tyr Thr Asn Ser Ile
            355                 360                 365

Tyr Ser Ile Thr Val Gly Ala Ile Asp Tyr Lys Gly Leu His Pro Gln
370                 375                 380

Tyr Ser Glu Ala Cys Ser Ala Val Met Val Thr Tyr Ser Ser Gly
385                 390                 395                 400

Ser Gly Glu His Ile His Thr Thr Asp Ile Lys Lys Cys Ser Ala
            405                 410                 415

Thr His Gly Gly Thr Ser Ala Ala Ala Pro Leu Ala Ser Gly Ile Tyr
            420                 425                 430

Ser Leu Ile Leu Ser Ala Asn Pro Asn Leu Thr Trp Arg Asp Val Gln
            435                 440                 445

Tyr Ile Ser Val Leu Ser Ala Thr Pro Ile Asn Glu Glu Asp Gly Asn
450                 455                 460

Tyr Gln Thr Thr Ala Leu Asn Arg Lys Tyr Ser His Lys Tyr Gly Tyr
465                 470                 475                 480

Gly Lys Thr Asp Ala Tyr Lys Met Val His Phe Ala Lys Thr Trp Val
            485                 490                 495

Asn Val Lys Pro Gln Ala Trp Tyr Tyr Ser Asp Ile Ile Glu Val Asn
            500                 505                 510

Gln Thr Ile Thr Thr Thr Pro Glu Gln Lys Ala Pro Ser Lys Arg Asp
            515                 520                 525

Ser Pro Gln Lys Ile Ile His Ser Val Asn Val Ser Glu Lys Asp
530                 535                 540

Leu Lys Ile Met Asn Val Glu Arg Val Glu His Ile Thr Val Lys Val
545                 550                 555                 560

Asn Ile Asp Ser Thr Tyr Arg Gly Arg Val Gly Met Arg Ile Ile Ser
            565                 570                 575

Pro Thr Gly Val Ile Ser Asp Leu Ala Thr Phe Arg Val Asn Asp Ala
            580                 585                 590

Ser Thr Arg Gly Phe Gln Asn Trp Thr Phe Met Ser Val Ala His Trp
            595                 600                 605

Gly Glu Thr Gly Ile Gly Glu Trp Lys Val Glu Val Phe Val Asp Asp
610                 615                 620

Ser Lys Gly Asp Gln Val Glu Ile Asn Phe Lys Asp Trp Gln Phe Arg
625                 630                 635                 640

Ile Phe Gly Glu Ser Ile Asp Gly Asp Lys Ala Glu Val Tyr Asp Ile
            645                 650                 655

Thr Lys Asp Tyr Ala Ala Ile Arg Arg Glu Leu Leu Glu Lys Glu Lys
            660                 665                 670

Gln Asn Ser Lys Ser Thr Thr Thr Thr Ser Ser Thr Thr Thr Ala Thr
            675                 680                 685

Thr Thr Ser Gly Gly Glu Gly Asp Gln Lys Thr Thr Thr Ser Ala Glu
            690                 695                 700

Asn Lys Glu Ser Thr Thr Lys Val Asp Asn Ser Ala Ser Ile Thr Thr
705                 710                 715                 720

Ser Gln Thr Ala Ser Leu Thr Ser Ser Asn Glu Gln His Gln Pro Thr
```

```
                        725                 730                 735
Glu Ser Asn Ser Asp Ser Asp Ser Asp Thr Asp Asp Glu Asn Lys Gln
            740                 745                 750
Glu Gly Glu Glu Asp Asn Asp Asn Asp Asn Asp Gly Asn Lys Lys
            755                 760                 765
Ala Asn Ser Asp Asn Thr Gly Phe Tyr Leu Met Ser Ile Ala Val Val
    770                 775                 780
Gly Phe Ile Ala Val Leu Leu Val Met Lys Phe His Lys Thr Pro Gly
785                 790                 795                 800
Ser Gly Arg Arg Arg Arg Arg Arg Asp Gly Tyr Glu Phe Asp Ile Ile
            805                 810                 815
Pro Gly Glu Asp Tyr Ser Asp Ser Asp Asp Glu Asp Asp Ser Asp
            820                 825                 830
Thr Arg Arg Ala Asp Asp Asp Ser Phe Asp Leu Gly His Arg Asn Asp
            835                 840                 845
Gln Arg Val Val Ser Ala Ser Gln Gln Gln Arg Gln Tyr Asp Arg Gln
    850                 855                 860
Gln Asp Glu Ala Arg Asp Arg Leu Phe Asp Asp Phe Asn Ala Glu Ser
865                 870                 875                 880
Leu Pro Asp Tyr Glu Asn Asp Met Phe Lys Ile Gly Asp Glu Glu Glu
                885                 890                 895
Glu Glu Glu Glu Glu Glu Glu Gly Gln Gln Ser Ala Lys Ala Pro Ser
            900                 905                 910
Asn Ser Glu Gly Asn Ser Gly Thr Ser Thr Lys Lys
            915                 920

<210> SEQ ID NO 5
<211> LENGTH: 917
<212> TYPE: PRT
<213> ORGANISM: Cryptococcus neoformans

<400> SEQUENCE: 5

Met Arg Thr Leu Leu Ser Leu Trp Gly Ile Leu Leu Ala Leu Ile Val
1               5                   10                  15
Pro Pro Ser Leu Ala Leu Gln Arg Pro Gln Pro Arg Ser Tyr Asp Thr
            20                  25                  30
His Ala Tyr Tyr Ala Leu Glu Leu Asp Pro Ser Ile Ser Pro Ala Ala
        35                  40                  45
Ala Leu Gln Leu Ser Lys Ser Leu Gly Val Glu Leu Val Glu Arg Ile
    50                  55                  60
Gly Glu Leu Asp Gly His Trp Leu Val Arg Thr Glu Gly Trp Thr Pro
65                  70                  75                  80
Glu His Ala Ser Ile Thr Lys Arg Ser Val Ser His Asp Pro Ile Leu
                85                  90                  95
Lys Arg Trp Glu Ala Leu Pro Ser Ser Leu Gly Lys Lys Ser Leu Thr
            100                 105                 110
Pro Leu Ser Leu Lys Gln Arg Ala Lys Arg His Lys Ser Tyr Ser Pro
        115                 120                 125
Arg Ser Arg His Ser Arg Asp Asp Arg Thr Glu Leu Leu Tyr Ala Gln
    130                 135                 140
Asn Glu Leu His Leu Ala Asp Pro Met Leu Asp Gln Gln Trp His Leu
145                 150                 155                 160
Ile Asn Thr Gln Met Lys Asp Ile Glu Leu Asn Val Thr Gly Leu Trp
                165                 170                 175
```

```
Gly Arg Gly Ile Thr Gly Glu Gly Val His Val Ile Ile Asp Asp
            180                 185                 190

Gly Leu Asp Val Glu Ser Lys Asp Leu Lys Asp Asn Phe Phe Ala Glu
            195                 200                 205

Gly Ser Tyr Asp Phe Asn Asp His Thr Glu Leu Pro Ile Pro Arg Leu
            210                 215                 220

Lys Asp Asp Gln His Gly Thr Arg Cys Ala Gly Glu Ile Ala Ala Val
225                 230                 235                 240

Pro Asn Asp Val Cys Gly Val Gly Val Ala Tyr Asp Ser Lys Ile Ala
            245                 250                 255

Gly Val Arg Ile Leu Ser Ala Pro Ile Ser Asp Ala Asp Glu Ala Ala
            260                 265                 270

Ala Leu Asn Tyr Ala Tyr Gln Leu Asn Asp Ile Tyr Ser Cys Ser Trp
            275                 280                 285

Gly Pro Pro Asp Asp Gly Arg Ser Met Glu Ala Pro Asp Gly Leu Ile
            290                 295                 300

Leu Lys Ala Met Val Asn Gly Val Gln Lys Gly Arg Asp Gly Lys Gly
305                 310                 315                 320

Ser Val Phe Val Phe Ala Ala Gly Asn Gly Gly Ser Asp Asp Gln
            325                 330                 335

Cys Asn Phe Asp Gly Tyr Thr Asn Ser Ile Phe Ser Val Thr Val Gly
            340                 345                 350

Ala Val Asp Arg Lys Gly Leu His Pro Tyr Tyr Ser Glu Met Cys Ala
            355                 360                 365

Ala Met Met Val Val Ala Pro Ser Ser Gly Ser Gly Asp His Ile His
            370                 375                 380

Thr Thr Asp Val Gly Lys Asp Lys Cys Ser His Ser His Gly Gly Thr
385                 390                 395                 400

Ser Ala Ala Ala Pro Leu Ala Val Gly Val Phe Ala Leu Ala Leu Ser
            405                 410                 415

Val Arg Pro Asp Leu Thr Trp Arg Asp Ile Gln His Leu Ala Val Arg
            420                 425                 430

His Ala Val Phe Phe Asn Pro Asp Asp Pro Ala Trp Glu Leu Thr Ala
            435                 440                 445

Ala Gly Arg His Phe Ser Tyr Lys Tyr Gly Tyr Gly Lys Leu Asp Ala
            450                 455                 460

Gly Leu Phe Val Glu Ala Ala Glu Lys Trp Gln Leu Val Lys Pro Gln
465                 470                 475                 480

Thr Trp Tyr Asp Ser Pro Ser Val Tyr Leu Pro Thr Thr Ser Pro Ala
            485                 490                 495

Asp Val Thr Arg Arg Gln Asp Glu Ala Ala Asp Gly Pro Thr Ser Ser
            500                 505                 510

Asp Glu Glu Thr Ser Asn Pro Pro Val Val Glu Pro Ser Gly Ser
            515                 520                 525

Phe Ile Thr Glu Asp Gly Val Ile Ser Thr Tyr Glu Val Thr Gln Ser
            530                 535                 540

Met Leu Phe Asp Ala Asn Phe Glu Arg Leu Glu His Val Thr Val Arg
545                 550                 555                 560

Val Trp Ile Asp His Gln Arg Arg Gly Asp Val Glu Val Glu Leu Thr
            565                 570                 575

Ser Pro Asn Gly Val Val Ser Val Leu Cys Arg Gln Arg Arg Phe Asp
            580                 585                 590

Asn Ala Asp Ser Gly Phe Pro Gly Trp Lys Phe Met Ser Leu Lys His
```

```
                595                 600                 605
Trp Asp Glu Asn Pro Val Gly Thr Trp Thr Ile Lys Val Lys Asp Gln
610                 615                 620

Val Asn Pro Asp Lys Thr Gly Arg Phe Val Ala Trp Ser Leu Gln Leu
625                 630                 635                 640

Trp Gly Glu Ser Val Asp Pro Ala Leu Ala Lys Leu Trp Ala Pro Ala
                645                 650                 655

Glu Glu Gly Gln Pro Asp Glu Glu Gln Thr Gly Ser Asn Pro Ser Thr
            660                 665                 670

Thr Val Ser Gln Lys Pro Lys Pro Thr Ala Leu Leu Pro Gly Asp His
        675                 680                 685

Gly Glu Ala Ser Gly Glu Ala Thr Gln Pro Gly Leu Gly Ser Ala Thr
690                 695                 700

Ala His Pro Gln Pro Thr Ser Thr Thr Gly Asp Ala Gly Asn Val Ala
705                 710                 715                 720

Glu Pro Thr Gly Pro Thr Asp Ala Asp Ala Asp Glu Gly Phe Phe Ser
                725                 730                 735

Gly Ile Ser Asn Leu Ala Ser Ser Thr Trp Leu Ala Gly Ala Gly
            740                 745                 750

Ala Ile Ile Ile Leu Ser Gly Ala Ala Ile Gly Ala Phe Phe Ile
        755                 760                 765

Arg Ala Arg Arg Gln Lys Arg Asn Leu Phe Gly Leu Ser Asn Asn Gly
770                 775                 780

Gln Gly Ala Arg Gly Ala Tyr Glu Pro Val Asp Asp Val Gln Met Ser
785                 790                 795                 800

Leu Leu Glu Arg Gly Arg Arg Lys Phe Gly Lys Ser Lys Ser Glu Ser
                805                 810                 815

Gln Gly Thr Lys Asp Leu Tyr Asp Ala Phe Gly Asp Gly Pro Ser Asp
            820                 825                 830

Glu Glu Glu Glu Asp Leu Asp Glu Arg Thr Ala Leu Arg Tyr His Asp
        835                 840                 845

Gly Phe Leu Glu Asp Asp Glu Pro Asn Glu Val Gly Pro Lys Thr Glu
850                 855                 860

Tyr Lys Asp Glu Pro Glu Ser Glu Pro Glu Thr Phe Lys Asp Gly Glu
865                 870                 875                 880

Glu Thr Val Gly Thr Lys Asp Lys Gly Lys Gly Lys Gly Pro Ser Glu
                885                 890                 895

Gly Glu Ser Gly Ser Gly Ser Ser Ser Ser Trp Gln Asp Ala Ala Asp
            900                 905                 910

Glu Glu Ala Arg Val
        915

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp His Ile His Thr Thr Asp Val Gly Lys Asp Lys Cys Ser His Ser
1               5                   10                  15

His Gly Gly Thr Ser Ala Ala Ala Pro Leu Ala Val
            20                  25
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Asp Asp Gly Lys Thr Val Asp Gly Pro Ser Ser Leu Val Leu Arg
1               5                   10                  15

Ala Leu Ile Asn Gly Val Asn Asn Gly Arg Asn Gly Leu Gly Ser Ile
            20                  25                  30

Tyr Val Phe Ala Ser Gly Asn Gly Ile Tyr Glu Asp Asn Cys Asn
        35                  40                  45

Phe Asp Gly Tyr Ala Asn Ser Val Phe Thr Ile Thr Ile Gly Gly Ile
    50                  55                  60

Asp Lys His Gly Lys Arg Leu Lys Tyr Ser Glu Ala Cys Ser Ser Gln
65                  70                  75                  80

Leu Ala Val Thr Tyr Ala Gly Gly Ser Ala
                85                  90

<210> SEQ ID NO 9
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Asp Asp Gly Lys Thr Val Asp Gly Pro Ser Pro Leu Val Leu Arg
1               5                   10                  15

Ala Phe Ile Asn Gly Val Asn Asn Gly Arg Asn Gly Leu Gly Ser Ile
            20                  25                  30

Tyr Val Phe Ala Ser Gly Asn Gly Ile Tyr Asp Asp Asn Cys Asn
        35                  40                  45

Phe Asp Gly Tyr Ala Asn Ser Val Phe Thr Ile Thr Ile Gly Gly Ile
    50                  55                  60

Asp Lys His Gly Lys Arg Phe Ala Tyr Ser Glu Ala Cys Ser Ser Gln
65                  70                  75                  80

Leu Ala Val Thr Tyr Ala Gly Gly Ser Ala
                85                  90

<210> SEQ ID NO 10
<211> LENGTH: 90
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 10

Pro Asp Asp Gly Ala Thr Met Glu Gly Pro Gly Ile Leu Ile Lys Arg
1               5                  10                  15

Ala Phe Val Asn Gly Val Gln Asn Gly Arg Gly Gly Lys Gly Ser Ile
            20                  25                  30

Phe Val Phe Ala Ala Gly Asn Gly Ala Ser Phe Glu Asp Asn Cys Asn
        35                  40                  45

Phe Asp Gly Tyr Thr Asn Ser Ile Tyr Ser Ile Thr Val Gly Ala Ile
    50                  55                  60

Asp Arg Glu Gly Asn His Pro Ser Tyr Ser Glu Ser Cys Ser Ala Gln
65                  70                  75                  80

Leu Val Val Ala Tyr Ser Ser Gly Ser Gly
                85                  90

<210> SEQ ID NO 11
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Asp Asp Gly Arg Ser Met Glu Ala Pro Asp Gly Leu Ile Leu Lys
1               5                  10                  15

Ala Met Val Asn Gly Val Gln Lys Gly Arg Asp Gly Lys Gly Ser Val
            20                  25                  30

Phe Val Phe Ala Ala Gly Asn Gly Gly Ser Asp Asp Gln Cys Asn
        35                  40                  45

Phe Asp Gly Tyr Thr Asn Ser Ile Phe Ser Val Thr Val Gly Ala Val
    50                  55                  60

Asp Arg Lys Gly Leu His Pro Tyr Tyr Ser Glu Met Cys Ala Ala Met
65                  70                  75                  80

Met Val Val Ala Pro Ser Ser Gly Ser Gly
                85                  90

<210> SEQ ID NO 12
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Asp Asn Gly Lys Val Leu Ser Glu Pro Asp Val Ile Val Lys Lys
1               5                  10                  15

Ala Met Ile Lys Gly Ile Gln Glu Gly Arg Asp Lys Lys Gly Ala Ile
            20                  25                  30

Tyr Val Phe Ala Ser Gly Asn Gly Gly Arg Phe Gly Asp Ser Cys Asn
        35                  40                  45

Phe Asp Gly Tyr Thr Asn Ser Ile Tyr Ser Ile Thr Val Gly Ala Ile
    50                  55                  60

Asp Tyr Lys Gly Leu His Pro Gln Tyr Ser Glu Ala Cys Ser Ala Val
65                  70                  75                  80

Met Val Val Thr Tyr Ser Ser Gly Ser Gly
                85                  90

<210> SEQ ID NO 13
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Asp Gly Ala Thr Met Glu Gly Pro Gly Ile Leu Ile Lys Arg Ala
1               5                   10                  15

Phe Val Asn Gly Val Gln Asn Gly Arg Gly Gly Lys Gly Ser Ile Phe
            20                  25                  30

Val Phe Ala Ala Gly Asn Gly Ala Ser Phe Glu Asp Asn Cys Asn Phe
        35                  40                  45

Asp Gly Tyr Thr Asn Ser Ile Tyr Ser Ile Thr Val Gly Ala Ile Asp
    50                  55                  60

Arg Glu Gly Asn His Pro Ser Tyr Ser Glu Ser Cys Ser Ala Gln Leu
65                  70                  75                  80

Val Val Ala Tyr Ser Ser Gly Ser
                85

<210> SEQ ID NO 14
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Asn Gly Lys Val Leu Ser Glu Pro Asp Val Ile Val Lys Lys Ala
1               5                   10                  15

Met Ile Lys Gly Ile Gln Glu Gly Arg Asp Lys Lys Gly Ala Ile Tyr
            20                  25                  30

Val Phe Ala Ser Gly Asn Gly Gly Arg Phe Gly Asp Ser Cys Asn Phe
        35                  40                  45

Asp Gly Tyr Thr Asn Ser Ile Tyr Ser Ile Thr Val Gly Ala Ile Asp
    50                  55                  60

Tyr Lys Gly Leu His Pro Gln Tyr Ser Glu Ala Cys Ser Ala Val Met
65                  70                  75                  80

Val Val Thr Tyr Ser Ser Gly Ser
                85

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Gly Arg Ser Met Glu Ala Pro Asp Gly Leu Ile Leu Lys Ala Met
1               5                   10                  15

Val Asn Gly Val Gln Lys Gly Arg Asp Gly Lys Gly Ser Val Phe Val
            20                  25                  30

Phe Ala Ala Gly Asn Gly Gly Gly Ser Asp Asp Gln Cys Asn Phe Asp
        35                  40                  45

-continued

```
Gly Tyr Thr Asn Ser Ile Phe Ser Val Thr Val Gly Ala Val Asp Arg
    50              55                  60

Lys Gly Leu His Pro Tyr Tyr Ser Glu Met Cys Ala Ala Met Met Val
65              70                  75                      80

Val Ala Pro Ser Ser Gly Ser Gly Asp His Ile His Thr Thr Asp Val
                85              90                  95

Gly Lys Asp Lys Cys Ser His Ser His Gly Gly Thr Ser Ala Ala Ala
            100             105                 110

Pro Leu Ala Val Gly
        115
```